United States Patent
Donovan

(10) Patent No.: US 10,441,733 B2
(45) Date of Patent: Oct. 15, 2019

(54) POWDER DISPERSION DEVICES AND METHODS

(71) Applicant: Respira Therapeutics, Inc., Santa Fe, NM (US)

(72) Inventor: Martin J. Donovan, El Paso, TX (US)

(73) Assignee: RESPIRA THERAPEUTICS, INC., Santa Fe, NM (US)

( * ) Notice: Subject to any disclaimer, the term of this patent is extended or adjusted under 35 U.S.C. 154(b) by 700 days.

(21) Appl. No.: 13/776,546

(22) Filed: Feb. 25, 2013

(65) Prior Publication Data

US 2013/0340747 A1     Dec. 26, 2013

Related U.S. Application Data

(60) Provisional application No. 61/664,013, filed on Jun. 25, 2012.

(51) Int. Cl.
*A61M 15/00*     (2006.01)

(52) U.S. Cl.
CPC .... *A61M 15/0045* (2013.01); *A61M 15/0033* (2014.02); *A61M 15/0086* (2013.01); *A61M 15/0028* (2013.01); *A61M 15/0065* (2013.01); *A61M 2202/064* (2013.01); *A61M 2205/07* (2013.01); *A61M 2206/14* (2013.01)

(58) Field of Classification Search
CPC ...... A61M 15/00; A61M 15/0003–001; A61M 15/0021; A61M 15/0028; A61M 15/0033; A61M 15/0035–0041; A61M 15/0043; A61M 15/0045; A61M 15/0051; A61M 15/0065; A61M 15/0086–0088; A61M 15/06; A61M 15/08–085; A61J 1/10; A61J 1/20; A61K 9/14
See application file for complete search history.

(56) References Cited

U.S. PATENT DOCUMENTS

| | | |
|---|---|---|
| 16,066 A | 11/1856 | Murphy |
| 361,748 A | 4/1867 | Culbertson |
| 263,451 A | 8/1882 | Adams |

(Continued)

FOREIGN PATENT DOCUMENTS

| | | |
|---|---|---|
| EP | 0147755 A2 | 7/1985 |
| EP | 0388621 A1 | 8/1992 |

(Continued)

OTHER PUBLICATIONS

International Search Report and Written Opinion of PCT/US2013/046779 dated Sep. 2, 2013, 20 pages.

(Continued)

*Primary Examiner* — Peter S Vasat
*Assistant Examiner* — Ned T Heffner
(74) *Attorney, Agent, or Firm* — Kilpatrick Townsend & Stockton LLP

(57) ABSTRACT

A dry powder inhaler may include a powder storage, an inlet channel, a dispersion chamber, and an outlet channel. A geometry of the inhaler may be such that a flow profile is generated within the dispersion chamber that causes an actuator to oscillate, enabling the actuator when oscillating to deaggregate powdered medicament within the dispersion chamber to be aerosolized and entrained by the air and delivered to a patient through the outlet channel.

21 Claims, 43 Drawing Sheets

(56) References Cited

U.S. PATENT DOCUMENTS

| | | |
|---|---|---|
| 376,819 A | 1/1888 | Glew |
| 419,942 A | 1/1890 | Harding |
| 598,286 A | 2/1898 | Curran |
| 631,621 A | 8/1899 | Curran |
| 658,436 A | 9/1900 | Groth |
| 844,097 A | 2/1907 | Caldwell |
| 1,599,959 A | 9/1926 | Fujimoto |
| 1,752,956 A | 4/1930 | Lex |
| 2,214,032 A | 9/1940 | Stewart |
| 2,470,296 A | 5/1949 | Fields |
| 2,513,145 A | 6/1950 | Chapple |
| 2,517,482 A | 8/1950 | Hall |
| 2,534,636 A | 12/1950 | Stirn |
| 2,549,303 A | 4/1951 | Friden |
| 2,569,720 A | 10/1951 | Jesnig |
| 2,573,918 A | 11/1951 | McCuiston |
| 2,579,280 A | 12/1951 | Trumbour et al. |
| 2,581,182 A | 1/1952 | Fields |
| 2,587,215 A | 2/1952 | Priestly |
| 2,603,215 A | 7/1952 | Arnow |
| 2,603,216 A | 7/1952 | Taplin et al. |
| 2,622,594 A | 12/1952 | Brooks |
| 2,641,255 A | 6/1953 | Leonaitis |
| 2,642,063 A | 6/1953 | Brown |
| 2,672,865 A | 3/1954 | Willis |
| 2,693,805 A | 11/1954 | Taplin et al. |
| 2,992,645 A | 7/1961 | Fowler |
| 3,105,488 A | 10/1963 | Richards |
| 3,518,992 A | 7/1970 | Howell et al. |
| 3,635,219 A | 1/1972 | Altounyan et al. |
| 3,807,400 A | 4/1974 | Cocozza |
| 3,837,341 A | 9/1974 | Bell |
| 3,858,583 A | 1/1975 | Hallworth et al. |
| 3,870,046 A | 3/1975 | Elliott |
| 3,888,252 A | 6/1975 | Side et al. |
| 3,888,253 A | 6/1975 | Watt et al. |
| 3,906,950 A | 9/1975 | Cocozza |
| 3,921,637 A | 11/1975 | Bennie et al. |
| 3,948,264 A | 4/1976 | Wilke et al. |
| 3,964,483 A | 6/1976 | Mathes |
| 3,971,377 A | 7/1976 | Damani |
| 3,980,074 A | 9/1976 | Watt et al. |
| 3,991,761 A | 11/1976 | Cocozza |
| 4,013,075 A | 3/1977 | Cocozza |
| 4,013,642 A | 3/1977 | Cocozza |
| 4,090,642 A | 5/1978 | Baker |
| 4,147,166 A | 4/1979 | Hansen |
| 4,216,768 A | 8/1980 | Jack |
| 4,338,931 A | 7/1982 | Cavazza |
| 4,353,365 A | 10/1982 | Hallworth et al. |
| 4,524,769 A | 6/1985 | Wetterlin |
| 4,570,630 A | 2/1986 | Elliott et al. |
| 4,735,358 A | 4/1988 | Morita et al. |
| 4,841,964 A | 6/1989 | Hurka et al. |
| 4,860,740 A | 8/1989 | Kirk et al. |
| 4,889,114 A | 12/1989 | Kladders |
| 4,907,583 A | 3/1990 | Wetterlin et al. |
| 5,033,463 A | 7/1991 | Cocozza |
| 5,035,237 A | 7/1991 | Newell et al. |
| 5,042,472 A | 8/1991 | Bunin |
| 5,161,524 A | 11/1992 | Evans |
| 5,186,164 A | 2/1993 | Raghuprasad |
| 5,201,308 A | 4/1993 | Newhouse |
| 5,239,991 A | 8/1993 | Chawla et al. |
| 5,239,992 A | 8/1993 | Bougamont et al. |
| 5,239,993 A | 8/1993 | Evans |
| 5,327,883 A | 7/1994 | Williams et al. |
| 5,347,999 A | 9/1994 | Poss et al. |
| 5,349,947 A | 9/1994 | Newhouse et al. |
| 5,372,128 A | 12/1994 | Haber et al. |
| 5,376,386 A | 12/1994 | Ganderton et al. |
| 5,388,572 A | 2/1995 | Mulhauser et al. |
| 5,394,868 A | 3/1995 | Ambrosio et al. |
| 5,408,994 A | 4/1995 | Wass et al. |
| 5,415,162 A | 5/1995 | Casper et al. |
| 5,429,122 A | 7/1995 | Zanen et al. |
| 5,437,270 A | 8/1995 | Braithwaite |
| 5,437,271 A | 8/1995 | Hodson et al. |
| 5,469,843 A | 11/1995 | Hodson |
| 5,476,093 A | 12/1995 | Lankinen |
| 5,482,032 A | 1/1996 | Smith et al. |
| 5,503,144 A | 4/1996 | Bacon |
| 5,505,196 A | 4/1996 | Herold et al. |
| 5,522,383 A | 6/1996 | Calvert et al. |
| 5,533,502 A | 7/1996 | Piper |
| 5,546,932 A | 8/1996 | Galli |
| 5,575,280 A | 11/1996 | Gupte et al. |
| 5,590,645 A | 1/1997 | Davies et al. |
| 5,595,175 A | 1/1997 | Malcher et al. |
| 5,615,670 A | 4/1997 | Rhodes |
| 5,617,844 A | 4/1997 | King |
| 5,619,984 A | 4/1997 | Hodson et al. |
| 5,628,307 A | 5/1997 | Clark et al. |
| 5,642,727 A * | 7/1997 | Datta ............... A61M 15/0045 128/202.25 |
| 5,651,359 A | 7/1997 | Bougamont et al. |
| 5,653,227 A | 8/1997 | Barnes et al. |
| 5,655,523 A | 8/1997 | Hodson et al. |
| 5,657,749 A | 8/1997 | Cox |
| 5,669,378 A | 9/1997 | Pera et al. |
| 5,673,685 A | 10/1997 | Heide et al. |
| 5,673,686 A | 10/1997 | Villax et al. |
| 5,687,912 A | 11/1997 | Denyer |
| 5,692,496 A | 12/1997 | Casper et al. |
| 5,694,920 A | 12/1997 | Abrams et al. |
| 5,699,789 A | 12/1997 | Hendricks |
| 5,724,959 A | 3/1998 | McAughey et al. |
| 5,740,793 A | 4/1998 | Hodson et al. |
| 5,743,250 A | 4/1998 | Gonda et al. |
| 5,752,505 A | 5/1998 | Ohki et al. |
| 5,775,320 A | 7/1998 | Patton et al. |
| 5,787,881 A | 8/1998 | Chawla |
| 5,813,401 A | 9/1998 | Radcliff et al. |
| 5,829,434 A | 11/1998 | Ambrosio et al. |
| 5,857,456 A | 1/1999 | Sun et al. |
| 5,860,419 A | 1/1999 | Davies et al. |
| 5,875,776 A | 3/1999 | Vaghefi |
| 5,881,719 A | 3/1999 | Gottenauer et al. |
| 5,989,217 A | 11/1999 | Ohki et al. |
| 6,026,809 A | 2/2000 | Abrams et al. |
| 6,029,663 A | 2/2000 | Eisele et al. |
| 6,065,472 A | 5/2000 | Anderson et al. |
| 6,071,498 A | 6/2000 | Narodylo et al. |
| 6,073,629 A * | 6/2000 | Hardy ............... A61M 15/0086 128/203.12 |
| 6,089,227 A | 7/2000 | Nilsson |
| 6,098,619 A | 8/2000 | Britto et al. |
| 6,123,070 A | 9/2000 | Bruna et al. |
| 6,138,673 A | 10/2000 | Shepherd |
| 6,152,130 A | 11/2000 | Abrams et al. |
| 6,153,224 A | 11/2000 | Staniforth |
| 6,182,655 B1 | 2/2001 | Keller et al. |
| 6,230,707 B1 | 5/2001 | Horlin |
| 6,234,169 B1 | 5/2001 | Bulbrook et al. |
| 6,237,590 B1 | 5/2001 | Leedom et al. |
| 6,237,591 B1 | 5/2001 | Jackson |
| 6,257,233 B1 | 7/2001 | Burr et al. |
| 6,286,507 B1 | 9/2001 | Jahnsson |
| 6,328,033 B1 | 12/2001 | Avrahami |
| 6,378,519 B1 | 4/2002 | Davies et al. |
| 6,425,888 B1 | 7/2002 | Embleton et al. |
| 6,427,688 B1 | 8/2002 | Ligotke et al. |
| 6,484,718 B1 | 11/2002 | Schaeffer et al. |
| 6,521,260 B1 | 2/2003 | Staniforth |
| 6,561,186 B2 | 5/2003 | Casper et al. |
| 6,626,173 B2 | 9/2003 | Genova et al. |
| 6,645,466 B1 | 11/2003 | Keller et al. |
| 6,651,341 B1 | 11/2003 | Myrman et al. |
| 6,655,380 B1 | 12/2003 | Andersson et al. |
| 6,655,381 B2 | 12/2003 | Keane et al. |
| 6,698,425 B1 | 3/2004 | Widerström |
| 6,715,486 B2 | 4/2004 | Gieschen et al. |
| 6,752,147 B1 | 6/2004 | Goldemann et al. |
| 6,779,520 B2 | 8/2004 | Genova et al. |

(56) References Cited

U.S. PATENT DOCUMENTS

| | | |
|---|---|---|
| 6,780,508 B1 | 8/2004 | Caponetti et al. |
| 6,810,872 B1 | 11/2004 | Ohki et al. |
| 6,840,239 B2 | 1/2005 | Myrman |
| 6,889,690 B2 | 5/2005 | Crowder et al. |
| 6,971,383 B2 | 12/2005 | Hickey et al. |
| 6,983,748 B2 | 1/2006 | Brown et al. |
| 7,011,818 B2 | 3/2006 | Staniforth |
| 7,025,056 B2 | 4/2006 | Eason et al. |
| 7,032,593 B2 | 4/2006 | Johnston et al. |
| 7,069,929 B2 | 7/2006 | Young et al. |
| 7,107,988 B2 | 9/2006 | Pinon et al. |
| 7,118,010 B2 | 10/2006 | Crowder et al. |
| 7,143,765 B2 | 12/2006 | Asking et al. |
| 7,228,860 B2 | 6/2007 | Andersson et al. |
| 7,252,087 B2 | 8/2007 | Wachtel |
| 7,278,425 B2 | 10/2007 | Edwards et al. |
| 7,284,553 B2 | 10/2007 | Hochrainer |
| 7,401,713 B2 | 7/2008 | Ede et al. |
| 7,556,035 B2 | 7/2009 | Young et al. |
| 7,617,822 B2 | 11/2009 | De Boer et al. |
| 7,718,163 B2 | 5/2010 | Staniforth |
| 7,735,485 B2 | 6/2010 | Yamashita et al. |
| 7,810,494 B2 | 10/2010 | Harmer et al. |
| 7,958,890 B2 | 6/2011 | Gieschen et al. |
| 8,037,880 B2 | 10/2011 | Zhu et al. |
| 8,091,558 B2 | 1/2012 | Martzel |
| 8,127,763 B2 | 3/2012 | Smyth et al. |
| 8,474,452 B2 | 7/2013 | Gumaste et al. |
| 8,561,609 B2 | 10/2013 | Donovan et al. |
| 8,651,104 B2 | 2/2014 | Donovan et al. |
| 9,295,792 B2 | 3/2016 | Wachtel et al. |
| 2001/0027790 A1 | 10/2001 | Gieschen et al. |
| 2002/0040713 A1 | 4/2002 | Eisele et al. |
| 2003/0015195 A1 | 1/2003 | Boer et al. |
| 2004/0025874 A1 | 2/2004 | Seppala |
| 2004/0055613 A1 | 3/2004 | Horian |
| 2004/0094152 A1 | 5/2004 | Harvey et al. |
| 2004/0123865 A1 | 7/2004 | Haikarainen et al. |
| 2004/0173211 A1 | 9/2004 | Kladders et al. |
| 2004/0206773 A1 | 10/2004 | Ede et al. |
| 2004/0244794 A1 | 12/2004 | Richards |
| 2005/0172962 A1 | 8/2005 | Gumaste et al. |
| 2005/0194008 A1 | 9/2005 | Andersson et al. |
| 2005/0274378 A1 | 12/2005 | Bonney et al. |
| 2005/0284473 A1* | 12/2005 | Young .............. A61M 15/0028 128/203.15 |
| 2006/0005833 A1 | 1/2006 | Gieschen et al. |
| 2006/0025326 A1* | 2/2006 | Lankinen .............. A61K 47/26 424/46 |
| 2006/0191534 A1 | 8/2006 | Hickey |
| 2007/0163574 A1 | 7/2007 | Rohrschneider et al. |
| 2007/0209661 A1 | 9/2007 | Smyth et al. |
| 2007/0215149 A1 | 9/2007 | King et al. |
| 2008/0035143 A1 | 2/2008 | Sievers |
| 2008/0078689 A1 | 4/2008 | Pentafragas |
| 2008/0115785 A1 | 5/2008 | Eason et al. |
| 2008/0190424 A1* | 8/2008 | Lucking .............. A61K 9/0075 128/203.15 |
| 2008/0202514 A1 | 8/2008 | Kriksunov |
| 2008/0314384 A1 | 12/2008 | Harris et al. |
| 2009/0013994 A1* | 1/2009 | Jones ................ A61M 16/0495 128/200.23 |
| 2009/0084379 A1 | 4/2009 | Goeckner et al. |
| 2009/0084380 A1 | 4/2009 | Gieschen et al. |
| 2009/0095294 A1 | 4/2009 | Smyth et al. |
| 2009/0165790 A1 | 7/2009 | Crowder et al. |
| 2009/0178676 A1 | 7/2009 | Villax et al. |
| 2009/0235929 A1 | 9/2009 | Egen et al. |
| 2009/0250058 A1 | 10/2009 | Lastow et al. |
| 2009/0308392 A1 | 12/2009 | Smutney et al. |
| 2009/0320838 A1 | 12/2009 | Malhotra et al. |
| 2010/0000529 A1 | 1/2010 | Prime et al. |
| 2010/0059049 A1 | 3/2010 | Genosar |
| 2010/0059051 A1 | 3/2010 | Kladders |
| 2010/0300440 A1 | 12/2010 | Deboeck et al. |
| 2010/0326438 A1 | 12/2010 | Dunne |
| 2011/0094507 A1* | 4/2011 | Wachtel ............ A61M 15/0045 128/200.21 |
| 2011/0120467 A1 | 5/2011 | Pardonge |
| 2011/0253140 A1 | 10/2011 | Smyth et al. |
| 2012/0145150 A1 | 6/2012 | Donovan et al. |
| 2012/0234322 A1 | 9/2012 | Smyth et al. |
| 2012/0291780 A1 | 11/2012 | Donovan et al. |
| 2013/0032145 A1 | 2/2013 | Adler et al. |
| 2013/0042864 A1 | 2/2013 | Adler et al. |
| 2013/0213397 A1 | 8/2013 | Curtis et al. |
| 2013/0340754 A1 | 12/2013 | Donovan |

FOREIGN PATENT DOCUMENTS

| | | |
|---|---|---|
| EP | 1 291 032 A2 | 3/2003 |
| EP | 1 658 872 A2 | 5/2006 |
| EP | 2863972 | 4/2015 |
| EP | 2863973 | 4/2015 |
| GB | 2334686 A | 1/1999 |
| IN | 405/DELNP/2015 A | 6/2015 |
| IN | 408/DELNP/2015 A | 6/2015 |
| JP | 2002537952 A | 11/2002 |
| JP | 2015521526 | 7/2015 |
| JP | 2015525111 | 9/2015 |
| WO | 97/04827 | 2/1997 |
| WO | 2006/031775 A2 | 3/2006 |
| WO | 2006/037636 A2 | 4/2006 |
| WO | 2006037636 A2 | 4/2006 |
| WO | 2006/090149 A2 | 8/2006 |
| WO | 2010/014827 A2 | 2/2010 |
| WO | 2012/079524 A1 | 6/2012 |
| WO | 2014/004250 A1 | 1/2014 |
| WO | 2014/004256 A1 | 1/2014 |
| WO | 2015/001281 A1 | 1/2015 |
| WO | 2015/127258 A1 | 8/2015 |

OTHER PUBLICATIONS

International Search Report and Written Opinion of PCT/US2013/046795 dated Oct. 9, 2013, 13 pages.

IPRP dated Jan. 8, 2015 for International Patent Application PCT/US2013/046795, all pages.

IPRP dated Jan. 8, 2015 for International Patent Application PCT/US2013/046779, all pages.

Coates, et al., "Effect of Design on the Performance of a Dry Powder Inhaler Using Computational Fluid Dynamics. Part 2: Air Inlet Size," Journal of Pharmaceutical Sciences, vol. 95, No. 6, Jun. 2006, 11 pages.

Coates, et al., "The Role of Capsule on the Performance of a Dry Powder Inhaler Using Computational and Experimental Analyses," Pharmaceutical Research, vol. 22, No. 6, Jun. 2005; DOI: 10.1007/s11095-005-4587-y, 10 pages.

Coates, et al., "Effect of Design on the Performance of a Dry Powder Inhaler Using Computational Fluid Dynamics. Part 1: Grid Structure and Mouthpiece Length," Journal of Pharmaceutical Sciences, vol. 93, No. 11, Nov. 2004, 14 pages.

Crowder, et al., "2001: An Odyssey in Inhaler Formulation and Design." Pharmaceutical Technology, pp. 99-113 (Jul. 2001), 9 pages.

Hickey, et al., "A New Millenium for Inhaler Technology," Pharmaceutical Technology, vol. 21, pp. 116-125 (Jun. 1997), 7 pages.

Martonen, T., et al., "Issues in Drug Delivery: Concepts and Practice," Respiratory Care, Sep. 2005, vol. 50, No. 9, 25 pages.

Peart, et al., "New Developments in Dry Powder Inhaler Technology," American Pharmaceutical Review, vol. 4, pp. 37-45 (2001), 7 pages.

Prime, et al., "Review of Dry Powder Inhalers," Advanced Drug Delivery Reviews, vol. 26, pp. 51-58 (1997), 8 pages.

Smyth, et al., "Carriers in Drug Powder Delivery—Implications for Inhalation System Design," Am. J. Drug Deliv., vol. 3(2), pp. 117-132 (2005), 17 pages.

International Search Report and Written Opinion for PCT/US2011/063816 dated Mar. 21, 2012, 8 pages.

(56) References Cited

OTHER PUBLICATIONS

International Search Report and Written Opinion for PCT/US2015/016891 dated May 15, 2015, all pages.
International Search Report and Written Opinion for PCT/US2013/046795 dated Oct. 9, 2013, all pages.
International Preliminary Report on Patentability for PCT/ US2013/046795 dated Jan. 8, 2015, all pages.
International Search Report and Written Opinion for PCT/US2013/046779 dated Sep. 2, 2013, all pages.
International Preliminary Report on Patentability for PCT/US2013/046779 dated Jan. 8, 2015, all pages.
Supplementary European Search Report for EP 13808599 dated Nov. 13, 2015, all pages.
Supplementary European Search Report for EP 13810308 dated Nov. 13, 2015, all pages.
Office Action for European patent application No. 11 847 102.8 dated Feb. 9, 2016, all pages.
Japanese Patent Office, Official Action for Japanese Application No. 2008-558311 dated Jan. 19, 2012, all pages.
EP Patent Application No. 15751697.2 filed Feb. 20, 2015, Extended European Search Report dated Jan. 12, 2018, all pages.
JP Patent Application No. 2015-520317 filed Jun. 20, 2013, Office Action dated Aug. 8, 2017, all pages.

* cited by examiner

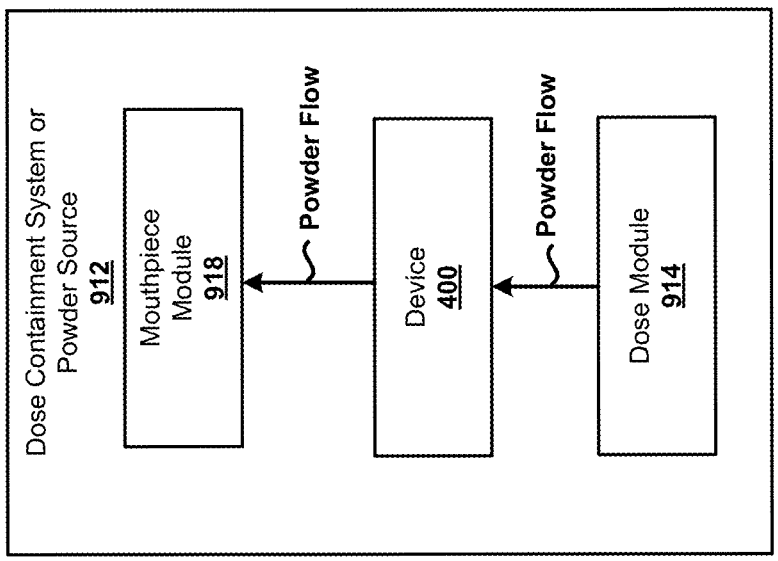
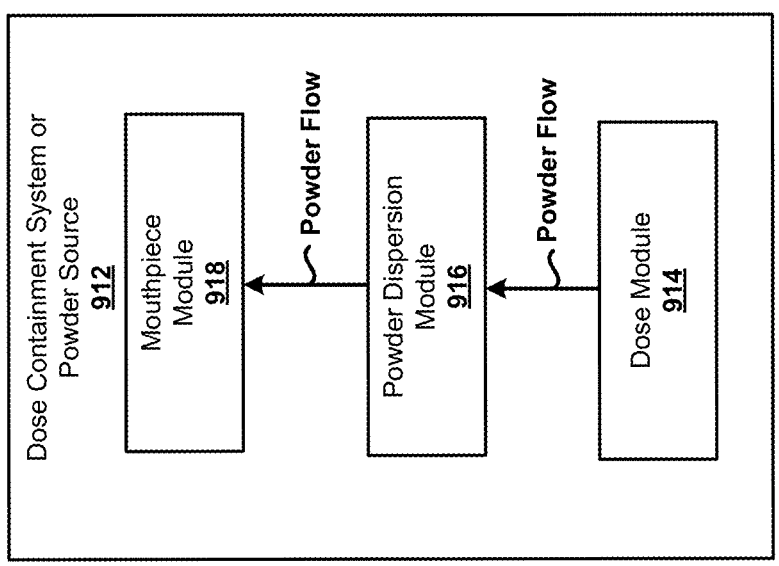
FIG. 10

POWDER DISPERSION DEVICES AND METHODS

CROSS-REFERENCE TO RELATED APPLICATION

This application claims the benefit of U.S. Provisional Patent Application No. 61/664,013, filed 25 Jun. 2012, entitled "Powder Dispersion Devices and Method," the entirety of which is hereby incorporated by reference for all purposes.

This application is related to U.S. Nonprovisional patent application Ser. No. 13/776,558, filed on Feb. 25, 2013, entitled "Powder Dispersion Devices and Method," the entirety of which is hereby incorporated by reference for all purposes.

BACKGROUND

In the field of dry powder inhalers, there is generally a trade-off between performance, as defined by the efficiency of the nominal or loaded dose in the inhaler that is delivered to the lung, and device complexity, in terms of the internal geometry, specifically, the powder flow path that the dose travels as it exits the device. In many instances, inhalers with relatively uncomplicated flow paths may be characterized by poor efficiency, as generally less than 30% of the nominal dose is delivered to the deep lung. Alternatively, inhalers with relatively more complex internal flow paths, may provide increased efficiency, such as less than or equal to 40% of the nominal dose, though the increased complexity of the internal flow path may lead to increased deposition within the inhaler, effectively lowering the overall dose delivered to the patient and contaminating the device.

SUMMARY

This Summary does not in any way limit the scope of the claimed subject matter.

The present disclosure is directed to a powder dispersion mechanism that is compact, breath-actuated, and effective or sufficient at promoting efficient particle dispersion across a range of doses such as from, for example, low microgram doses to doses requiring many milligrams. Accordingly, in some embodiments, a powder dispersion mechanism is disclosed that employs a bead contained within a "small" volume dispersion chamber, with a straight flow path, and that is breath-actuated. The bead may oscillate, generally linearly in certain embodiments, along an axis of the dispersion chamber when the patient inhales through the device, such that it does not require an energy source other than a patient's inspiratory maneuver to function. This may be referred to as "passive" bead activation or actuation. However, the present disclosure is not so limiting. For example, bead activation may be "active," where an external energy source is coupled with the patients inhalation flow stream to induce oscillation.

In an aspect, a dry powder inhaler is disclosed. The dry powder inhaler may include a first chamber that is adapted to receive an aerosolized powdered medicament from an inlet channel. A volume of the first chamber may be greater than a volume of the inlet channel. The dry powder inhaler may include a dispersion chamber that is adapted to receive at least a portion of the aerosolized powdered medicament from the first chamber. The dispersion chamber may hold an actuator that is movable within the dispersion chamber along a longitudinal axis. The dry powder inhaler may include an outlet channel through which air and powdered medicament exit the inhaler to be delivered to a patient. A geometry of the inhaler may be such that a flow profile is generated within the dispersion chamber that causes the actuator to oscillate along the longitudinal axis, enabling the oscillating actuator to effectively disperse powdered medicament received in the dispersion chamber for delivery to the patient through the outlet channel.

In an aspect, a dry powder inhaler system is disclosed. The dry powder inhaler system may include a receptacle containing an amount of powdered medicament. The dry powder inhaler system may include an inlet channel that is adapted to receive air and powdered medicament from the receptacle. The dry powder inhaler system may include a first chamber that is adapted to receive air and powdered medicament from the inlet channel. A volume of the first chamber may be greater than volume of the inlet channel. The dry powder inhaler system may include a dispersion chamber that is adapted to receive air and powdered medicament from the first chamber. The dispersion chamber may hold an actuator that is movable within the dispersion chamber along a longitudinal axis. The dry powder inhaler system may include an outlet channel through which air and powdered medicament exit the dispersion chamber to be delivered to a patient. A geometry of the system may be such that a flow profile is generated within the system that causes the actuator to oscillate along the longitudinal axis, enabling the oscillating actuator to effectively disperse powdered medicament received in the dispersion chamber for delivery to the patient through the outlet channel.

In an aspect, a method for aerosolizing a powdered medicament is disclosed. The method may include providing an inhaler comprising a first chamber, and a dispersion chamber, the dispersion chamber containing an actuator that is movable within the dispersion chamber along a longitudinal axis, and an outlet channel. The method may include inducing air flow through the outlet channel to cause air and powdered medicament to enter into the first chamber through the inlet channel into the dispersion chamber, and to cause the actuator to oscillate within the dispersion chamber to effectively disperse powdered medicament passing through the first chamber and the dispersion chamber to be entrained by the air and delivered to the patient through the outlet channel.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. When only the first reference label is used in the specification, the description is applicable to any one of the similar components having the same first reference label irrespective of the second reference label.

FIG. 10 shows the device of FIG. 4 incorporated internally into an existing inhaler system.

DETAILED DESCRIPTION

The present disclosure relates to the field of pulmonary drug delivery, and more specifically to dry powder inhalers that deliver a medicament into the lungs of a patient. In example embodiments, such a powder dispersion mechanism may comprise of a bead positioned within a chamber that is arranged and configured to induce a sudden, rapid, or otherwise abrupt expansion of a flow stream upon entering the chamber.

In general, the chamber may be coupled to any form or type of dose containment system or source that supplies powdered medicament into the chamber. For example, in one embodiment, the dose containment source may comprise or be incorporated within, for example, a powder dispersion device such as the TOBI® Podhaler®, the FORADIL® Aerolizer®, the SPIRIVA® HandiHaler®, the FLOVENT® Diskus®, the SEREVENT® Diskus®, the ADVAIR® Diskus®, the ASMANEX® Twisthaler®, the SYMBICORT® Turbuhaler®, the Budelin® Novolizer®, and many others. The bead when oscillating within the chamber may then disrupt and aerosolize powder agglomerates within the chamber, as passed from the source, to provide for more effective deposition of medicament into the lungs of a patient. Still other embodiments are possible.

Figure 1:
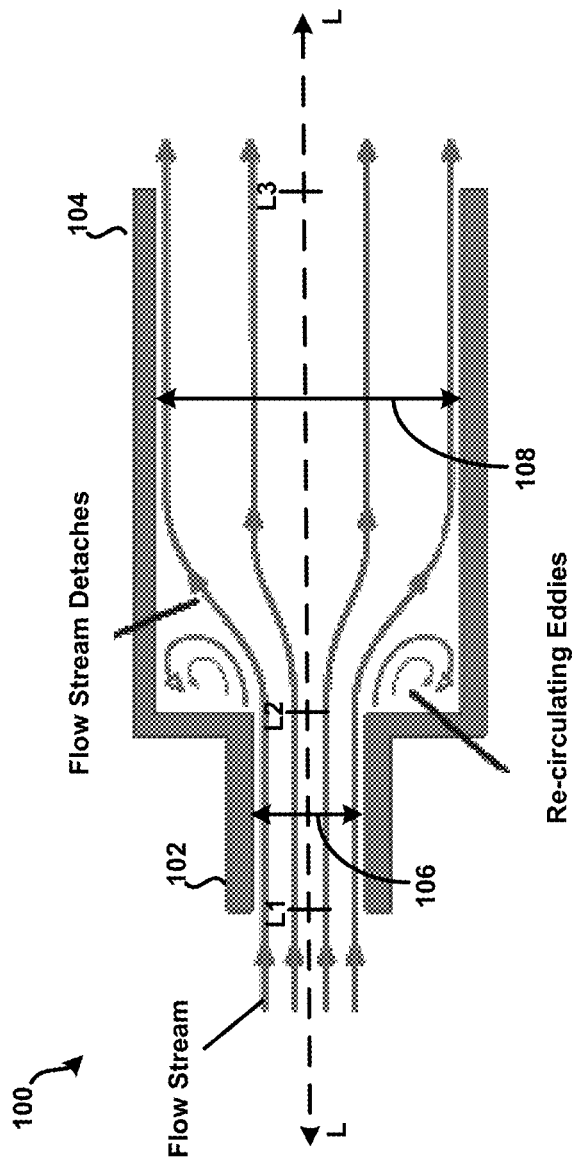
FIG. 1 shows a cross-section of an example tubular body having an inlet and a dispersion chamber.

Referring now to FIG. 1, a cross-section of an example tubular body 100 having an inlet 102 and a dispersion chamber 104 is shown according to the principles of the present disclosure. In this example, a fluid (e.g., air) flow path of the inlet 102 is defined by a first internal diameter 106, and a fluid flow path of the chamber 104 is defined by a second internal diameter 108. Although shown approximately constant in FIG. 1, at least one of the first internal diameter 106 and the second internal diameter 108 may vary in dimension as defined with respect to a longitudinal axis L of the tubular body 100. In addition to providing desirable fluid flow characteristics, as discussed further below, these configurable dimensions may be defined such as to provide for a draft angle for injection molding.

For example, the first internal diameter 106 may taper inwardly, towards and as measured with reference to the longitudinal axis L, beginning approximately at a reference point L1 of the longitudinal axis L and ending approximately at a reference point L2 of the longitudinal axis L. Other embodiments are possible. For example, the first internal diameter 106 may taper inwardly towards the longitudinal axis L beginning approximately at the reference point L2, and ending approximately at the reference point L1. In a similar manner, the second internal diameter 108 may taper inwardly, towards and as measured with reference to the longitudinal axis L, beginning approximately at the reference point L2, and ending approximately at a reference point L3 of the longitudinal axis L. In another embodiment, the second internal diameter 108 may taper inwardly towards the longitudinal axis L beginning approximately at the reference point L3 and ending approximately at the reference point L2. Still other embodiments are possible.

For example, it is contemplated that an internal structural profile of at least one of the inlet 102 and the chamber 104 may be defined, as desired, such as to obtain or otherwise realize particular fluid flow characteristics within the tubular body 100. For example, as depicted in FIG. 1, the tubular body 100 may be arranged and configured such that a sudden flow stream expansion may occur when the relatively "small" cross-sectional fluid flow path of or defined by the inlet 102 opens abruptly into a "larger" cross-sectional fluid flow path of or defined by the chamber 104. In this example, and as discussed in further detail below, high-energy forces may develop by within the chamber 104. In one aspect, this may be due to relatively "low" pressure regions induced by relatively "high" velocity fluid entering the chamber 104, where a portion of the flow stream detaches. Other mechanisms may contribute to the development of high-energy fluid flow within the chamber 104 as well. Further, such high-energy fluid flow, along with mechanical impact forces, may disrupt and aerosolize medicament powder agglomerates within the chamber 104 to provide for more effective deposition of medicament into the lungs of a patient.

Still other embodiments of the example tubular body 100 are possible as well. For example, in some embodiments, a difference between the reference point L1 of the longitudinal axis L and the reference point L2 may approach zero (0). In this example, the tubular body 100 may consist only of the chamber 104. Here, instead of an "inlet tube," the tubular body 100 may consist of an "inlet hole."

Figure 2:
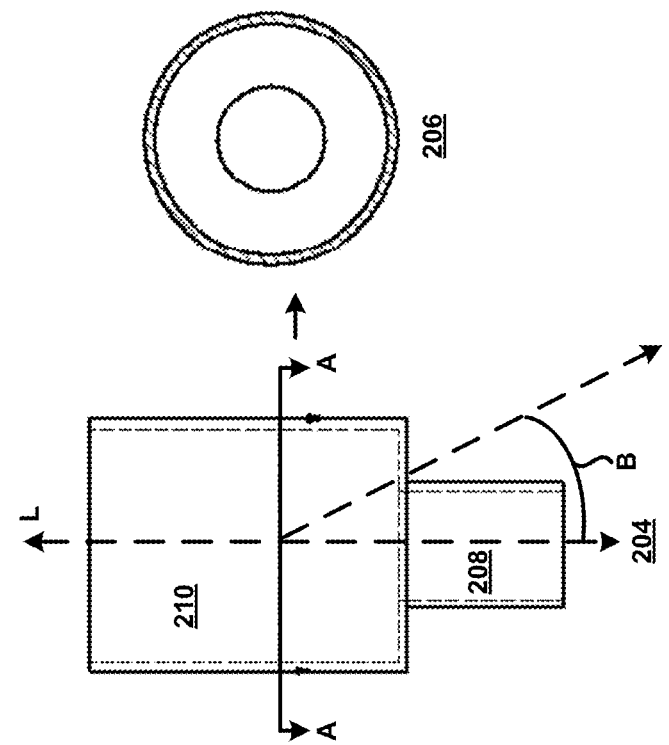
FIG. 2 shows the tubular body of FIG. 1 in multiple views.

Referring now additionally to FIG. 2, the tubular body 100 of FIG. 1 is shown in multiple views. In particular, the tubular body 100 of FIG. 1 is shown in perspective view 202, side view 204, and cross-section view 206. In this example, the cross-section view 206 is taken along an axis A-A of the side view 204. Additionally, and as illustrated in FIG. 1, the fluid flow path of or defined by the inlet 102 is coaxially aligned with the fluid flow path of or defined by the chamber 104. This is in contrast with a substantially "off-axis" alignment of the inlet 102 and the chamber 104, illustrated conceptually in FIG. 2 by a finite angle B defined with respect to the longitudinal axis L. A coaxial alignment may provide a number of advantages over such an "off-axis" alignment, such as facilitating or otherwise assisting in the development of high-energy forces within the chamber 104. The coaxial alignment may further enable the efficient transfer of powder into the chamber 104. However, other embodiments are possible. For example, in some embodiments, a central longitudinal axis of the inlet 102 may be at least slightly offset yet parallel to a central longitudinal axis of the chamber 104. Other benefits and/or advantages associated with the alignment of the inlet 102 and the chamber 104 may be understood from the preceding description provided in connection with FIGS. 1-2, and from the following description provided in connection with FIGS. 3-42.

Figure 3:
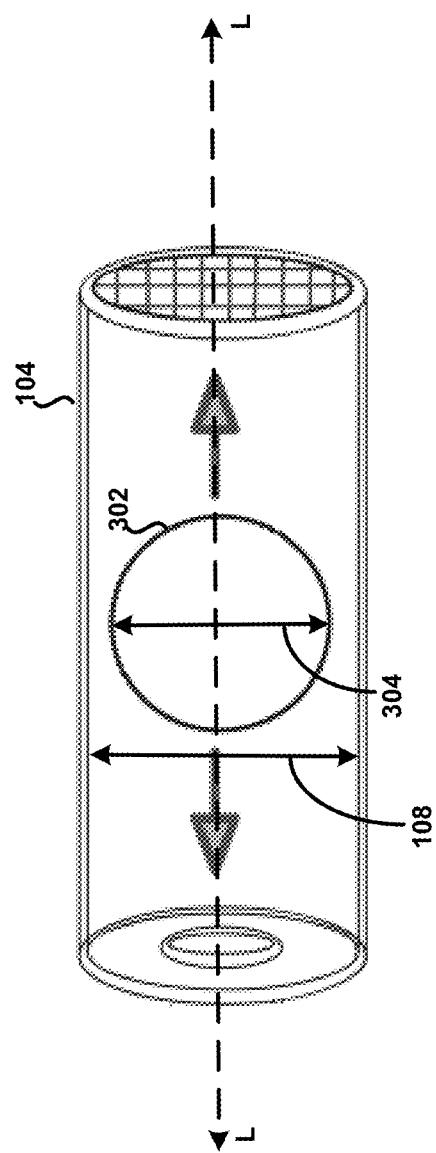
FIG. 3 shows a bead positioned within a chamber of the tubular body of FIG. 1.

For example, referring now additionally to FIG. 3, a bead 302 may be positioned within the chamber 104 of the tubular body 100 of FIGS. 1-2. In this example, the bead 302 may be approximately spherical, at least on the macroscale, and oscillate in a manner similar to that described in U.S. application Ser. No. 13/469,963, filed 11 May 2012, and entitled "Bead-Containing Dry Powder Inhaler," the complete disclosure of which is herein incorporated by reference.

Further, a relationship between the diameter 304 of the bead 302, the first internal diameter 106 of the inlet 102, and the second internal diameter 108 of the chamber 104 may be of the form: $d_{bead}^2 \cong (d_{inlet})(d_{chamber})$. In general, this relationship may hold in scenarios where $d_{bead}$ and $d_{inlet}$ and $d_{chamber}$ are of similar order of magnitude. For example, in one embodiment $d_{bead}$ may be about 5 mm, $d_{inlet}$ may be about 3.39 mm, and $d_{chamber}$ may be about 7.37 mm, within manufacturing tolerance. In this example, a length of the chamber 104, $l_{chamber}$, such as defined by a distance approximately between the reference point L2 and the reference point L3 of the longitudinal axis L (see FIG. 1), may be less than or equal to about less than twice the diameter 304 of the bead 302.

In some embodiments, a preferred diameter of the bead 302 may be within a range of about 0.5 mm to about 15 mm. The relationship $d_{bead}^2 \cong (d_{inlet})(d_{chamber})$ may then be used to determine $d_{inlet}$ and $d_{chamber}$. In some embodiments, a preferred diameter of the bead 302 may be within a range of about 1.5 mm to about 6 mm. Still other embodiments are possible.

In some embodiments, a preferred ratio of the diameter of the chamber 104 to that of the inlet 102 may be within a range of about 1.1 to about 3.0. At respective extremes, the relationship $d_{bead}^2 \cong (d_{inlet})(d_{chamber})$ may thus be rewritten as, based on substitution, $d_{bead}^2 \cong (d_{chamber})^2/1.1$ and $d_{bead}^2 \cong (d_{chamber})^2/3$.

In some embodiments, it may be preferred that the length of the chamber 104, $l_{chamber}$, is about 1.2 times to about 5 times the diameter of the bead 302. In other embodiments, it may be preferred that the length of the chamber 104, $l_{chamber}$, is about 1.5 times to about 3 times the diameter of the bead 302. In other embodiments, it may be preferred that the length of the chamber 104, $l_{chamber}$, is about 2 times to about 2.5 times the diameter of the bead 302.

In example embodiments, the length of the chamber 104 may determine whether the bead 302 freely oscillates, without physical interaction with ends of the chamber 104. In this manner, the length of the chamber 302 may facilitate free oscillation of the bead 302. A substantially "freely" oscillating bead 302 may even more effectively disrupt and aerosolize powder agglomerates within the chamber 104, as passed from the source, to provide for more effective deposition of medicament into the lungs of a patient.

For example, a study was performed to evaluate the length of the chamber 104 and to determine whether a particular length of chamber 104 would allow the bead 302 to "freely" oscillate within the chamber 104. In particular, using a device similar to the device 400, a bead of fixed diameter, about 4 mm, was used across the study. The length of the chamber however was varied as 1.5×, 2.0×, 3.0×, 3.5×, 4.0×, and 9.8× diameter of the bead. In this manner, the study included evaluating at least six different device configurations. In general, it was found that oscillation of the bead within the chamber was similar for lengths up to and including 3.5× diameter of the bead, yet varied for lengths 4.0× and 9.8× diameter of the bead. For example, a similar flow rate through the device was needed to allow the bead to "freely" oscillate within the chamber at least for chamber lengths of 3.0× and 3.5× diameter of the bead. However, a "higher" or "greater" flow rate was needed to allow the bead to "freely" oscillate within the chamber for a chamber length of 4.0× diameter of the bead. Further the bead did not appear to "freely" oscillate within the chamber for a chamber length of 9.8× diameter of the bead, for any flow rate through the device. At this chamber length, the bead may not be fully influenced by pressure at the inlet of the device. Other mechanisms may be possible as well.

In another example, a study was performed to evaluate the length of the chamber 104 and to determine whether a particular diameter of the bead 302, for a fixed length of the chamber 104, would allow the bead 302 to "freely" oscillate within the chamber 104. In particular, using a device similar to the device 400, a chamber of fixed length and diameter, about 10 mm length and about 6 min diameter, was used across the study. The diameter of the bead however was varied as 3.7 mm, 4 mm, and 4.7 mm. In this manner, the study included evaluating at least three different device configurations. In general, it was found that oscillation of the bead within the chamber for a 4 mm bead did "freely" oscillate within the chamber at a first particular flow rate. At this flow rate for this device configuration, a distinct audible pitch produced by oscillation of the bead within the chamber may be observed. Operation and characteristics of the device 400 having a 4 mm bead diameter is discussed in further detail below.

Further, it was found that oscillation of the bead within the chamber for a 3.7 mm bead did "freely" oscillate within the chamber 104 at or about the first particular flow rate. However, a flow rate greater than the first particular flow rate was needed to observe an audible pitch similar to the distinct audible pitch produced by oscillation of the bead within the chamber for the 4 mm bead. Here, a greater flow rate may be required to produce the audible pitch due to a reduced effective cross-sectional area of the 3.7 mm bead, as compared to the 4 mm bead. Other mechanisms may be possible as well. Further, it was found that oscillation of the bead within the chamber for a 4.7 mm bead did not "freely" oscillate within the chamber at or about the first particular flow rate. Here, the effective cross-sectional area of the 4.7 mm bead may be too large such as to prohibit "free" oscillation within the chamber. Other mechanisms may be possible as well.

Continuing with the above dimensional example, the length of the chamber 104 may thus be about 10 mm. In this example, and when the power law relationship between the diameters of the bead 302, the inlet 102, and the chamber 104 is observed, the bead 302 may oscillate within the chamber 104 generally without experiencing continuous physical collisions with either end of the chamber 104. Such an arrangement may further facilitate development of high energy forces within the chamber 104 to more efficiently disrupt and aerosolize medicament powder agglomerates within the chamber 104 for more effective deposition of medicament into the lungs of a patient.

In general, high-energy forces may refer to dispersive forces that may strip drug from the bead 302, and deaggregation or deagglomeration forces that may break-up or break-apart aggregates in powder fed into the chamber 104. Here, the terms deaggregation or deagglomeration, and aggregation or agglomeration may be used interchangeably. The high-energy forces may be generated by the bead 302 when rapidly oscillating within the chamber 104 via formation of turbulence and eddies within the chamber 104, compression and decompression zones within the chamber 104, and the like.

When a DPF (Dry Powder Formulation) is passed through the chamber 104 containing the bead 302, which is oscillating "rapidly" such as, for example, at a frequency greater than about 100 Hz, these high frequency oscillations of the bead 302 may produce high-energy forces within the chamber 104. This may disrupt agglomerates of drug particles that may be held together at least by cohesive forces, such as by van der Waals forces, static electrical forces, etc. Additionally, physical collisions between the bead 302, when rapidly oscillating, and potentially aggregated or agglomerated powder particles as they pass through the chamber 104 may promote de-aggregation of the agglomerates. Details associated with interaction(s) between the bead 302 and powder particles as transferred through the chamber 104 are discussed further below. The oscillation frequency may typically be between about 1 to about 1,000 Hz, and may preferably be between about 25 to about 500 Hz, although other frequencies may also occur. However, in some cases, the oscillation frequency could be up to about 2,000 Hz.

The powder dispersion devices and methods in accordance with the present disclosure may be applicable in many scenarios. For example, APIs (Active Pharmaceuticals Ingredients), or active agents, that may be used with any of the mechanisms described within the context of the present disclosure may include analgesic anti-inflammatory agents such as, acetaminophen, aspirin, salicylic acid, methyl salicylate, choline salicylate, glycol salicylate, 1-menthol, camphor, mefenamic acid, fluphenamic acid, indomethacin, diclofenac, alclofenac, ibuprofen, ketoprofen, naproxene, pranoprofen, fenoprofen, sulindac, fenbufen, clidanac, flurbiprofen, indoprofen, protizidic acid, fentiazac, tolmetin, tiaprofenic acid, bendazac, bufexamac, piroxicam, phenylbutazone, oxyphenbutazone, clofezone, pentazocine, mepirizole, and the like.

Other drugs that may be used include drugs having an action on the central nervous system, for example sedatives, hypnotics, antianxiety agents, analgesics and anesthetics, such as, chloral, buprenorphine, naloxone, haloperidol, fluphenazine, pentobarbital, phenobarbital, secobarbital, amobarbital, cydobarbital, codeine, lidocaine, tetracaine, dyclonine, dibucaine, cocaine, procaine, mepivacaine, bupivacaine, etidocaine, prilocalne, benzocaine, fentanyl, nicotine, and the like.

Local anesthetics such as, benzocaine, procaine, dibucaine, lidocaine, and the like.

Still other drugs include antihistaminics or antiallergic agents such as, diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine, chlorpheniramine, and the like.

Anti-allergenics such as, antazoline, methapyrilene, chlorpheniramine, pyrilamine, pheniramine, and the like.

Decongestants such as, phenylephrine, ephedrine, naphazoline, tetrahydrozoline, and the like.

Other drugs include antipyretics such as, aspirin, salicylamide, non-steroidal anti-inflammatory agents, and the like.

Antimigrane agents such as, dihydroergotamine, pizotyline, and the like.

Acetonide anti-inflammatory agents, such as hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, tolmetin, and the like.

Muscle relaxants such as, tolperisone, baclofen, dantrolene sodium, cyclobenzaprine, and the like.

Steroids may also be used, including androgenic steroids, such as, testosterone, methyltestosterone, fluoxymesterone, estrogens such as, conjugated estrogens, esterified estrogens, estropipate, 17-β estradiol, 17-β estradiol valerate, equilin, mestranol, estrone, estriol, 17β ethinyl estradiol, diethylstilbestrol, progestational agents, such as, progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17-α hydroxyprogesterone, dydrogesterone, dimethisterone, ethinylestrenol, norgestrel, demegestone, promegestone, megestrol acetate, and the like.

Respiratory agents that may be used include: theophilline and β2-adrenergic agonists, such as, albuterol, terbutaline, metaproterenol, ritodrine, carbuterol, fenoterol, quinterenol, rimiterol, solmefamol, soterenol, tetroquinol, tacrolimus, and the like.

Sympathomimetics such as, dopamine, norepinephrine, phenylpropanolamine, phenylephrine, pseudoephedrine, amphetamine, propylhexedrine, arecoline, and the like.

Antimicrobial agents that may be used include antibacterial agents, antifungal agents, antimycotic agents and antiviral agents; tetracyclines such as, oxytetracycline, penicillins, such as, ampicillin, cephalosporins such as, cefalotin, aminoglycosides, such as, kanamycin, macrolides such as, erythromycin, chloramphenicol, iodides, nitrofrantoin, nystatin, amphotericin, fradiomycin, sulfonamides, purroInitrin, clotrimazole, itraconazole, miconazole chloramphenicol, sulfacetamide, sulfamethazine, sulfadiazine, sulfamerazine, sulfamethizole and sulfisoxazole; antivirals, including idoxuridine; clarithromycin; and other anti-infectives including nitrofurazone, and the like.

Antihypertensive agents that may be used include clonidine, α-methyldopa, reserpine, syrosingopine, rescinnamine, cinnarizine, hydrazine, prazosin, and the like.

Other possible drugs include antihypertensive diuretics such as, chlorothiazide, hydrochlorothrazide, bendoflumethazide, trichlormethiazide, furosemide, tripamide, methylclothiazide, penfluzide, hydrothiazide, spironolactone, metolazone, and the like.

Cardiotonics such as, digitalis, ubidecarenone, dopamine, and the like.

Coronary vasodilators such as, organic nitrates such as, nitroglycerine, isosorbitol dinitrate, erythritol tetranitrate, and pentaerythritol tetranitrate, dipyridamole, dilazep, trapidil, trimetazidine, and the like.

Vasoconstrictors such as, dihydroergotamine, dihydroergotoxine, and the like.

β-blockers or antiarrhythmic agents such as, timolol pindolol, propranolol, and the like.

Humoral agents such as, the prostaglandins, natural and synthetic, for example PGE1, PGE2α, and PGF2α, and the PGE1 analog misoprostol, and the like.

Antispasmodics such as, atropine, methantheline, papaverine, cinnamedrine, methscopolamine, and the like.

Other drugs that may be used include calcium antagonists and other circulatory organ agents, such as, aptopril, diltiazem, nifedipine, nicardipine, verapamil, bencyclane, ifenprodil tartarate, molsidomine, clonidine, prazosin, and the like.

Anti-convulsants such as, nitrazepam, meprobamate, phenytoin, and the like.

Agents for dizziness such as, isoprenaline, betahistine, scopolamine, and the like.

Tranquilizers such as, reserprine, chlorpromazine, and antianxiety benzodiazepines such as, alprazolam, chlordiazepoxide, clorazeptate, halazepam, oxazepam, prazepam, clonazepam, flurazepam, triazolam, lorazepam, diazepam, and the like.

Antipsychotics such as, phenothiazines including thiopropazate, chlorpromazine, triflupromazine, mesoridazine, piperracetazine, thioridazine, acetophenazine, fluphenazine, perphenazine, trifluoperazine, and other major tranquilizers such as, chlorprathixene, thiothixene, haloperidol, bromperidol, loxapine, and molindone, as well as, those agents used at lower doses in the treatment of nausea, vomiting, and the like.

Drugs for Parkinson's disease, spasticity, and acute muscle spasms such as levodopa, carbidopa, amantadine, apomorphine, bromocriptine, selegiline (deprenyl), trihexyphenidyl hydrochloride, benztropine mesylate, procyclidine hydrochloride, baclofen, diazepam, dantrolene, and the like.

Respiratory agents such as, codeine, ephedrine, isoproterenol, dextromethorphan, orciprenaline, ipratropium bromide, cromglycic acid, and the like.

Non-steroidal hormones or antihormones such as, corticotropin, oxytocin, vasopressin, salivary hormone, thyroid hormone, adrenal hormone, kallikrein, insulin, oxendolone, and the like.

Vitamins such as, vitamins A, B, C, D, E and K and derivatives thereof, calciferols, mecobalamin, and the like, for use dermatologically for example.

Enzymes such as, lysozyme, urokinaze, and the like.

Herb medicines or crude extracts such as, Aloe vera, and the like.

Antitumor agents such as, 5-fluorouracil and derivatives thereof, krestin, picibanil, ancitabine, cytarabine, and the like.

Anti-estrogen or anti-hormone agents such as, tamoxifen or human chorionic gonadotropin, and the like.

Miotics such as pilocarpine, and the like.

Cholinergic agonists such as, choline, acetylcholine, methacholine, carbachol, bethanechol, pilocarpine, muscarine, arecoline, and the like.

Antimuscarinic or muscarinic cholinergic blocking agents such as, atropine, scopolamine, homatropine, methscopolamine, homatropine methylbromide, methantheline, cyclopentolate, tropicamide, propantheline, anisotropine, dicyclomine, eucatropine, and the like. Mydriatics such as, atropine, cyclopentolate, homatropine, scopolamine, tropicamide, eucatropine, hydroxyamphetamine, and the like.

Psychic energizers such as 3-(2-aminopropy)indole, 3-(2-aminobutyl)indole, and the like, such as ipratropium, tiotropium, glycopyrrolate (glycopyrronium), aclidinium, and the like.

Antidepressant drugs such as, isocarboxazid, phenelzine, tranylcypromine, imipramine, amitriptyline, trimipramine, doxepin, desipramine, nortriptyline, protriptyline, amoxapine, maprotiline, trazodone, and the like.

Anti-diabetics such as, insulin, and anticancer drugs such as, tamoxifen, methotrexate, and the like.

Anorectic drugs such as, dextroamphetamine, methamphetamine, phenylpropanolamine, fenfluramine, diethylpropion, mazindol, phentermine, and the like. Anti-malarials such as, the 4-aminoquinolines, alphaaminoquinolines, chloroquine, pyrimethamine, and the like.

Anti-ulcerative agents such as, misoprostol, omeprazole, enprostil, and the like.

Antiulcer agents such as, allantoin, aldioxa, alcloxa, N-methylscopolamine methylsuflate, and the like.

Antidiabetics such as insulin, and the like. Anti-cancer agent such as, cis-platin, actinomycin D, doxorubicin, vincristine, vinblastine, etoposide, amsacrine, mitoxantrone, tenipaside, taxol, colchicine, cyclosporin A, phenothiazines or thioxantheres, and the like.

Other possibilities include those for use with vaccines, one or more antigens, such as, natural, heat-killer, inactivated, synthetic, peptides and even T cell epitopes (e.g., GADE, DAGE, MAGE, etc.), and the like.

Example therapeutic or active agents also include drugs of molecular weight from about 40 to about 1,100 including the following: Hydrocodone, Lexapro, Vicodin, Effexor, Paxil, Wellbutrin, Bextra, Neurontin, Lipitor, Percocet, Oxycodone, Valium, Naproxen, Tramadol, Ambien, Oxycontin, Celebrex, Prednisone, Celexa, Ultracet, Protonix, Soma, Atenolol, Lisinopril, Lortab, Darvocet, Cipro, Levaquin, Ativan, Nexium, Cyclobenzaprine, Ultram, Alprazolam, Trazodone, Norvasc, Biaxin, Codeine, Clonazepam, Toprol, Zithromax, Diovan, Skelaxin, Klonopin, Lorazepam, Depakote, Diazepam, Albuterol, Topamax, Seroquel, Amoxicillin, Ritalin, Methadone, Augmentin, Zetia, Cephalexin, Prevacid, Flexeril, Synthroid, Promethazine, Phentermine, Metformin, Doxycycline, Aspirin, Remeron, Metoprolol, Amitriptyline, Advair, Ibuprofen, Hydrochlorothiazide, Crestor, Acetaminophen, Concerta, Clonidine, Norco, Elavil, Abilify, Risperdal, Mobic, Ranitidine, Lasix, Fluoxetine, Coumadin, Diclofenac, Hydroxyzine, Phenergan, Lamictal, Verapamil, Guaifenesin, Aciphex, Furosemide, Entex, Metronidazole, Carisoprodol, Propoxyphene, Digoxin, Zanaflex, Clindamycin, Trileptal, Buspar, Keflex, Bactrim, Dilantin, Flomax, Benicar, Baclofen, Endocet, Avelox, Lotrel, Inderal, Provigil, Zantac, Fentanyl, Premarin, Penicillin, Claritin, Reglan, Enalapril, Tricor, Methotrexate, Pravachol, Amiodarone, Zelnorm, Erythromycin, Tegretol, Omeprazole, and Meclizine.

Monospecific antibodies, such as monoclonal antibodies and phages, and the like.

Cholinesterase family of enzymes, such as acetalcholinesterase and butyryl acetalcholinesterase, and the like Other active agents include those listed as BCS Class II agents, such as Glibenclamide for example, and the like.

The active agents mentioned above may be used in combination as required. Moreover, the above drugs may be used either in the free form or, if capable of forming salts, in the form of a salt with a suitable acid or base. When the drugs have a carboxyl group, their esters may be employed.

It is contemplated that at least all possible types of dry powder formulations for pulmonary delivery are within the scope of the present disclosure.

This may include, but is not limited to, pure micronized drug formulations, no excipients are included (e.g., drug particles may or may not be crystalline, the formulation may include one or more drugs, co-crystals—multiple APIs in a single crystalline particle); binary, ternary, etc., formulations where the drug is but one component of the formulation, two or more drugs are blended together, and which also may or may not include one or more excipients; and engineered powders including low density powders, spray-dried powder, etc., designed to be dispersed effectively relative to traditional micronized formulations, the PulmoSphere® technology used in the TOBI® Podhaler®. However, the oscillating bead dispersion mechanism as described throughout the present disclosure may be used with other aerosol dispersion methods, not just powders, including but not limited to, aqueous and/or propellant-based inhalers, such as liquid or powder nebulizers, pMDIs and powder or liquid nasal sprays. Still other embodiments are possible.

Further it is contemplated that the dry powder formulations for pulmonary delivery in accordance with the present disclosure may be used to counter effects of various types of agents that may at least initially affect the respiratory system including, but are not limited to: harassing agents such as tear agents and vomiting agents; incapacitating agents such as psychological agents; and lethal agents such as blister agents, blood agents, choking (pulmonary) agents, and nerve agents.

Examples of tear agents may include a-Chlorotoluene, Benzyl bromide, Bromoacetone (BA), Bromobenzylcyanide (CA), Bromomethylethyl ketone, Capsaicin (OC), Chloracetophenone (MACE; CN), Chloromethyl chloroformate, Dibenzoxazepine (CR), Ethyl iodoacetate, Ortho-chlorobenzylidene malononitrile (Super tear gas; CS), Trichloromethyl chloroformate, Xylyl bromide, and the like.

Examples of vomiting agents may include Adamsite (DM), Diphenylchloroarsine (DA), Diphenylcyanoarsine (DC), and the like.

Examples of psychological agents may include 3-Quinuclidinyl benzilate (BZ), Phencyclidine (SN), Lysergic acid diethylamide (K), and the like.

Examples of blister agents may include nitrogen mustards such as Bis(2-chloroethyl)ethylamine (HN1), Bis(2-chloroethyl)methylamine (HN2), Tris(2-chloroethyl)amine (HN3), Sulfur Mustards such as 1,2-Bis(2-chloroethylthio) ethane (Sesquimustard; Q), 1,3-Bis(2-chloroethylthio)-n-propane, 1,4-Bis(2-chloroethylthio)-n-butane, 1,5-Bis(2-chloroethylthio)-n-pentane, 2-Chloroethylchloromethylsulfide, Bis(2-chloroethyl)sulfide (Mustard gas; HD), Bis(2-chloroethylthio) methane, Bis(2-chloroethylthiomethyl)ether, Bis(2-chloroethylthioethyl)ether (O Mustard; T), and the like, and Arsenicals such as Ethyldichloroarsine (ED), Methyldichloroarsine (MD), Phenyldichloroarsine (PD), 2-Chlorovinyldichloroarsine (Lewisite; L), and the like.

Examples of blood agents may include Cyanogen chloride (CK), Hydrogen cyanide (AC), Arsine (SA), and the like.

Examples of choking agents may include but are not limited to, Chlorine (CL); Chloropicrin (PS), Diphosgene (DP), Phosgene (CG), and the like.

Examples of nerve agents may include G series such as Tabun (GA), Sarin (GB), Soman (GD), Cyclosarin (GF), GV series such as Novichok agents, GV (nerve agent), V series such as VE, VG, VM, and the like.

As mentioned above, the example bead 302 disposed within the example chamber 104 may oscillate in a manner similar to that described in U.S. application Ser. No. 13/469,963, filed 11 May 2012, entitled "Bead-Containing Dry Powder Inhaler." However, in accordance with the present disclosure, the bead 302 may not include a pre-coated powder on its surface. Rather, powder may be separately introduced into the chamber 104 from a receptacle such as dose containment or dosing chamber, or other temporary holding compartment or region, or from another dry powder inhaler, as described further below. With this configuration, the powder may be initially placed into a dose containment chamber. When a patient inhales from a mouthpiece, air may be drawn through the dose containment chamber which moves the powder into the chamber 104, where it encounters the bead 302 oscillating primarily along the longitudinal axis L (see e.g., FIG. 3).

In some embodiments, however, the bead 302 may be coated with drug. This may act as a detachment platform for the drug coated on its surface, as well as a dispersion mechanism for drug formulation located and introduced upstream of the bead. For example, for a combination drug product, such as delivering two or more drugs in a single inhalation maneuver, where one drug is delivered in a larger dose, such as an inhaled corticosteroid, than the other drug, such as a long-acting beta-agonist, the lower dose drug may be coated onto the surface of the bead 302, while the larger dose drug is located in a dose containment container, such as a capsule, blister, reservoir, etc., upstream of the chamber 104 containing the drug-coated bead. Thus, during inhalation, oscillation of the bead 302 may serve as a detachment platform to the drug adhered to its surface, and as a dispersion mechanism to the powder that is located upstream.

Additionally, the bead 302 may be coated with a layer of durable material. An example of such a material may include, but is not limited to, gelatin, sugars, any pharmaceutically acceptable film coating materials, including polymers, metallic coatings, anti-static coatings, plasma coatings, etc. This may be beneficial for example when bead material can erode or fragment. In this example, the layer thickness may depend on the density of the material to be added, such that the addition of the coated layer does not eliminate or substantially impair or inhibit the ability of the bead 302 to oscillate within the dispersion chamber 104.

Using the bead 302 as a dispersion mechanism may provide a number of advantages. For example, by employing the oscillating bead in the capacity of a dispersion engine, large doses such as, for example, about 1 mg to about 25 mg or greater, may be delivered by storing them in capsules or blisters. However, it will be appreciated that smaller doses may also be delivered. For example, doses greater than about 1 µg of active drug may be delivered. In some cases, the active drug may be blended with a carrier, such as lactose. Also, when the bead 302 is not coated with drug and used as a dispersion mechanism, there is no retention mechanism required to hold the bead 302 tightly within the inhaler, decreasing the complexity of the DPF. Still further, using the bead 302 as a dispersion mechanism may require no additional or complicated processing steps for the DPF formulations, as the powder may be produced by traditionally employed methods. Additionally, the bead 302 in the present disclosure may oscillate generally within the center of the chamber 104, along the longitudinal axis L, where physical contact between the bead 302 and inner walls of the chamber 104, and possibly ends of the chamber 104, may occur infrequently, if at all. This type of dispersion mechanism may be beneficial as collisions between walls of the chamber 104 and the bead 302 could serve to rub powder onto either the surface of the bead 302 or inner walls of the chamber 104 when powder is caught therebetween during a physical collision, thereby decreasing an amount of powder available for transfer into the lungs of a patient. Alternatively the frequent collision of the bead 302 with the walls of the chamber 104 may act to scrub off any drug adhered to the wall(s), thus increasing an amount of powder available for transfer into the lungs of a patient.

Referring now back to FIGS. 1-3, and as mentioned above, alignment of the inlet 102 and the chamber 104, may provide significant advantages over inhalers having an "off-axis" alignment. In particular, the tubular body 100 of the present disclosure may produce an approximately symmetrical flow stream expansion that drives oscillation of the bead 302. Such a configuration may enable a powder dispersion device, or dry powder inhaler, incorporating aspects of the tubular body 100, to be constructed with minimal bulk. For example, the chamber 104 in example embodiments of the present disclosure may be modeled as a cylinder of the dimensions detailed above (e.g., $d_{chamber}$~7.37 mm, $l_{chamber}$~10 mm) for a similar 5 mm bead. Accordingly, a maximum volume occupied by the chamber 104 is about 427 cubic mm based on the expression $v_{cylinder}=\pi r^2 l$.

Figure 4:
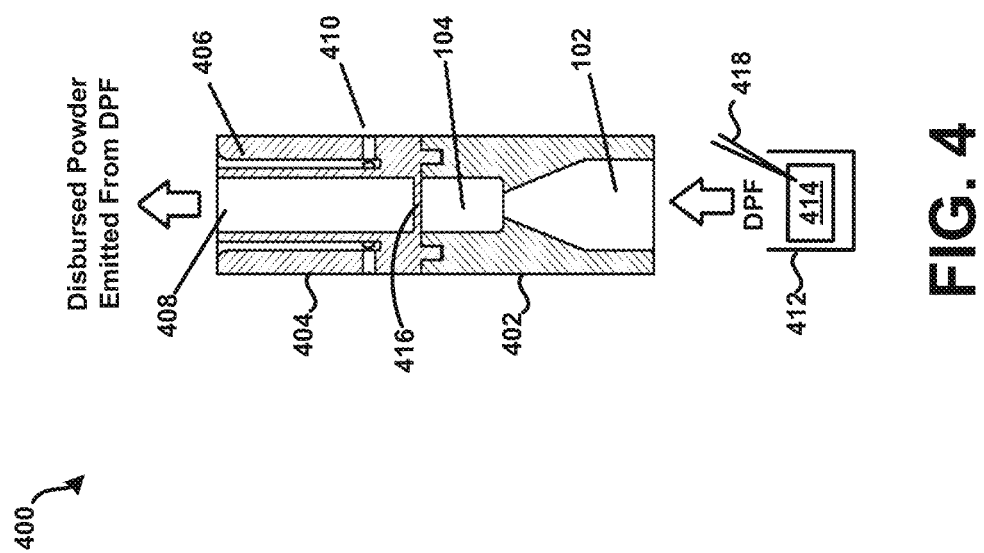
FIG. 4 shows a first view of an example powder dispersion device in cross-section.
Figure 5:
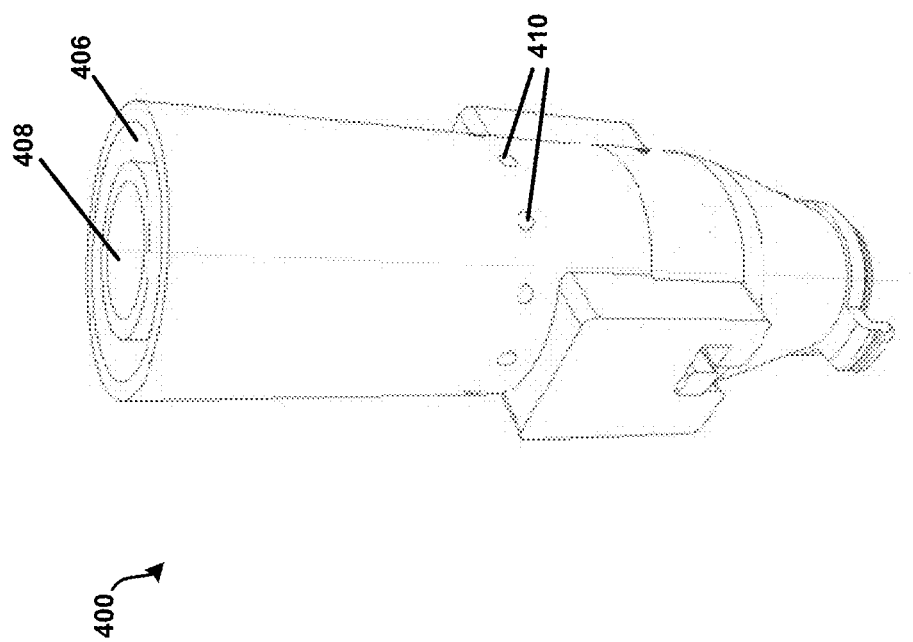
FIG. 5 shows a perspective view of the device of FIG. 4.

Referring now to FIGS. 4-5, an example powder dispersion device or inhaler 400 is shown in accordance with the principles of the present disclosure. In particular, FIG. 4 shows a first view of the device 400 of FIG. 4 in cross-section. FIG. 5 shows a perspective view of the device 400 of FIG. 4.

The device 400 may generally incorporate aspects of the example tubular body 100 described above in connection with FIGS. 1-3. For example, the device 400 may include a first housing 402 comprising the inlet 102 and the chamber 104 of the tubular body 100. Additionally, although not expressly shown, the bead 302 may be positioned within the chamber 104, such as shown in FIG. 3. The device 400 may further include a second housing 404 comprising a sheath flow channel 406 that surrounds and is not in fluid connection with a primary or main powder flow channel 408. In some embodiments, the first housing 402 may be integrally formed with the second housing 404. In one embodiment, the chamber 104 and the main powder flow channel 408 may have at least one common structural dimension, such as internal diameter for example. Additionally, the second housing 404 may itself comprise of, be coupled to, or otherwise incorporated within, a mouthpiece adapted to be placed within the mouth of a patient, or in a nasal adapter adapted to conform to the nostrils of a patient. The device 400 may further include a plurality of flow bypass channels 410 that are formed within the second housing 404. The flow bypass channels 410 may be in fluid connection with the sheath flow channel 406.

The device 400 may further include a dosing chamber 412, a retaining member 416, and a piercing member 418 disposed at an end of the chamber opposite the inlet 102. The piercing member 418 may puncture or otherwise perforate a capsule, blister, or powder reservoir 414 as arranged or positioned within the dosing chamber 412. In general, the retaining member 416 may include at least one opening or aperture sized to permit air and powdered or otherwise aerosolized medicament to pass through the retaining member 416, and to prevent the possibility of the bead 302 from exiting the chamber 104. The at least one opening or aperture may, in some embodiments, be arranged and configured (e.g., diameter, pattern, etc.) to maintain desired fluid flow characteristics with the device 400, such that the bead 302 may disrupt and aerosolize medicament powder agglomerates within the chamber 104 to provide for more effective deposition of medicament into the lungs of a patient.

In one example, referring specifically to FIG. 4, a patient may prime the device 400 by puncturing the capsule, blister, or transfer of a dose from a powder reservoir 414, and then inhale, drawing air through the chamber 104 which in turn draws the DPF from the dosing chamber 412 into the adjacent chamber 104 via the inlet 102, where the bead 302 is rapidly oscillating, creating high-energy forces that may strip drug from the surface of carrier particles in the DPF, or when the bead 302 is drug-covered, and/or de-agglomerate drug powder aggregates and drug-on-drug aggregates. Drug particles may then be deposited in lungs and airways of a patient from the primary or main powder flow channel 408 based on direction of air flow through the device such as shown in FIG. 4. Such a "self-dosing" scenario may be useful for effectively dispensing both traditional binary or ternary DPF formulations, drug and carrier/excipient particles, and pure drug-powder formulations where there are no carrier particles are present. Other embodiments having similar effects are possible, as discussed further below in connection with FIG. 9.

In general, the resistance to flow of the device 400 may be adjusted by altering the geometry and/or arrangement of at least one of the inlet 102, the bead 302, the sheath flow channel 406, the main powder flow channel 408, and the flow bypass channel(s) 410. Additionally, as shown in FIG. 5, the flow bypass channels 410 may be located radially around the body of the second housing 404, and fluidly connected to the sheath flow channel 406. In some embodiments however, the device 400 may not include any flow bypass channels. In one embodiment, the flow bypass channels 410 may comprise of twelve individual channels located radially around the body of the second housing 404. However, other embodiments are possible. For example, the flow bypass channels 410 may comprise of different numbers and diameters of individual channels and entry points into the sheath flow channel 406. Further, one or more of the flow bypass channels 410 may be parallel through the main powder flow channel 408, or may be in fluid connection with, and then diverge from, the main powder flow channel 408. Still other embodiments are possible.

One or more of the flow bypass channels 410 may be "opened" or "closed" such as by removal or insertion of a resilient material therein to "unplug" or "plug" the same. This may result in changes in the overall resistance of the device 400, thereby influencing flow rate through the device 400. For example, a person may inhale through a "high" resistance inhaler with a lower inspiratory flow rate than they would through a "low" resistance inhaler, despite inhaling with the same inhalation effort. In this manner, the device 400 may be "tuned" to respond "optimally" to the needs of a patient. In other words, the device 400 in accordance with the present disclosure may be tailored to suit particular patient needs. For example, resistance of the device 400 may be approximately inversely proportional to diameter of the bead 302. Thus, for a "larger" diameter bead 302, one or more of the flow bypass channels 410 may be "closed" to increase resistance of the device such that a patient may receive a proper dose of medicament irrespective of possibly diminished inhalation capacity.

Experimental Study A

Performance of the example powder dispersion device or inhaler 400 of FIG. 4 was evaluated to assess how the bead 302 as an oscillating mechanism functions to disperse drug powder within the chamber 104. In this example, no powder was coated onto the surface of the bead 302. During inhalation, powder travels from a dosing chamber 412 (see FIG. 4), where the powder is stored, into the chamber 104, where the bead 302 when oscillating creates high-energy forces that may strip the drug particles from, for example, a lactose carrier, and/or disrupt aggregated particles and disperse them into sizes that may more easily penetrate patient airways. Additionally, physical collisions between the bead 302 and coarse "carrier" particles and/or aggregates may also promote drug dispersion, and increased physical collisions between lactose carrier particles.

In general, the bead 302 may comprise of an uncoated "low" density expanded polystyrene bead, with the chamber 104 being downstream of the dosing chamber 412, where the powder may be contained in the powder reservoir 414. Other embodiments are possible. For example, a density of the bead 302 may be selected as desired, where the density of bead 302 may or may not affect performance of the device 400. In the example of a capsule, capsule material may include gelatin or HPMC (hydroxypropylmethylcellulose). Examples of commercial dry powder inhaler products where the powder is stored in capsules include the FORADIL® Aerolizer® and the SPIRIVA® HandiHaler®. In general, the capsules may each contain one dose, or multiple capsules can be used to contain the equivalent of one dose, as with the TOBI® Podhaler®, where each dose consists of four capsules, each containing 28 mg of powder for example. In the example of an individual blister, one blister may contain one dose. Examples of commercial dry powder inhaler products where the powder is stored in blisters include the FLOVENT® Diskus®, SEREVENT® Diskus®, and the ADVAIR® Diskus®. In the example of a reservoir, a particular reservoir may contains sufficient powder for multiple doses. Examples of commercial dry powder inhaler products where the powder is stored in reservoirs include the ASMANEX® Twisthaler®, SYMBICORT® Turbuhaler® and the Budelin® Novolizer®. Still other embodiments are possible.

In practice, a patient may prime the device 400 by puncturing the capsule/blister contained within the powder reservoir 414 or transferring drug from the powder reservoir 414, and then inhale, drawing powder into the adjacent chamber 104 via the inlet 102 where the bead 302 is rapidly oscillating, creating high-energy forces that may strip the drug from the surface of carrier particles (e.g., when the bead 302 is drug-covered), and/or de-agglomerate powder aggregates. Thus, this approach may be useful for effectively dispersing both traditional binary or ternary DPF formulations, drug and carrier/excipient particles, and pure drug-powder formulations where there are no carrier particles are present.

In the example study, the capsule chamber of the Handihaler® (see e.g., FIG. 6) as described generally in U.S. Pat. No. 7,252,087, was employed to puncture an HPMC capsule containing 20 mg (±1 mg) of a 2% binary blend of micronized budesonide and inhalation-grade lactose (Respitose® ML006). As a control, the powder was dispersed only from the Handihaler®, with no bead-dispersion chamber downstream. For the experimental sets, the chamber 104 was included downstream of the Handihaler® capsule chamber with a single 4 mm expanded polystyrene bead, placed inside. Thus the experimental configurations were: Handihaler® alone (herein referred to as "No Attachment"); and Handihaler® with the example device 400 as an attachment (herein referred to as "Attachment").

Due to placing of "narrow" inlets in series, the resistance of the "Attachment" was relatively "high," with a 4 kPa pressure drop of approximately 26 LPM. In this example, the flow bypass channels 410 of the device 400 were used to lower the resistance, making the 4 kPa pressure drop flow rate at approximately 70 LPM; the cutoff of Stage 2 is about 4.1 μm, and the cutoff of Stage 1 is about 7.4 μm. The Stage 2 cutoff of 39 LPM is about 5.6 μm.

The results with N=3 (+/−stdev):

"No Attachment": FPF (Fine Particle Fraction) (<5.6 μm)=48.2% (3.0%); and

"Attachment": FPF (<4.1 μm)=70.9% (1.2%).

Here, it may be understood that the FPF increased at Stage 2 cutoff from 48.2%, using the "No Attachment" arrangement or configuration, to 70.9%, using the "Attachment" arrangement or configuration. Thus, it may be understood that the "Attachment" arrangement or configuration more efficiently deaggregated powder passing through arrangement or configuration, such that a greater percentage of "smaller" particles were created that would then be available to penetrate into a patients lung.

Additionally, when Stage 2 was also included in the FPF, changing the cutoff size to <about 7.4 μm), the FPF would increase to 77.7% (1.0%).

It was expected there would be significant drop-off in measurable or otherwise recovered dose due to loss in the chamber 104. There was however no noticeable difference in recovered dose. This surprising and unexpected result may indicate that the device 400, a compact device, having straight powder flow path containing a breath-actuated, approximately linearly oscillating, bead as the dispersion mechanism, may serve as an effective powder dispersion mechanism for at least dry powder formulations. This may be beneficial in many respects. For example, since it has been found that FPF output increases using the "Attachment" arrangement or configuration, a patient may be more capable of obtaining a proper dosage of medicament. Other benefits are possible as well.

Experimental Study B

Performance of the example powder dispersion device or inhaler 400 of FIG. 4 was evaluated to assess the influence of size of the bead 302 on the example device 400. In this example, a particular powder dispersion device configured to incorporate a bead of a particular size was produced via stereolithography from the material DSM Somos® NeXT. A particular powder dispersion device was attached to the capsule chamber of the HandiHaler® dry powder inhaler. This allowed testing the dispersion of powder from capsules that could be perforated by the piercing mechanism of the HandiHaler®.

Figure 6:
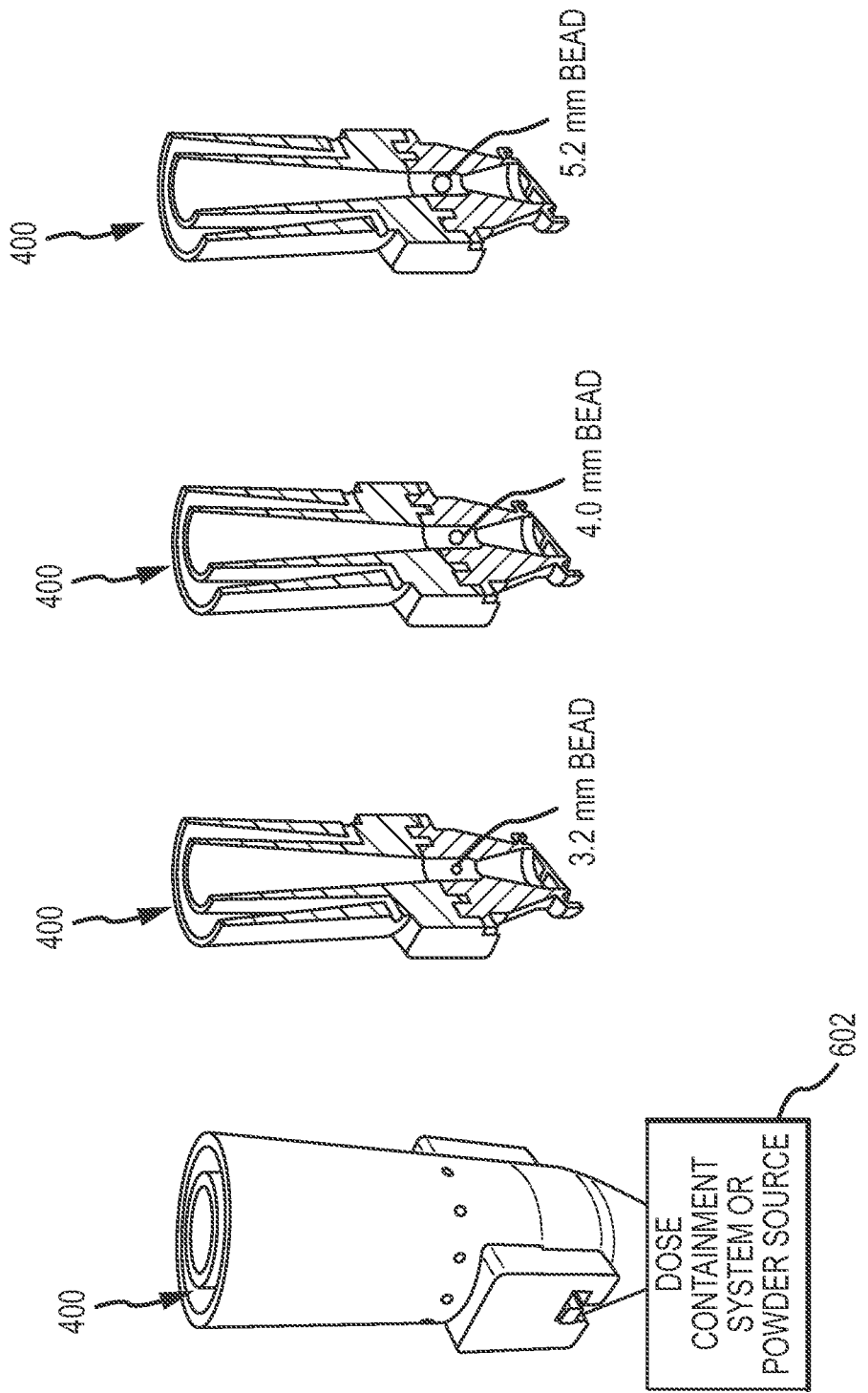
FIG. 6 shows a first example experimental set-up in accordance with the present disclosure.

FIG. 6 shows a first example experimental set-up in accordance with the present disclosure. In particular, FIG. 6 shows the example device 400 of FIG. 4 attached to a capsule chamber (e.g., dosing chamber 412) of the Handi-Haler® dry powder inhaler 602. Although, it will be appreciated that element 602 may generally be any type of dose containment system or powder source. FIG. 6 further shows the device 400 arranged and configured to incorporate or otherwise exhibit a 3.2 mm bead, a 4.0 mm bead, and a 5.2 mm bead. Powder contained in a capsule was punctured using the piercing mechanism of the HandiHaler® dry powder inhaler. During inhalation, powder is pulled or otherwise caused to flow out from the perforations in the capsule wall, traveling into the chamber 104 of the device 400, where forces created by the bead 302, when the bead is rapidly oscillating, at least disrupts powder agglomerates.

In general, the resistance of the device 400 varied inversely with bead size. The device 400 was tested at a constant 4 kPa pressure drop across the device 400 by altering the volumetric flow rate through the device 400 to compensate for difference in device resistance, summarized in the following Table 1:

| Configuration | Bead Size | 4 kPa Flow Rate | Device Resistance $(cmH_2O)^{0.5}/L\ min^{-1}$ |
|---|---|---|---|
| No Attachment | No Attachment | 39 L min$^{-1}$ | 0.173 |
| Attachment | 3.2 mm | 81 L min$^{-1}$ | 0.079 |
| Attachment | 4.0 mm | 86 L min$^{-1}$ | 0.073 |
| Attachment | 5.2 mm | 95 L min$^{-1}$ | 0.069 |

Here, it may be understood that even though an "Attachment" in accordance with the present disclosure is being coupled to an inhaler, device resistance including the "Attachment" does not increase. Rather, device resistance decreases. This may be beneficial in many respects. For example, a patient with decreased or otherwise diminished lung capacity may be more capable of using the "Attachment" arrangement or configuration. Further, since it has been found that FPF output increases using the "Attachment" arrangement or configuration (see Experimental Study A), a patient of decreased or otherwise diminished lung capacity may be more capable of obtaining a proper dosage of medicament. Other benefits are possible as well.

Experimental Study B1

Performance of the example powder dispersion device or inhaler 400 of FIG. 4 was evaluated to assess the influence of size of the bead 302 in delivering a high dose of a pure micronized beta agonist, not containing any excipients.

In this example study, 15 mg (±1 mg) of pure micronized albuterol sulfate (beta-agonist) was placed into Size 3 HPMC capsules. Powder was dispersed via the "No Attachment" or "Attachment" configurations as discussed above, with the device 400 including either a 3.2 mm bead, 4.0 mm bead, or 5.2 mm bead, and attached to the capsule chamber of the HandiHaler® dry powder inhaler 602 (see FIG. 6) through a next generation cascade impactor connected to a high vacuum pump. The volumetric flow rate through the different configurations was adjusted such that a pressure drop of approximately 4 kPa was produced across the respective device 400, such as listed in Table 1 above. The devices were activated or otherwise actuated for a time interval that allowed 4 L of air to flow therethrough. Following actuation, the drug depositing on the different regions of the experimental setup was collected by rinsing each region with deionized water, and quantified by UV-VIS spectrophotometry at 230 nm.

The FPF of the emitted dose, which may refer to the fraction of a dose that leaves the inhaler that deposits in the lungs, because if its size, for each configuration is summarized in the following Table 2:

| Configuration/Bead Size | FPF (emitted), N = 3 |
|---|---|
| No Attachment | 24.1% (3.4 +/− 1 std deviation) |
| Attachment/3.2 mm bead | 75.3% (2.9 +/− 1 std deviation) |
| Attachment/4.0 mm bead | 75.8% (3.1 +/− 1 std deviation) |
| Attachment/5.2 mm bead | 73.0% (5.5 +/− 1 std deviation) |

Here, it may be understood that the FPF increased from about 24%, using the "No Attachment" arrangement or configuration, to between about 73% to 76%, using the "Attachment" arrangement or configuration. Similar to the above-conclusion (see Experimental Study A), it may be understood that the "Attachment" arrangement or configuration more efficiently deaggregated powder passing through arrangement or configuration, such that a greater percentage of "smaller" particles were created that would then be available to penetrate into a patients lung.

Experimental Study B2

Performance of the example powder dispersion device or inhaler 400 of FIG. 4 was evaluated to assess the influence of size of the bead 302 in delivering a high dose of a pure inhaled corticosteroid, no excipients.

In this example study, 10 mg (±0.5 mg) of pure micronized mometasone furoate (inhaled corticosteroid) was placed into Size 3 HPMC capsules. Powder was dispersed via the "No Attachment" or "Attachment" configuration as discussed above, with the device 400 including either a 3.2 mm bead or 5.2 mm bead, and attached to the capsule chamber of the HandiHaler® dry powder inhaler 602 (see FIG. 6) through a next generation cascade impactor connected to a high vacuum pump. The volumetric flow rate through the different configurations was adjusted such that a pressure drop of approximately 4 kPa was produced across the respective device 400, such as listed in Table 1 above. The devices were actuated for a time interval that allowed 4 L of air to flow through the inhaler. Following actuation, the drug depositing on the different regions of the experimental setup was collected by rinsing each region with methanol and quantified by UV-VIS spectrophotometry at 250 nm. Other preferred solvents may be used depending on type of studied drug.

The FPF of the emitted dose for each configuration is summarized in the following Table 3:

| Device Configuration/Bead Size | FPF (emitted), N = 3 |
| --- | --- |
| No Attachment | 31.5% (4.0 +/− 1 std deviation) |
| Attachment/3.2 mm bead | 75.6% (2.8 +/− 1 std deviation) |
| Attachment/5.2 mm bead | 70.3% (1.7 +/− 1 std deviation) |

Here, it may be understood that the FPF increased from about 32%, using the "No Attachment" arrangement or configuration, to between about 70% to 76%, using the "Attachment" arrangement or configuration. Similar to the above-conclusion (see Experimental Study A), it may be understood that the "Attachment" arrangement or configuration more efficiently deaggregated powder passing through arrangement or configuration, such that a greater percentage of "smaller" particles were created that would then be available to penetrate into a patients lung.

Experimental Study B3

Performance of the example powder dispersion device or inhaler 400 of FIG. 4 was evaluated to assess the influence of size of the bead 302 in delivering a low dose of beta-agonist delivered from a traditional DPF formulation, with coarse lactose particles as an excipient.

In this example study, a 2% (w/w) binary blend of albuterol sulfate in lactose was prepared by blending 490 mg of inhalation-grade lactose (LactoHale 300) with 10 mg of pure micronized albuterol sulfate via geometric dilution in a 25 mL glass scintillation vial. The vial was then placed into a Turbula® Orbital blender for 40 minutes at 46 RPM. 20 mg (±1 mg) of the 2% albuterol sulfate blend was placed into Size 3 HPMC capsules. Powder was dispersed via the "No Attachment" or "Attachment" configuration as discussed above, with the device 400 including either a 3.2 mm bead, a 4.0 mm bead, or 5.2 mm bead, and attached to the capsule chamber of the HandiHaler® dry powder inhaler 602 (see FIG. 6) through a next generation cascade impactor connected to a high vacuum pump. The volumetric flow rate through the different configurations was adjusted such that a pressure drop of approximately 4 kPa was produced across the respective device 400, such as listed in Table 1 above. The devices were actuated for a time interval that allowed 4 L of air to flow through the inhaler. Following actuation, the drug depositing on the different regions of the experimental setup was collected by rinsing each region with deionized H$_2$O and quantified by UV-VIS spectrophotometry at 230 nm.

The fine particle fraction of the emitted dose for each configuration is summarized in the following Table 4:

| Device Configuration/Bead Size | FPF (emitted), N = 3 |
| --- | --- |
| No Attachment | 29.7% (2.8 +/− 1 std deviation) |
| Attachment/3.2 mm bead | 72.7% (0.9 +/− 1 std deviation) |
| Attachment/4.0 mm bead | 71.8% (2.6 +/− 1 std deviation) |
| Attachment/5.2 mm bead | 71.6% (4.3 +/− 1 std deviation) |

Here, it may be understood that the FPF increased from about 30%, using the "No Attachment" arrangement or configuration, to between about 72% to 73%, using the "Attachment" arrangement or configuration. Similar to the above-conclusion (see Experimental Study A), it may be understood that the "Attachment" arrangement or configuration more efficiently deaggregated powder passing through arrangement or configuration, such that a greater percentage of "smaller" particles were created that would then be available to penetrate into a patients lung.

Experimental Study C

To evaluate the influence of drug dose on the powder dispersion performance of the device 400, powder was dispersed via the "Attachment" configuration as discussed above, with the device 400 including a 3.2 mm bead, and attached to the capsule chamber of the HandiHaler® dry powder inhaler 602 (see FIG. 6) through a next generation cascade impactor connected to a high vacuum pump. In particular, 1, 5, 10 or 25 mg of pure micronized albuterol sulfate were dispersed with volumetric flow rate set to produce a 4 kPa pressure across the device 400, about 81 LPM. The device 400 was actuated for a time period to allow 4 L of air to flow through the device 400. Samples were rinsed with deionized H$_2$O and analyzed via UV-VIS Spectroscopy at 230 nm. Results showed that the drug delivery efficiency as measured by FPF of the emitted dose was both "high" and relatively consistent, even as the dose increased to 25 mg of pure micronized drug powder, summarized in the following Table 5:

| Device Configuration/Bead Size | Dose | FPF (emitted), N =3 |
| --- | --- | --- |
| Attachment/3.2 mm bead | 1 mg | 83.7% (2.0 +/− 1 std deviation) |
| Attachment/3.2 mm bead | 5 mg | 85.4% (2.8 +/− 1 std deviation) |
| Attachment/3.2 mm bead | 10 mg | 83.7% (2.6 +/− 1 std deviation) |
| Attachment/3.2 mm bead | 25 mg | 78.0% (1.9 +/− 1 std deviation) |

For a bead of approximately equal density, changing the bead diameter will change the bead mass. It is contemplated that beads of lower mass may oscillate with greater frequency than heavier beads. Thus, smaller beads may have a greater oscillation frequency than larger beads. It is contemplated that particle size distributions differ between bead sizes, and with smaller beads, due to the greater oscillation frequency of the smaller beads, higher energy localized eddies may be produced, which may be more effective at de-aggregating powder particles than lower energy localized eddies produced by larger beads that oscillate with a lower frequency. However, larger beads may travel a greater distance during their oscillation, by the power law relation governing bead diameter described above, and coupled with the greater diameter, may displace a larger volume of air when they move. Accordingly, overall force produced by a larger bead may be much greater than that produced by a smaller bead, despite the higher energy eddies produced by the smaller beads, such that a larger bead may influence a greater proportion of powder passing through the dispersion chamber 104, but to a lesser extent than the smaller beads. This may be summarized as: smaller beads→greater oscillation frequency→more effective dispersion, influences less powder; and larger beads→lower oscillation frequency→less effective dispersion, influence more powder. The above description may be one possible explanation as to the operation of the device 400 in accordance with the present disclosure and other mechanisms of action may be possible.

Figure 7:
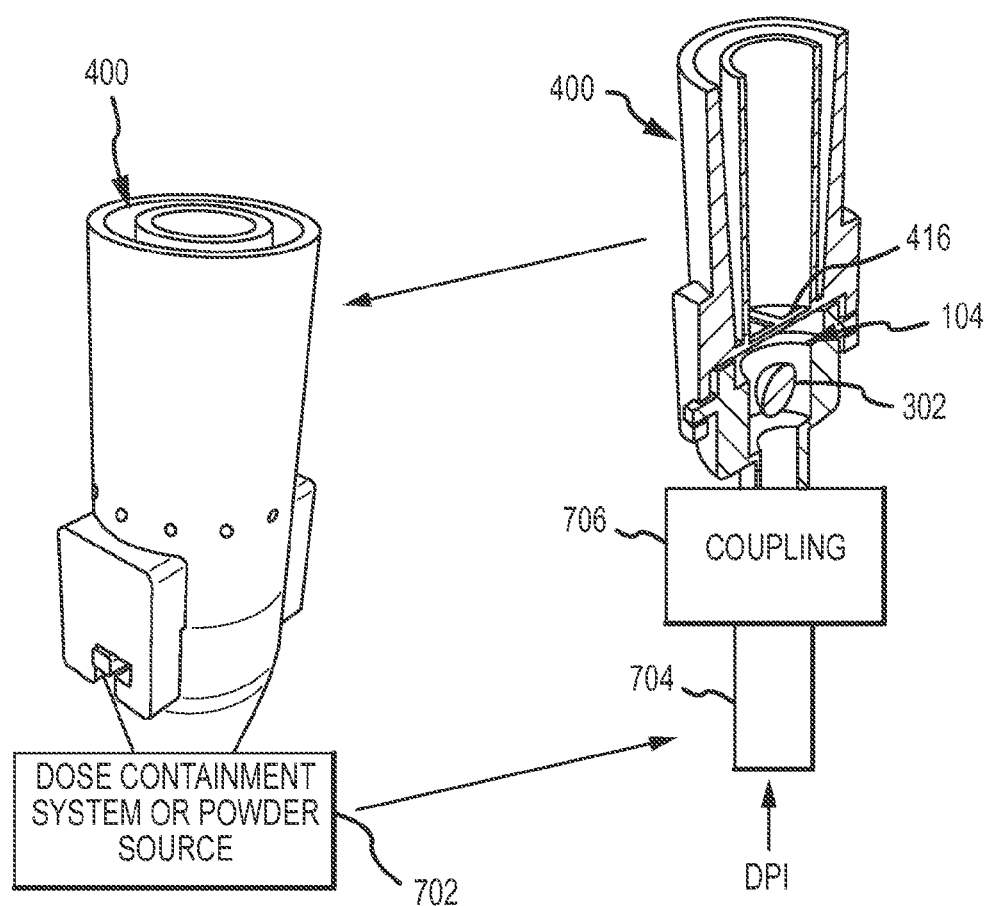
FIG. 7 shows a second example experimental set-up in accordance with the present disclosure.

Referring now to FIG. 7, a second example experimental set-up is shown in accordance with the present disclosure. In particular, FIG. 7 shows the example device 400 of FIG. 4 attached to a mouthpiece 704 of a particular commercial dry powder inhaler 702, namely the Flovent® Diskus® inhaler. Although, it will be appreciated that element 702 may generally be any type of dose containment system or powder source In previous examples, the device 400 was connected directly to the capsule chamber of the HandiHaler®, bypassing the mouthpiece of the HandiHaler®, which powder may flow through under "normal" operation. In contrast, as shown in FIG. 7, the example device 400 of FIG. 4 is coupled to the mouthpiece 704 of the inhaler 702 by a coupling 706, thereby allowing powder to flow through the inhaler 702 as during "normal" operation, and then into the chamber 304 containing the bead 302 (see e.g., FIG. 3). During inhalation, powder is pulled or otherwise caused to flow out through the inhaler 702, traveling into the chamber 104 of the device 400, where forces created by the bead 302, as rapidly oscillating, at least disrupts powder agglomerates.

Experimental Study D

Performance of the example powder dispersion device or inhaler 400 of FIG. 4 was evaluated to assess the ability of the example device 400 in increasing FPD (Fine Particle Dose) and emitted FPF (Fine Particle Fraction) when coupled in series with the inhaler 702. The fraction of a dose that leaves the inhaler that deposits in the lungs, because of its size, may be referred to as the (FPF), or FPD when expressed in terms of mass. In particular, flow rate through the inhaler 702, with API (Active Pharmaceutical Ingredient) Fluticasone propionate, with and without the example device 400 coupled to the mouthpiece 704 was set to produce a 4 kPa pressure drop across the device 400 of 49 LPM when coupled to the inhaler 702 (referred to as "No Attachment"), and 83 LPM when decoupled from the inhaler 702 (referred to as "Attachment"). Samples were collected via rinsing with ethanol and analyzed by UV-VIS spectrophotometer at 238 nm. The example device 400 when coupled in series with the inhaler 702 improved the FPD by 33 mcg (49%), and improved FPF by 52%, summarized in the following Table 6:

| Device Configuration | Fine Particle Dose, N = 5 | FPF (emitted), N = 5 |
| --- | --- | --- |
| No Attachment | 68.2 (2.7) mcg | 26.4% (1.0 +/− 1 std deviation) |
| Attachment | 101.5 (4.3) mcg | 40.0% (1.4 +/− 1 std deviation) |

Here, it may be understood that the device or inhaler 400 of FIG. 4 may enhance the performance (FPF emitted) of a commercial inhaler. This may be beneficial since the device or inhaler 400 of FIG. 4 may be considered as an "add-on," such that a patient may not be required to purchase another device when a particular commercial inhaler does not provide the performance required or desired by the patient. This may be because the device or inhaler 400 of FIG. 4 is configured to more efficiently break-up powder agglomerates, and reduce or otherwise minimize the resistance of an or other device that the device or inhaler 400 is coupled to. Other benefits are possible as well.

Figure 8:
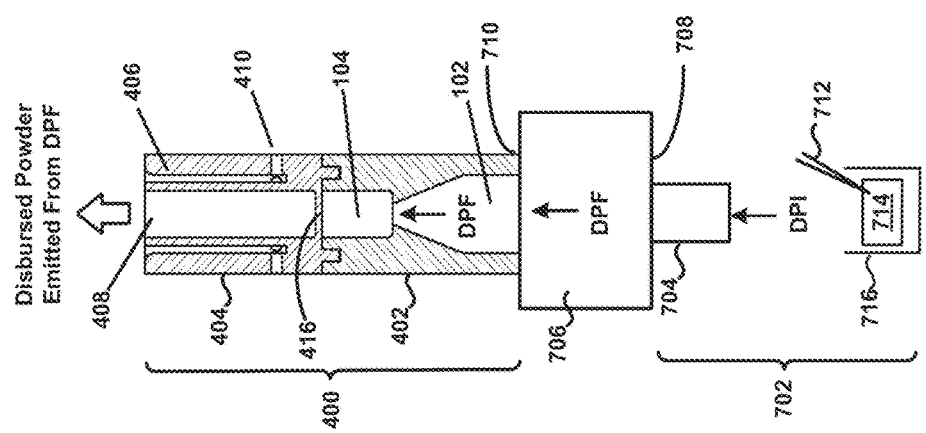
FIG. 8 shows a second view of the device of FIG. 4 in cross-section.

Referring now to FIG. 8, a second view of the device 400 of FIG. 4 is shown in cross-section. In particular, a cross section of the second example experimental set-up of FIG. 7 is shown. Similar to FIG. 7, the example device 400 of FIG. 4 is coupled to the mouthpiece 704 of the inhaler 702 by the coupling 706, thereby allowing powder to flow through the inhaler 702 as during "normal" operation, and then into the chamber 304 containing the bead 302 (see also FIG. 3). In particular, a piercing member 712 may puncture or otherwise perforate a capsule, blister, or powder reservoir 714 as contained within a dosing chamber 716 of the inhaler 702. Powder may then be caused to flow through the inhaler 702 into the chamber 304 containing the bead 302 via the mouthpiece 704 and coupling 706. The bead 302 may then disrupt and aerosolize medicament powder agglomerates within the chamber 104 to provide for more effective deposition of medicament into the lungs of a patient in a manner such as described above. Other embodiments are possible.

In general, the coupling 706 may be a rigid or flexible coupling formed of any material, or combination thereof, such as thermoplastic/thermosetting plastics, metals, glasses, elastomers, etc., and may be coupled to the mouthpiece 704 of the inhaler 702 on a first end 708, and to the device 400 on a second end 710. Here, it may be preferred that the material has surface properties that do not attract powder particles. The coupling 706 may be permanently fastened to, such as being integrally formed therewith, at least one of the inhaler 702 and the device 400, or may be removable fastened with least one of the inhaler 702 and the device 400. For example, the coupling 706 may be fastened to the inhaler 702 by one of a "snap-fit" or a "pressure-fit" or a "twist-to-fit" mechanism, etc., such as in a "quick" connect/disconnect implementation. Still other embodiments are possible. For example, it will be appreciated that the device 400 may not be limited to being "clipped" or otherwise "coupled" to other inhalers. Further, aspects of the present disclosure may be used in combination with any type of dose containment system, and may not be limited to a capsule, blister, or reservoir.

As discussed above in connection with FIG. 4, a patient may prime the device 400 by puncturing the capsule, blister, or powder reservoir 414, and then inhale, drawing the powder from the dosing chamber 412 into the adjacent chamber 104 via the inlet 102, where the bead 302 is rapidly oscillating, creating high-energy forces that may strip drug from the surface of carrier particles (e.g., when the bead 302 is drug-covered), and/or de-agglomerate powder aggregates. Drug particles may then be deposited in lungs and airways of a patient from the primary or main powder flow channel 408 based on direction of air flow through the device such as shown in FIG. 4. Such a "self-dosing" scenario may at least be useful for effectively dispensing both traditional binary or ternary DPF formulations, drug and carrier/excipient particles, and pure drug-powder formulations where there are no carrier particles are present. Other embodiments are however possible.

Figure 9:
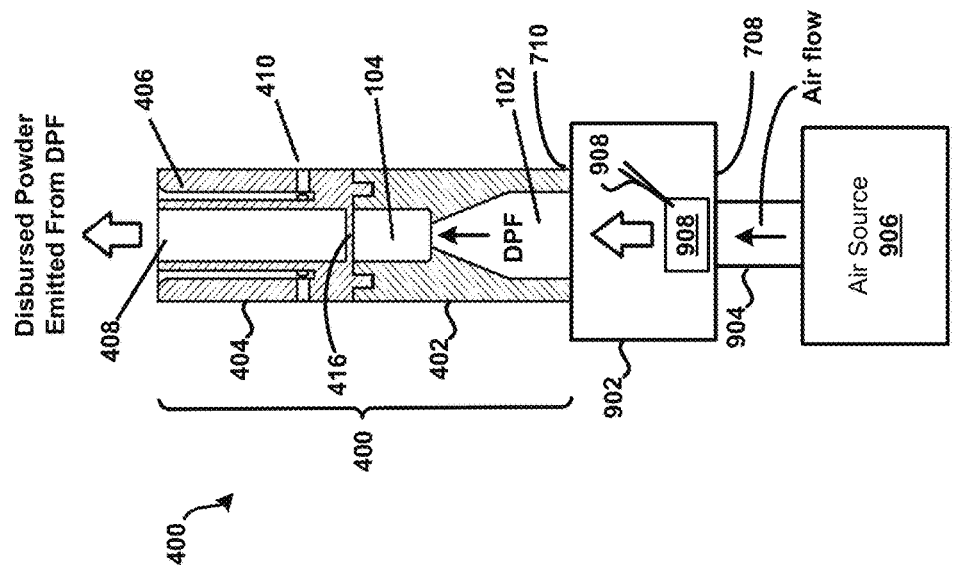
FIG. 9 shows a third view of the device of FIG. 4 in cross-section.
Figure 11:
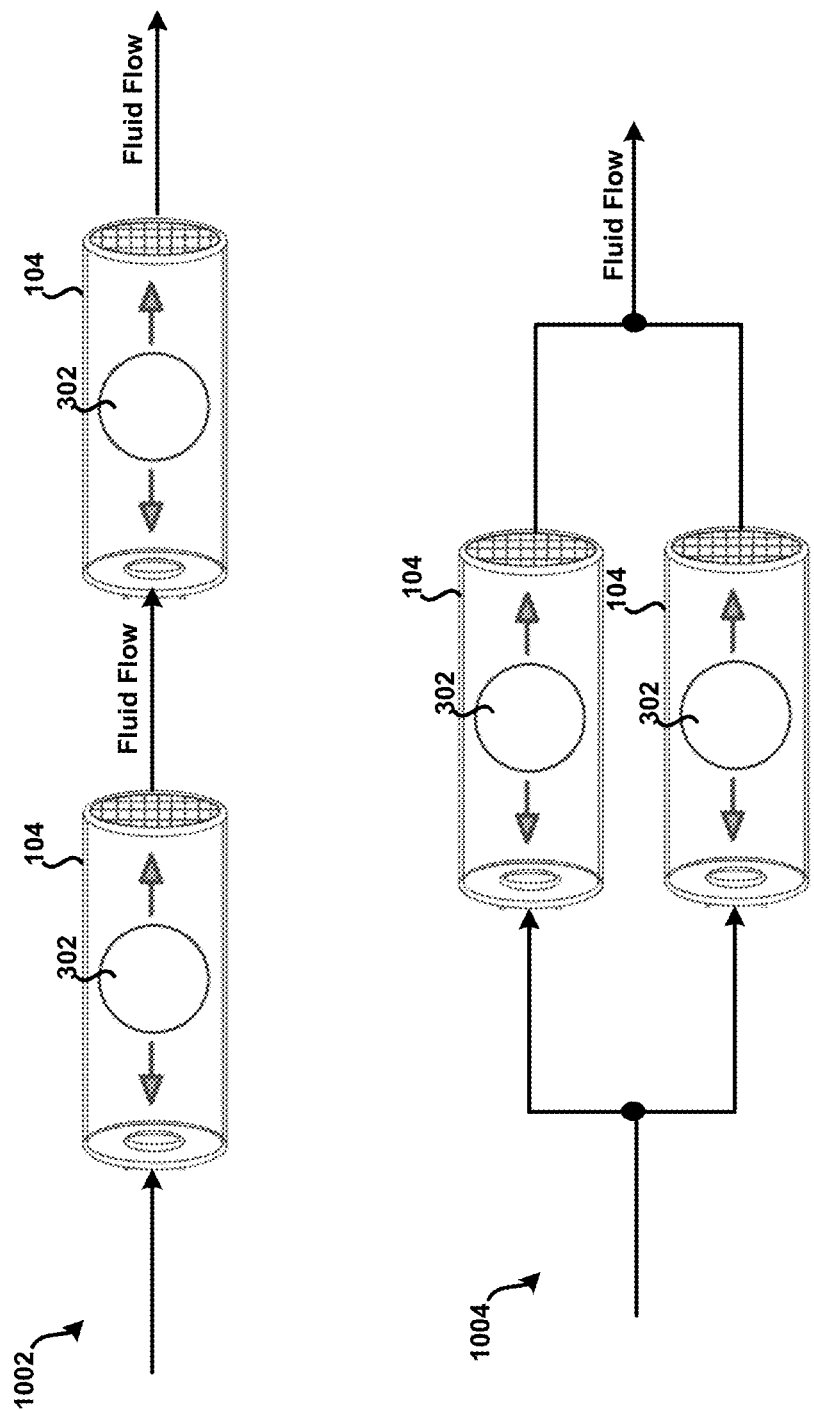
FIG. 11 shows a simplified, conceptual, example schematic diagram of the device of FIG. 4 in multiple configurations.
Figure 12:
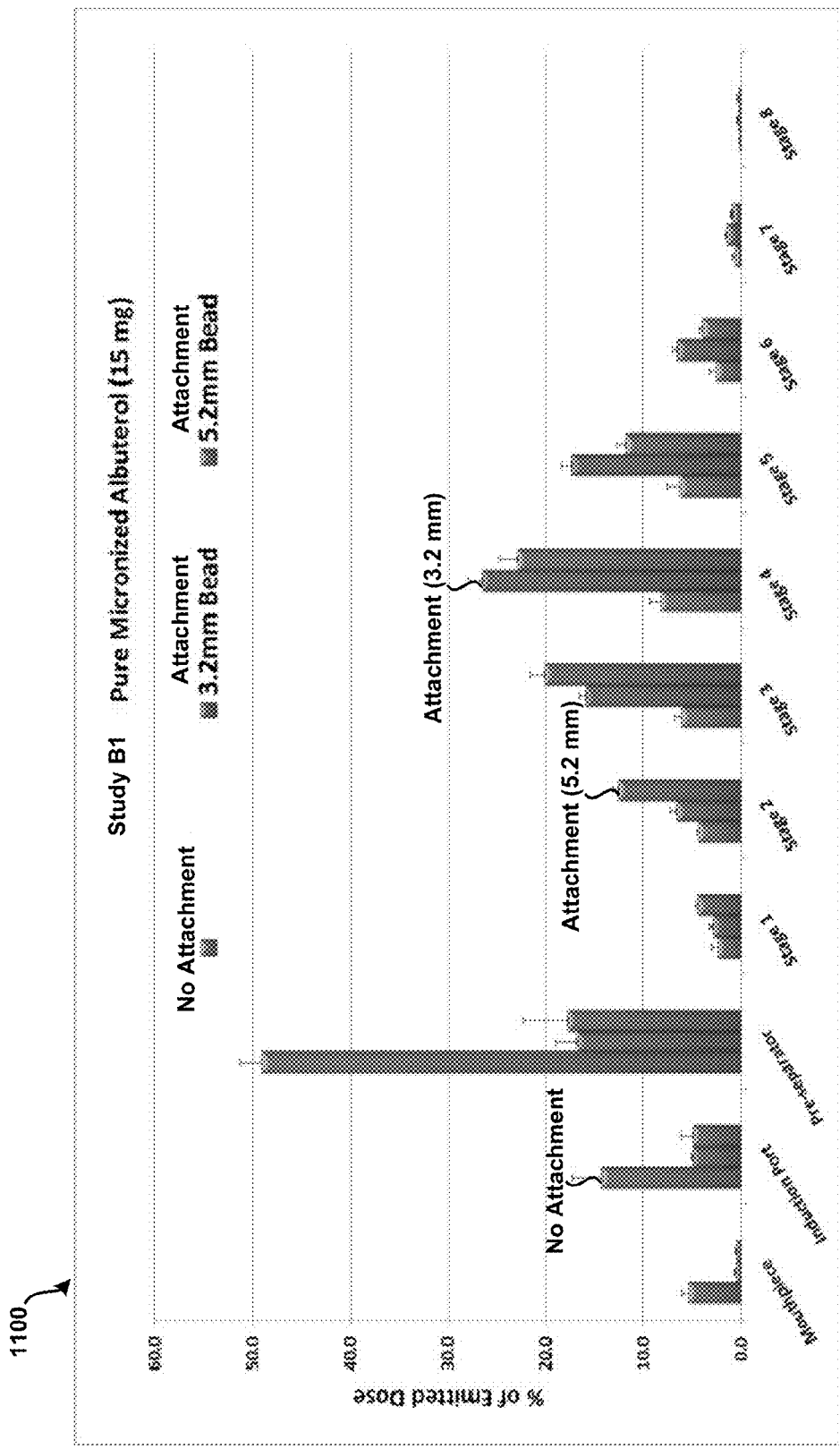
FIG. 12 shows a first stage-by-stage particle deposition distribution profile.
Figure 13:
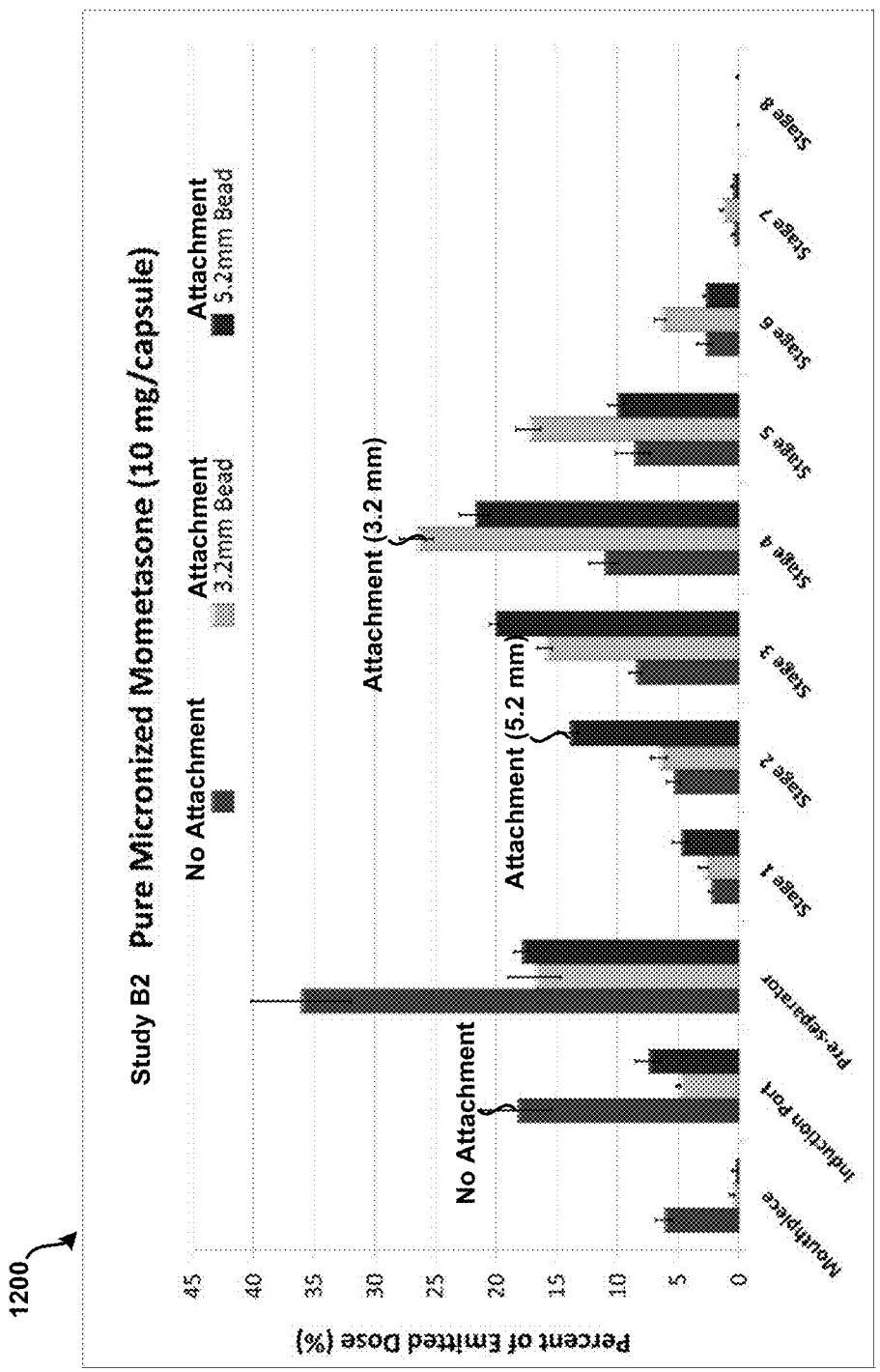
FIG. 13 shows a second stage-by-stage particle deposition distribution profile.

For example, referring now specifically to FIG. 9, a "forced-dosing" scenario is described in accordance with the present disclosure. In particular, a third view of the device 400 of FIG. 4 is shown in cross-section in FIG. 9. In this example, a coupling 902 is shown that is removably coupled to the first housing 402 of the device 400. The coupling 902 includes an inlet 904 that is removably coupled to an air source 906. In one embodiment, an individual other than a patient may prime the device 400 by puncturing a capsule, blister, or reservoir 908 of the coupling 902 using a piercing member 910. The source 906 may then be employed to force air through the device 400, drawing powder from the reservoir 908 into the adjacent chamber 104 via the inlet 102, where the bead 302 is rapidly oscillating, creating high-energy forces that may strip drug from the surface of carrier particles (e.g., when the bead 302 is drug-covered), and/or de-agglomerate powder aggregates. Drug particles may then be deposited in lungs and airways of the patient from the primary or main powder flow channel 408 based on direction of air flow through the device such as shown in FIG. 9.

Such a "forced-dosing" scenario may be beneficial when, for example, emergency treatment of unconscious or otherwise unresponsive personnel may be necessary. For example, the device 400 may enable a responder to administer treatment agent to the lungs of a patient. Additionally, the second housing 404 may itself comprise of, be coupled to, or otherwise incorporated within, a mouthpiece adapted to be placed within the mouth of a patient, or in a nasal adapter adapted to conform to the nostrils of a patient. In the example of FIG. 9, the second housing 404 of the device 400 may be securely positioned within or on the mouth or nasal passages of a patient. With air expelled from the lungs of a responder into the inlet 604, the device 400 may be activated or actuated such as to deposit a treatment agent into the lungs and airways of the patient. In this example, the source 906 corresponds to the lungs of an individual. Other embodiment are possible. For example, in some embodiments. the source 906 may comprise of a ventilation bag, mechanical ventilator, mechanical pump, etc. Still other embodiments are possible.

At least FIGS. 6-9 illustrate a scenario in which the example device 400 is coupled to, or fitted onto, an external feature of a dose containment system or powder source 602. Other embodiments are however possible. For example, referring now to FIG. 10, a scenario is illustrated in which the example device 400 is coupled to, or fitted onto, an internal feature of a dose containment system or powder source. In particular, the device 400 may replace a powder dispersion mechanism internal to an existing inhaler. An example of an existing inhaler may include the Handi-Haler®, ASMANEX® Twisthaler®, SYMBICORT® Turbuhaler® and the Budelin® Novolizer® dry powder inhalers and others. Other embodiments are possible.

For example, a dose containment system or powder source 912 may generally include a dose module 914 that holds a portion of DPF, a powder dispersion module 916, and a mouthpiece module 918 that would in practice be used to deliver a dose of the DPF to a patient. In general, the powder dispersion module 916 may exhibit a tortuous path the DPF needs to navigate between its introduction into the flow path and release from the mouthpiece module 918. The tortuous path may possibly deaggregate DPF aggregates to some degree, but may also add flow resistance. In accordance with the principles of the present disclosure, the dose containment system or powder source 912 may be modified to replace the powder dispersion module 916 with the device 400, or subassemblies of the device 400, including an inlet, chamber with a bead, and an outlet similar to the device 400. Further, this may or may not include the second housing 404 of the device 400, where an existing element of an inhaler being modified may instead be used. In this example, the device 400 may enhance the efficiency of de-aggregation of DPF of the dose containment system or powder source 912, and may lower the resistance to flow within the dose containment system or powder source 912. Other benefits and advantages are possible as well.

Referring now to FIG. 11, a simplified, conceptual, example schematic diagram of the example device 400 of FIG. 4 in multiple configurations is shown. In particular, the chamber 104 of the device 400 is shown in a series configuration 1002 with another chamber 104, and in a parallel configuration 1004 with another chamber 104. In this example, it is contemplated that multiple drugs in each their own (e.g., two or more) dispersion chambers (e.g., in addition to other elements of the example device 400 as desired) configured in accordance with the principles of the present disclosure may be coupled in series or parallel. Further, it is contemplated that any desired series/parallel combination may also be formed. For example, the series configuration 1002 may be coupled in series with the parallel configuration 1004. In another example, the parallel configuration 1004 may be coupled in series with a single particular chamber 104, and etc.

In addition, it is contemplated that the type and configuration of the bead 302 may vary in the context of FIG. 11. For example, when multiple ones of the chamber 104 are connected in series and/or parallel, one or more of the respective dispersion chambers may have similar bead sizes, different bead sizes, similar bead materials, different bead materials, and etc. Further, it is contemplated that any desired series/parallel combination may be formed. In general, type and configuration of the bead 302 may vary as desired.

Such an implementation may be beneficial in many respects. For example, for combination therapies, one drug may pass through a particular dispersion chamber and another other drug may pass through a separate dispersion chamber, or both drugs can pass through the same dispersion chamber. Additionally, "downstream" of the dispersion chambers may merge into a single dispersion chamber, or be kept separate throughout the length of the device 400, such that the powders do not mix until they are emitted from the device. Still other benefits and/or advantages are possible as well.

Referring now to FIG. 12, a first example stage-by-stage particle deposition distribution profile 1100 is shown. In particular, FIG. 12 shows an example of a simulated stage-by-stage particle distribution profile of the 15 mg pure micronized albuterol sulfate formulation discussed above in connection with Experimental study B1, for powder emitted from the "No Attachment" configuration, or the "Attachment" configuration, as described above. The stage-by-stage particle distribution profile is simulated because an experimental set-up or particle sizing apparatus using a number of meshed screens arranged to pass a particular range of particles size were positioned with respect to each other such as to model the lungs of a patient.

In FIG. 12, the first or leftmost bar in each category is associated with the "No Attachment" configuration, the second or middle bar in each category is associated with the "Attachment" configuration using a 3.2 mm bead, and the third bar or rightmost bar in each category is associated with the "Attachment" configuration using a 5.2 mm bead. In general, particle sizes become smaller as the stage number increases. Accordingly, Stage 1 will contain the largest particles at a greater concentration than Stage 2, then Stage 2, Stage 3, etc. As seen within the profile 1100, Stage 1, Stage 2, and Stage 3 show a greater deposition for the 5.2 mm bead relative to its 3.2 mm counterpart, which then switches at Stage 5 and Stage 6, where the 3.2 mm bead exhibits greater deposition than the larger bead. The Stages may correspond to particle deposition locations within the human anatomy where induction port, preseparator, Stage 1, and Stage 2 may approximate deposition within the mouth, throat, and upper airways, and Stages 3-8 may approximate deposition within the lung.

Referring now to FIG. 13, a second example stage-by-stage particle deposition distribution profile 1200 is shown. In particular, FIG. 13 shows an example of a simulated stage-by-stage particle distribution profile of the 10 mg (±0.5 mg) of pure micronized mometasone furoate, discussed above in connection with Experimental study B2, for powder emitted from the "No Attachment" configuration, or the "Attachment" configuration, as described above. In FIG. 13, the first or leftmost bar in each category is associated with the "No Attachment" configuration, the second or middle bar in each category is associated with the "Attachment" configuration using a 3.2 mm bead, and the third bar or rightmost bar in each category is associated with the "Attachment" configuration using a 5.2 mm bead. As may be understood upon inspection of the profile 1200, a similar trend as observed in the profile 1100 is observed with the pure micronized mometasone furoate. Further it may be understood from the profile 1200, and the profile 1100, that using the diameter of the bead 302 the particle size distribution may be tailored to a particular target profile. As an example, certain drugs may require central lung deposition, whereas other drugs may require more peripheral lung deposition. In one example, the term particle size distribution may refer to an aerodynamic particle size distribution. In general, an aerodynamic particle size may equal the diameter of a sphere that has the same or similar drag coefficient as a given particle. In this example, the bead 302 may be selected to have a size such that upon oscillation it produces a desired aerodynamic particle size distribution of powdered medicament. Further, a desired aerodynamic particle size distribution may obtained as a function of a diameter of the bead 302.

Altering the bead size can influence the aerodynamic particle size distribution profile of the emitted drug and thus may enable regional targeting of the lung by altering the diameter of the bead size, while maintaining the chamber and inlet diameters proportional, rather than by altering the formulation, which can be a more costly and time intensive process. In the above example experimental studies, the proportions of the inlet and dispersion chamber diameters were kept constant to the diameter of the bead as: $d_{bead}^2 \cong (d_{inlet})(d_{chamber})$, where the ratio of the diameter of the dispersion chamber (chamber 104) to that of the inlet is approximately or about 2.1. However, other embodiments are possible. For example, the ratio of the diameter of the dispersion chamber to that of the inlet may be within a range of about greater than 1.1 to about 3.0. In other embodiments, the ratio of the diameter of the dispersion chamber to that of the inlet may be within a range of about 1.5 to about 2.5. Still other embodiments are possible.

Figure 14:
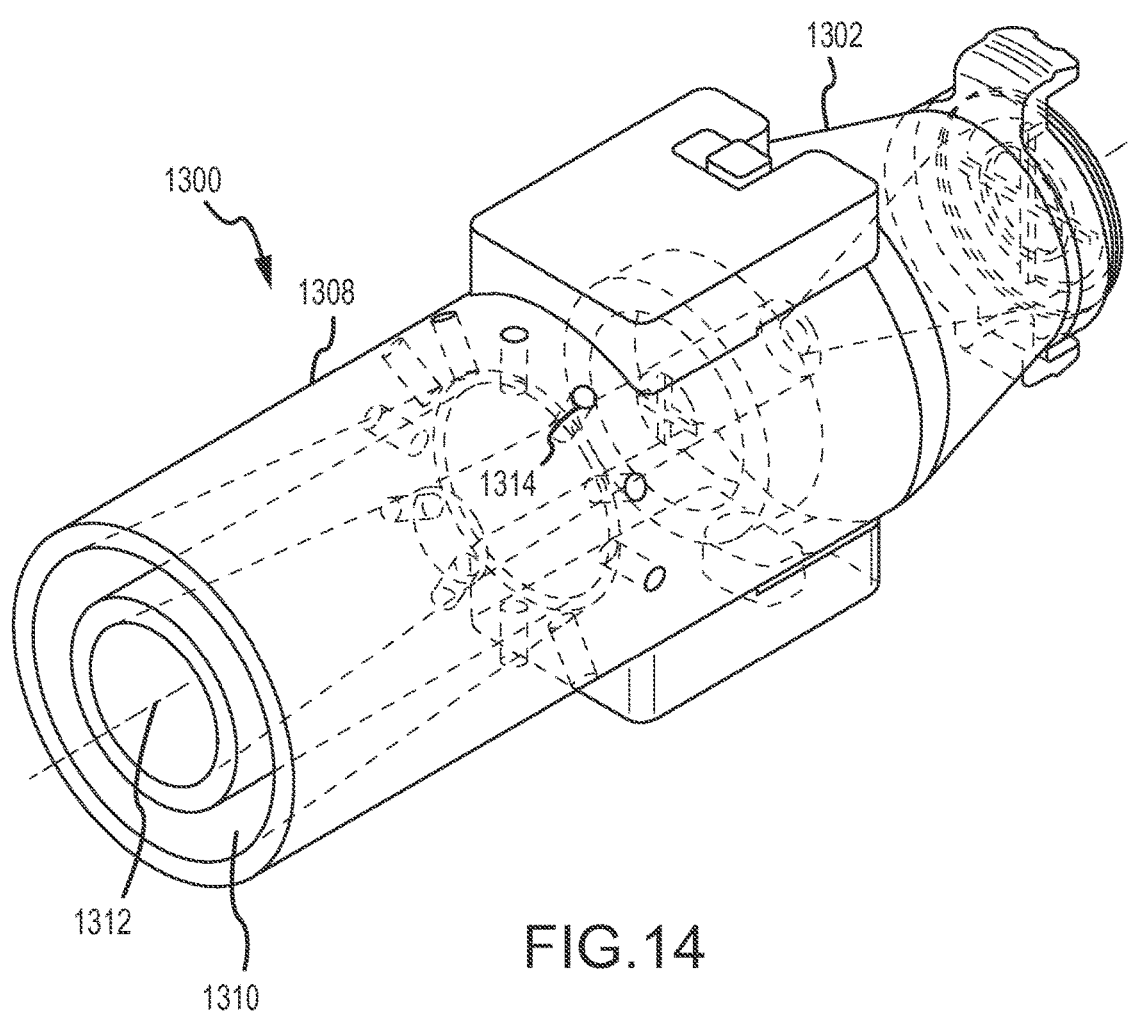
FIG. 14 shows a first perspective view of a first example powder dispersion device.
Figure 15:
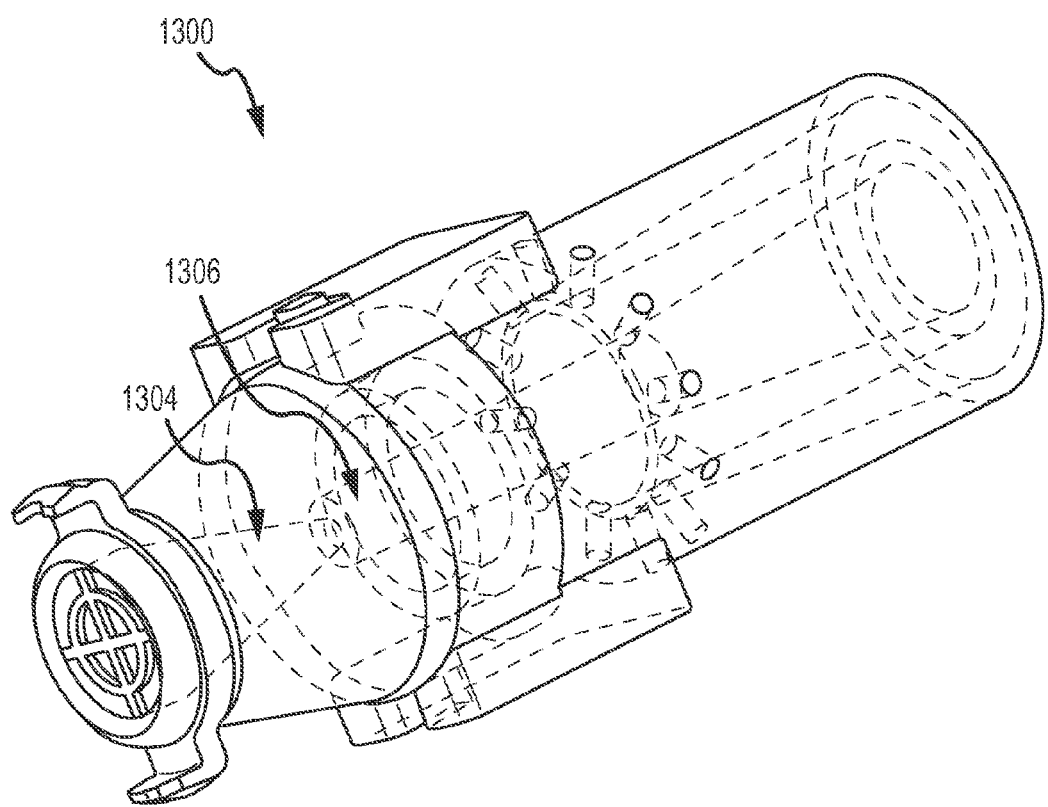
FIG. 15 shows a second perspective view of the device of FIG. 14.
Figure 16:
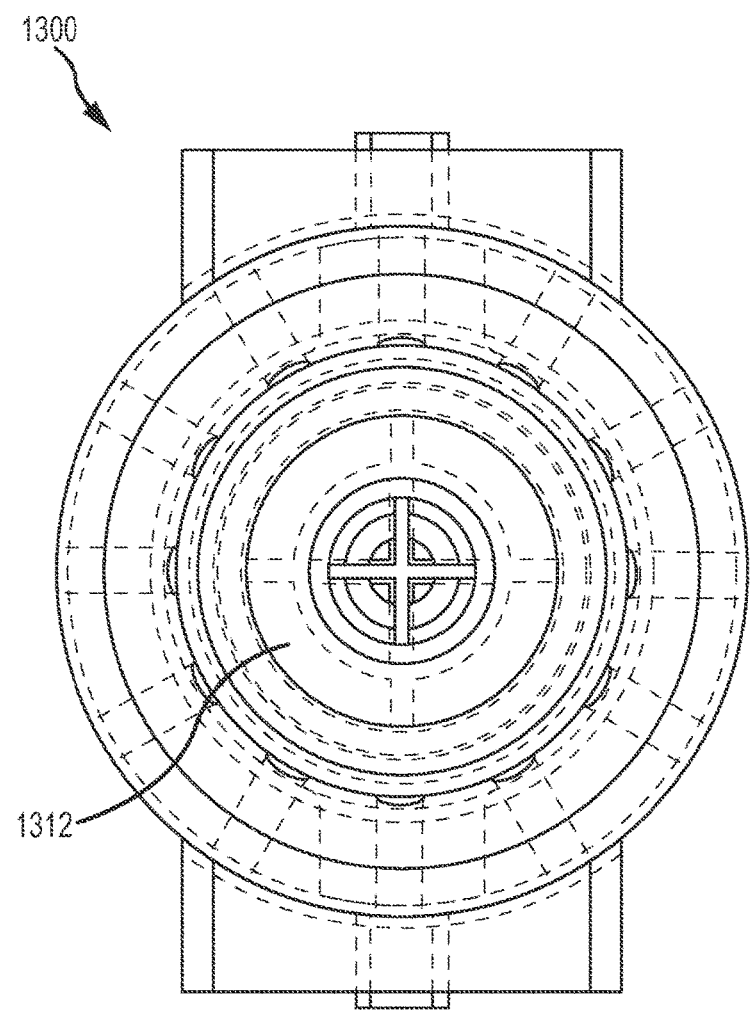
FIG. 16 shows a first end view of the device of FIG. 14.
Figure 17:
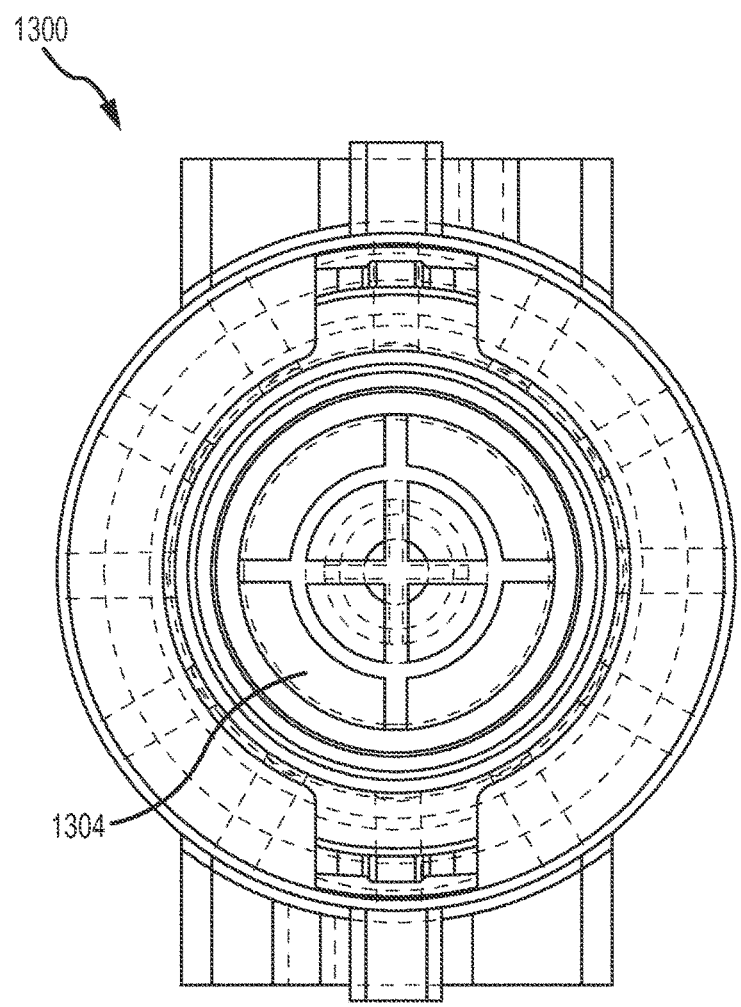
FIG. 17 shows a second end view of the device of FIG. 14.

Referring now to FIGS. 14-17, a first example powder dispersion device or inhaler 1300 is shown in accordance with the principles of the present disclosure. In general, the device 1300 may be configured to be coupled to another inhaler device. In particular, FIG. 14 shows a first perspective view of the device 1300. FIG. 15 shows a second perspective view of the device 1300. FIG. 16 shows a first end view of the device 1300. FIG. 17 shows a second end view of the device 1300.

In general, the device 1300 may be similar to or otherwise correspond to the device 400 discussed above in connection with FIGS. 1-13. For example, the device 1300 may include a first housing 1302 comprising an inlet 1304 and a chamber 1306. The inlet 1304 and a chamber 1306 may be arranged and/or configured in a manner similar to the inlet 102 and chamber 104 of the device 400. Additionally, although not expressly shown, the bead 302 may be positioned within the chamber 1306, such as shown in FIG. 3. The device 1300 may further include a second housing 1308 comprising a sheath flow channel 1310 that surrounds a primary or main powder flow channel 1312. The device 400 may further include a plurality of flow bypass channels 1314 that are formed within the second housing 1308. The flow bypass channels 1314 may be in fluid connection with the sheath flow channel 1310.

Figure 18:
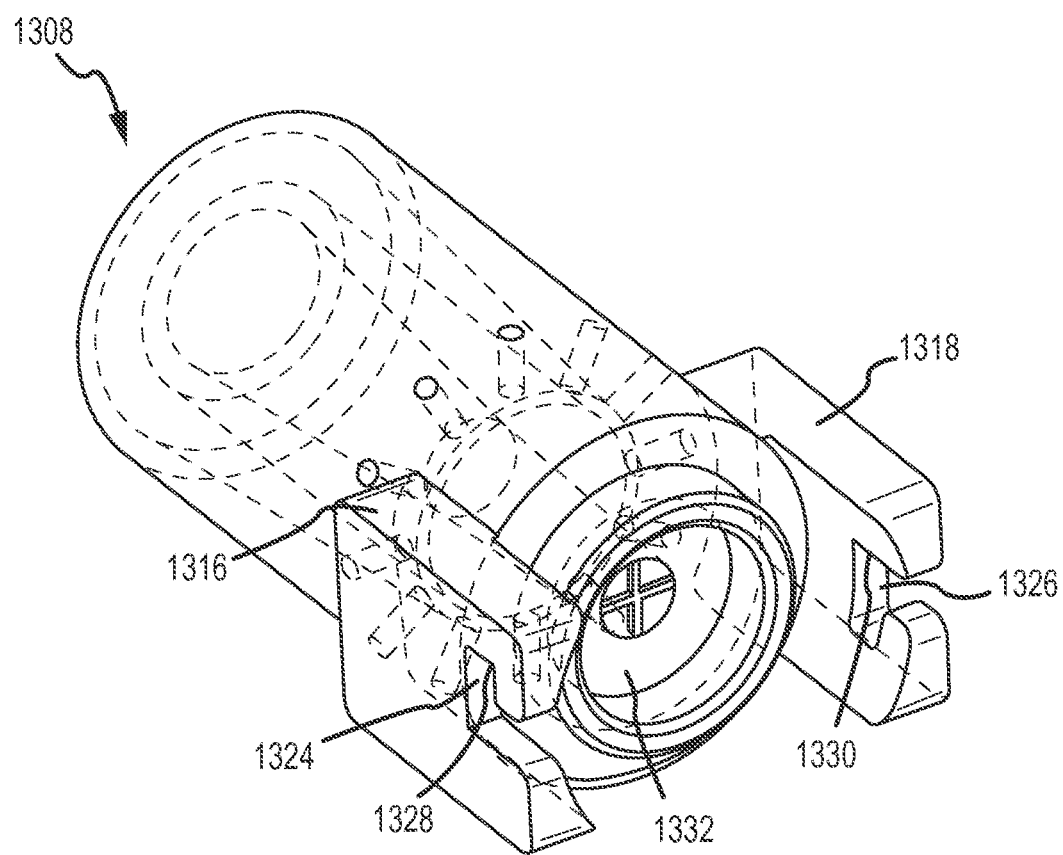
FIG. 18 shows a first perspective view of a second housing of the device of FIG. 14.
Figure 19:
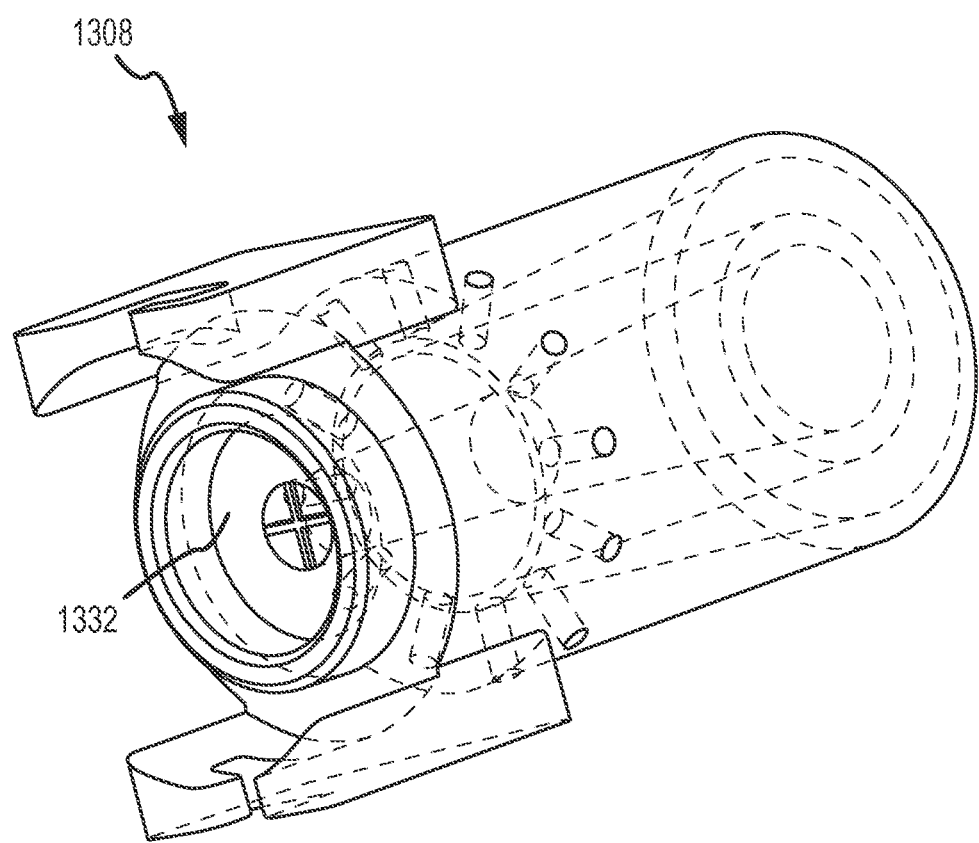
FIG. 19 shows a second perspective view of the housing of FIG. 18.
Figure 20:
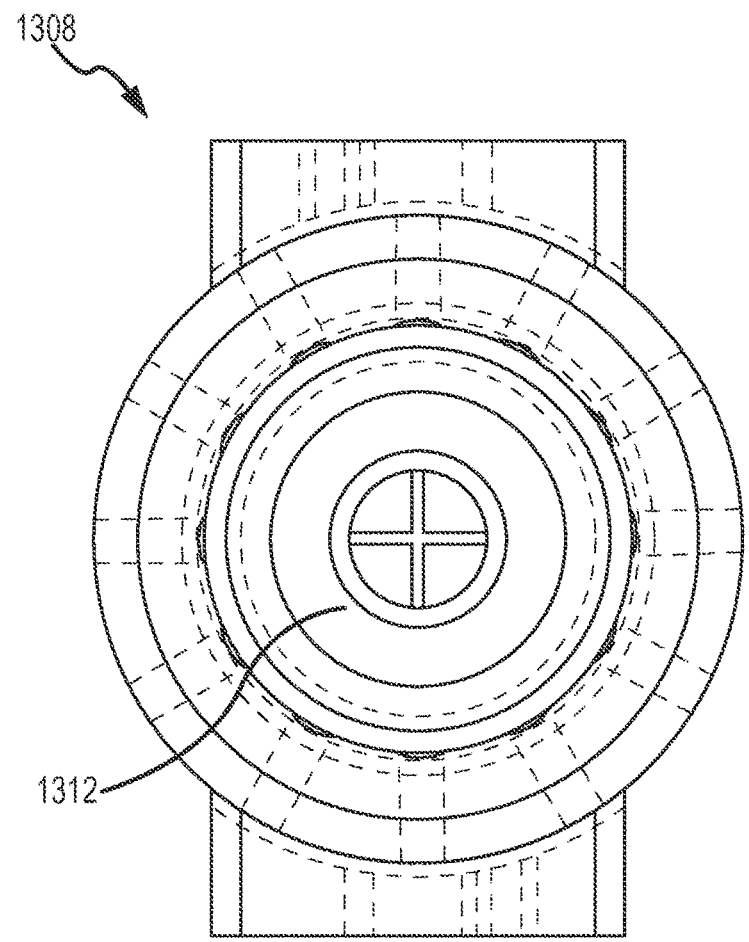
FIG. 20 shows a first end view of the housing of FIG. 18.
Figure 21:
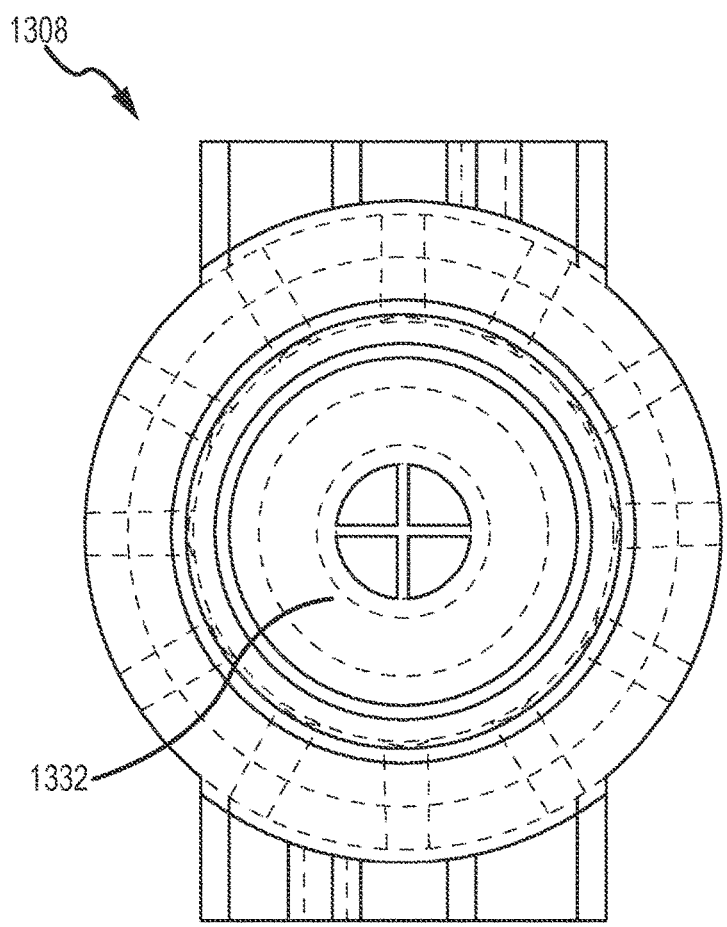
FIG. 21 shows a second end view of the housing of FIG. 18.

FIGS. 18-21 show the second housing 1308 of the device 1300 in multiple views. In particular, FIG. 18 shows a first perspective view of the second housing 1308. FIG. 19 shows a second perspective view of the second housing 1308. FIG. 20 shows a first end view of the second housing 1308. FIG. 21 shows a second end view of the second housing 1308.

Figure 22:
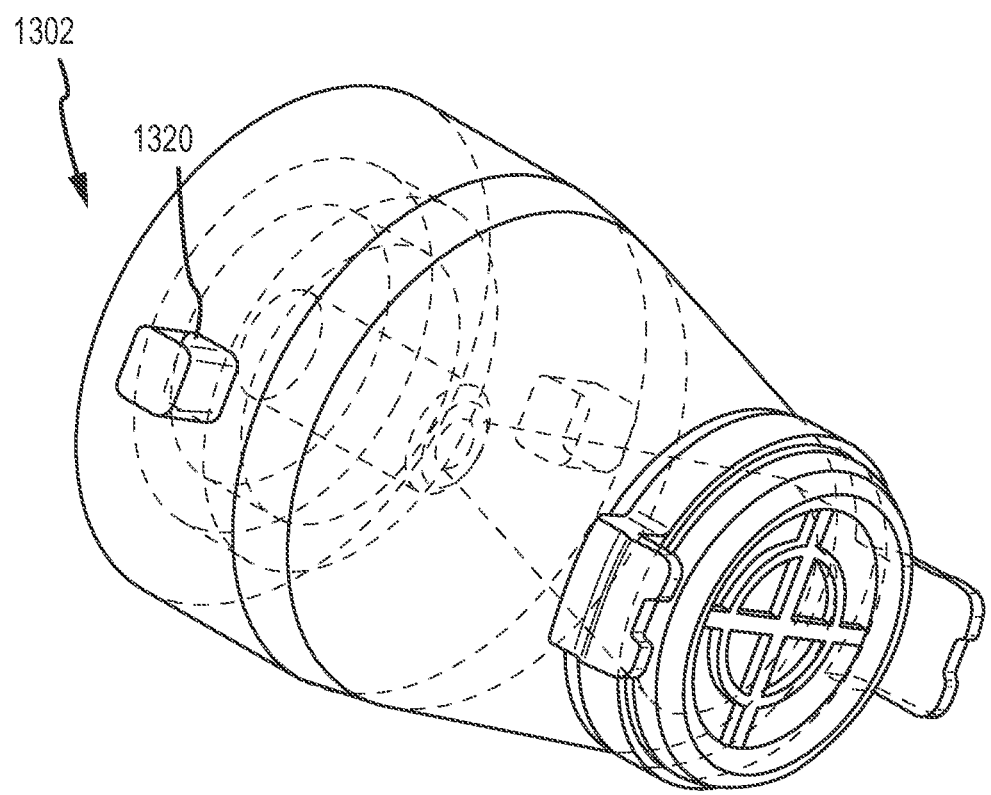
FIG. 22 shows a first perspective view of a first housing of the device of FIG. 14.
Figure 23:
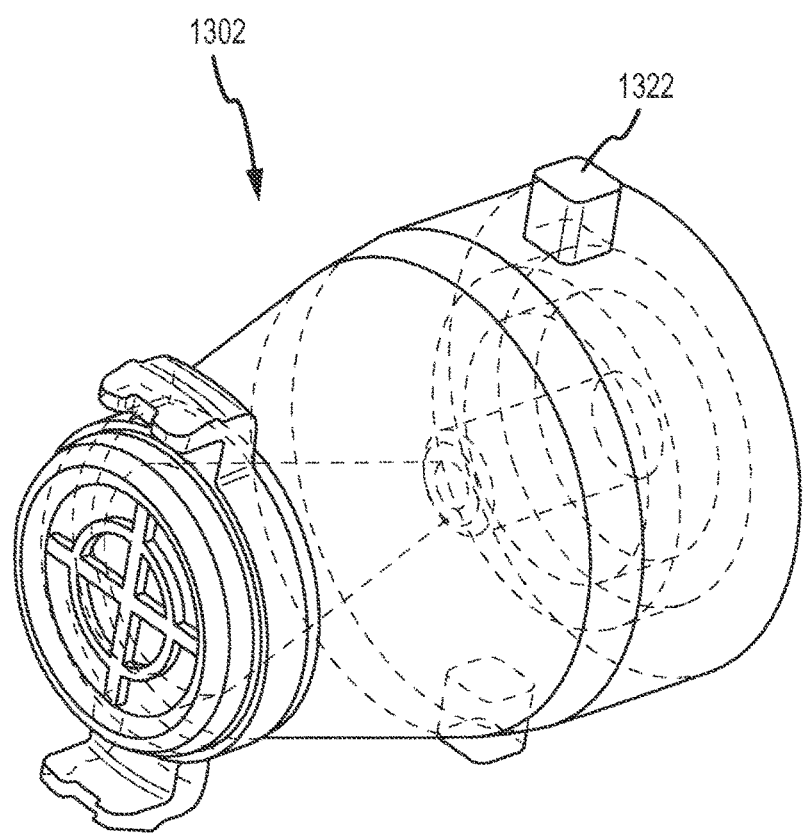
FIG. 23 shows a second perspective view of the housing of FIG. 22.
Figure 24:
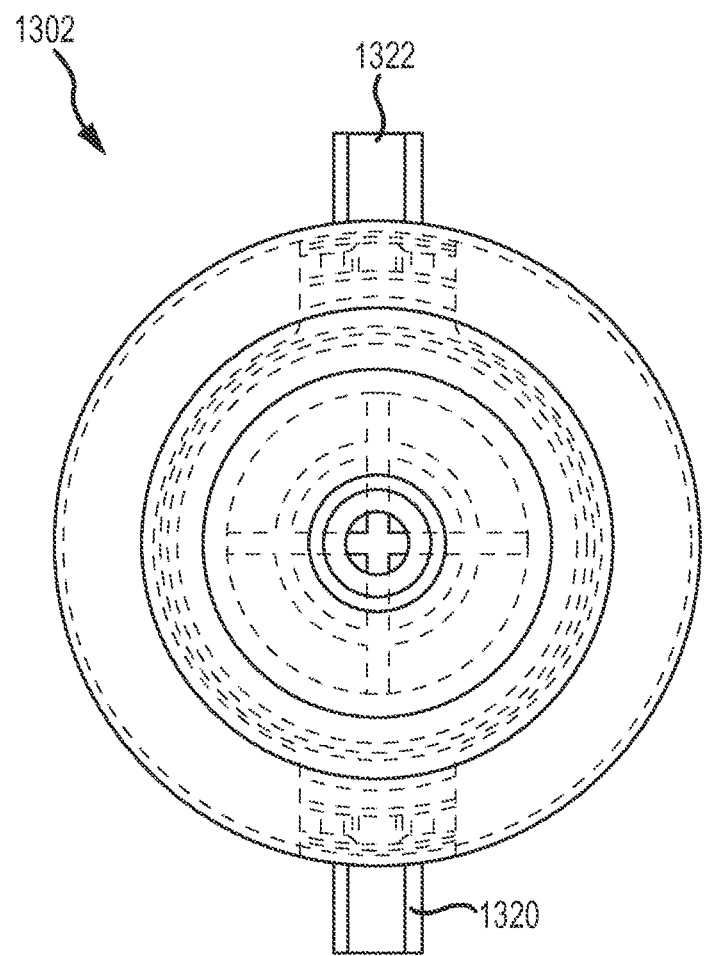
FIG. 24 shows a first end view of the housing of FIG. 22.
Figure 25:
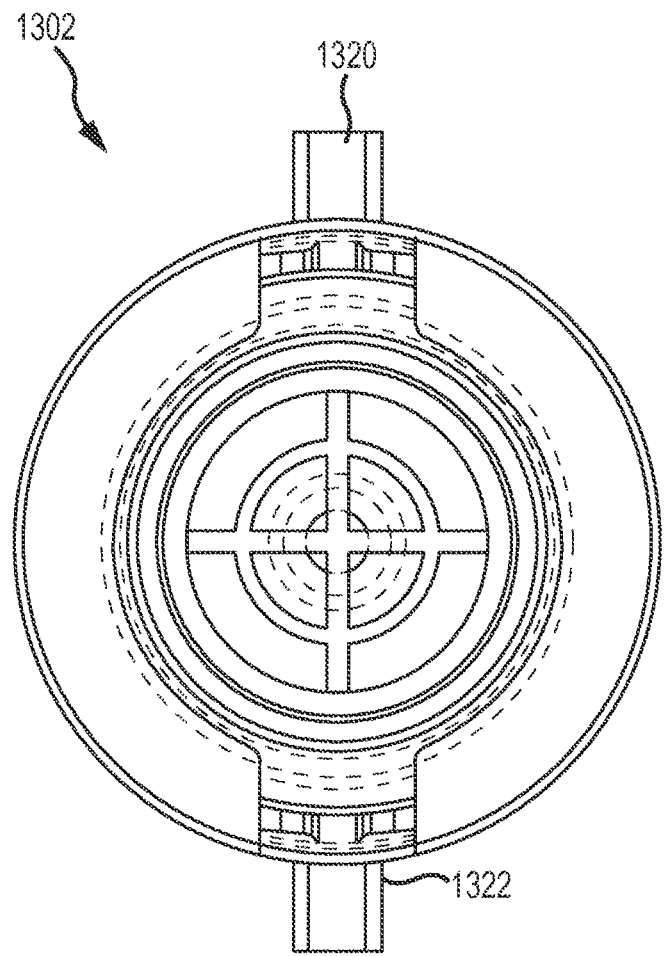
FIG. 25 shows a second end view of the housing of FIG. 22.

FIGS. 22-25 show the first housing 1302 of the device 1300 in multiple views. In particular, FIG. 22 shows a first perspective view of the first housing 1302. FIG. 23 shows a second perspective view of the first housing 1302. FIG. 24 shows a first end view of the first housing 1302. FIG. 25 shows a second end view of the first housing 1302.

A locking mechanism that may be used to couple or otherwise fasten the first housing 1302 with the second housing 1308 may be understood upon inspection of at least FIGS. 18-25. In particular, the second housing 1308 may include a first locking member 1316 and a second locking member 1318. The first housing 1302 may include a first bar 1320 and a second bar 1322. In practice, the first housing 1302 and the second housing 1308 may be positioned or orientated with respect to each other and manipulated such that the first bar 1320 is engaged with a first stop surface 1324 of the first locking member 1316 (see FIG. 18), and the second bar 1322 is engaged with a first stop surface 1326 of the second locking member 1318. The first housing 1302 and the second housing 1308 may then be manipulated such as to rotate the first housing 1302 with respect to the second housing 1308 (or vice versa) until the first bar 1320 is engaged with a second stop surface 1328 of the first locking member 1316, and the second bar 1322 is engaged with a second stop surface 1330 of the second locking member 1318. In this position, the first bar 1320 may be secured by compression fitting with the first locking member 1316, and the second bar 1322 may be secured by compression fitting with the second locking member 1318, thereby coupling the first housing 1302 with the second housing 1308. A reverse process may be implemented to decouple the first housing 1302 from the second housing 1308. Such interchangeability may be beneficial in many respects. For example, when a bead 302 of different size is desired, the first housing 1302 may be removed and replaced with another first housing 1302 having a bead 302 of different size than the original housing. Other benefits are possible as well.

Additionally, referring specifically to FIG. 18, a retaining member 1332 of the second housing 1308 may include one or more openings sized to permit air and powdered or otherwise aerosolized medicament to pass through the retaining member 1332, and to prevent the bead 302 from passing through the retaining member 1332. Other embodiments are possible. For example, in some embodiments, a different mechanism may be used and to prevent the bead 302 from exiting the chamber 1306 into the second housing 1308.

Figure 26:
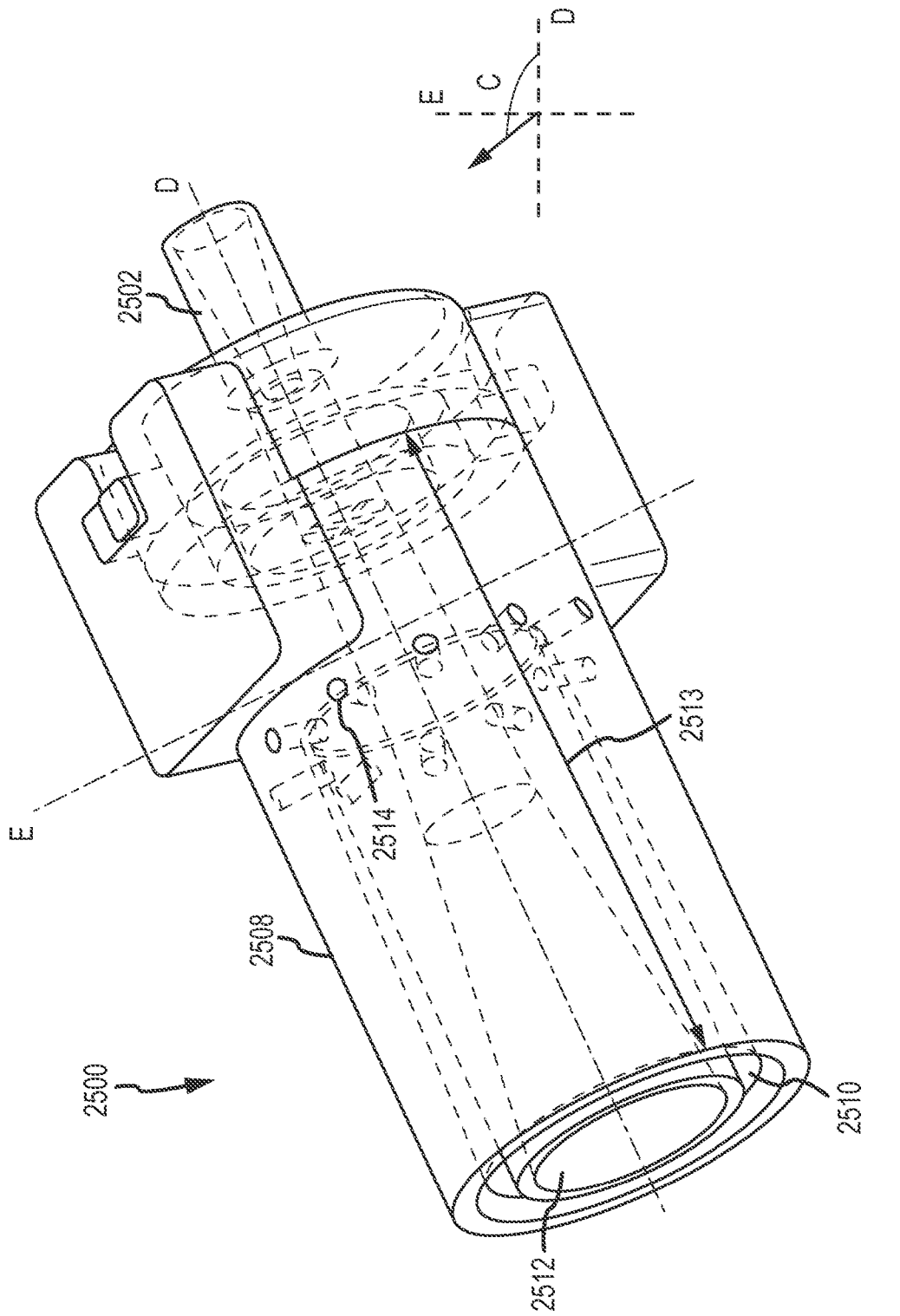
FIG. 26 shows a first perspective view of a second example powder dispersion device.
Figure 27:
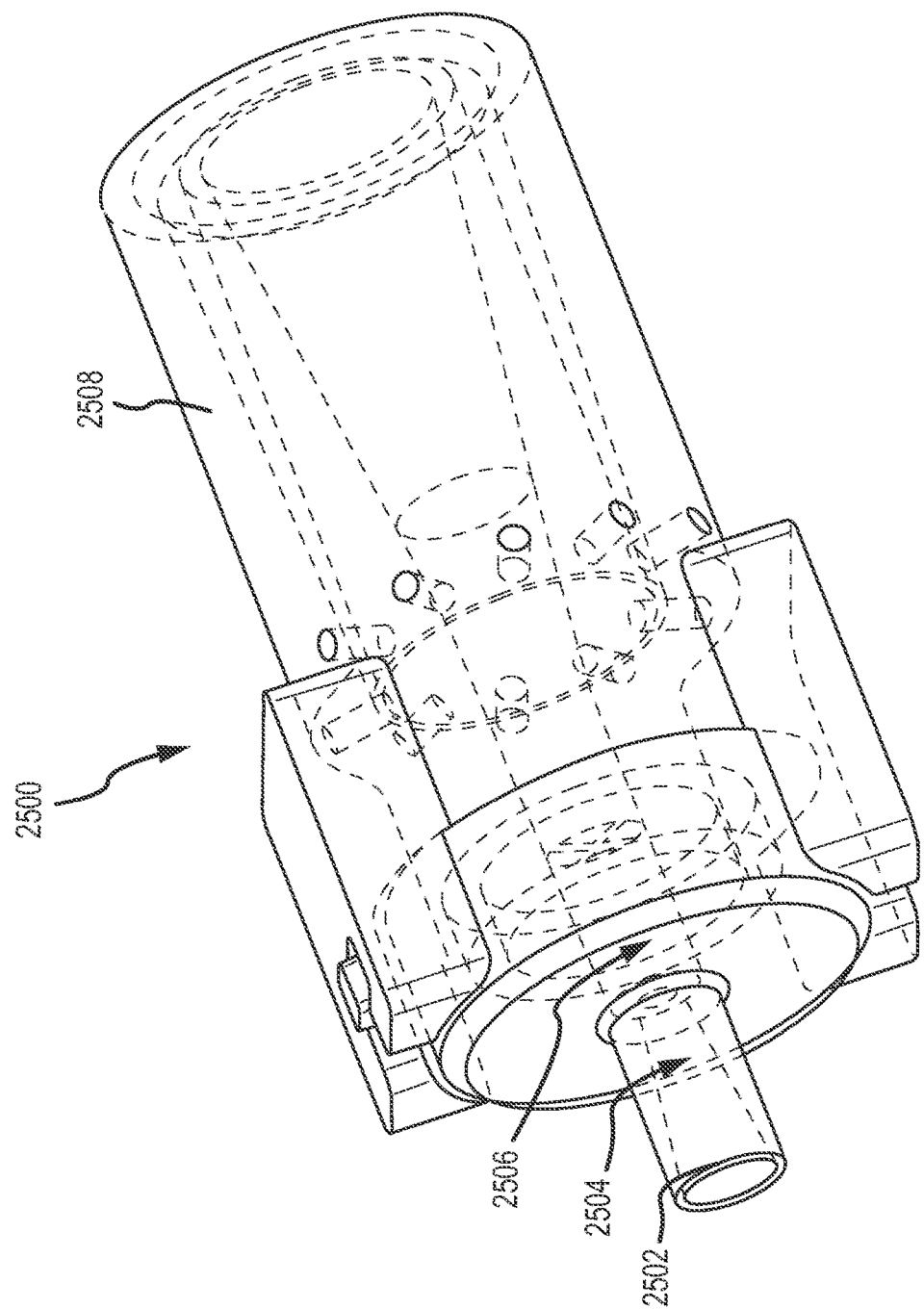
FIG. 27 shows a second perspective view of the device of FIG. 26.
Figure 28:
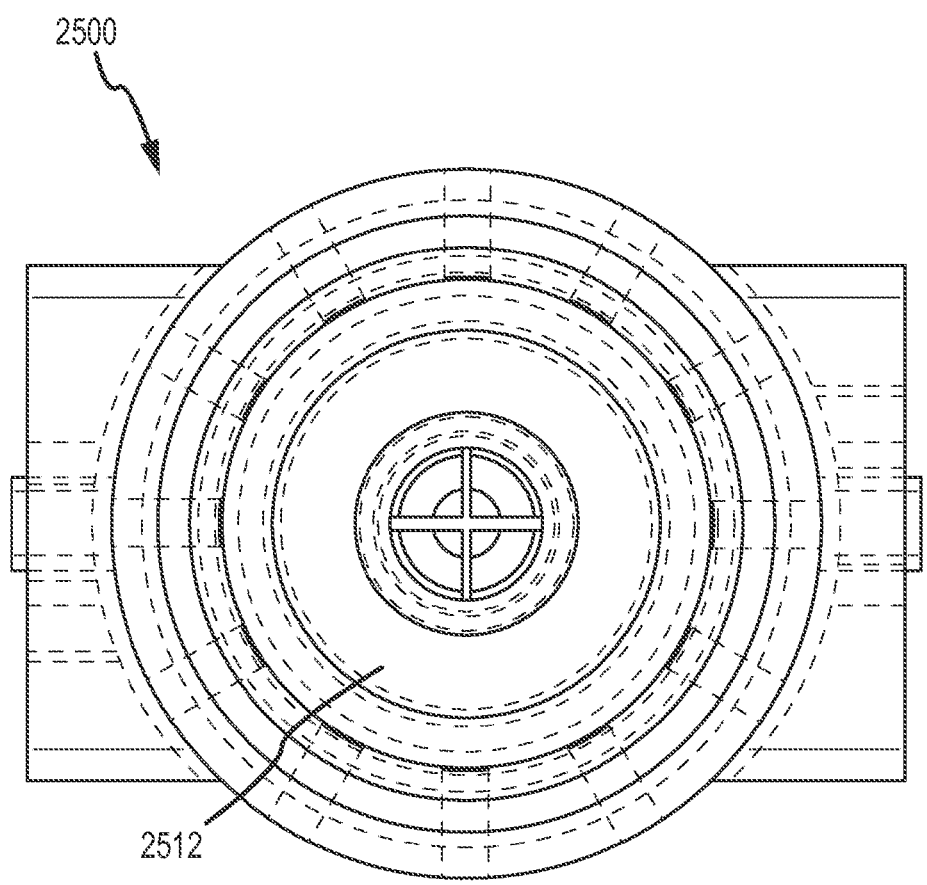
FIG. 28 shows a first end view of the device of FIG. 26.
Figure 29:
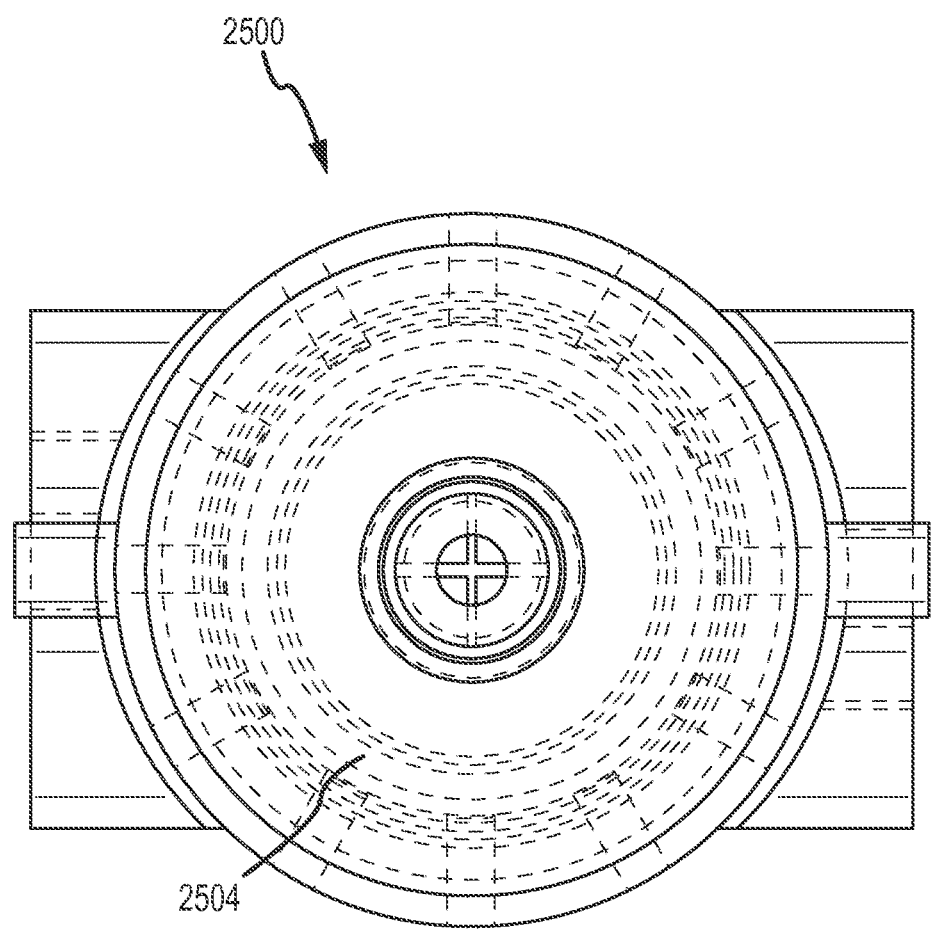
FIG. 29 shows a second end view of the device of FIG. 26.

Referring now to FIGS. 26-29, a second example powder dispersion device or inhaler 2500 is shown in accordance with the principles of the present disclosure. In general, the device 2500 may be configured to be coupled to another inhaler device. In particular, FIG. 26 shows a first perspective view of the device 2500. FIG. 27 shows a second perspective view of the device 2500. FIG. 28 shows a first end view of the device 2500. FIG. 29 shows a second end view of the device 2500.

In general, the device 2500 may be similar to or otherwise correspond to the powder dispersion device or inhaler 400 discussed above in connection with FIGS. 1-13. For example, the device 2500 may include a first housing 2502 comprising an inlet 2504 and a chamber 2506. Additionally, although not expressly shown, the bead 302 may be positioned within the chamber 2506, such as shown in FIG. 3. The device 2500 may further include a second housing 2508 comprising a sheath flow channel 2510 that surrounds a primary or main powder flow channel 2512. The device 2500 may further include a plurality of flow bypass channels 2514 that are formed within the second housing 2508 or enter the sheath flow channel 2510 parallel to a longitudinal axis of the main powder flow channel 2512. The flow bypass channels 2514 may be in fluid connection with the sheath flow channel 2510. Further, referring specifically to FIG. 26, in some embodiments, the flow bypass channels 2514 may be formed anywhere along a length 2513 of the second housing 2508. Still further, the flow bypass channels 2514 may be formed at any predetermined and desired angle C within the second housing 2508 as measured with reference to a central axis D, and an axis E perpendicular to the central axis D, of the device 2500. For example, in FIG. 26, while the flow bypass channels 2514 are illustrated as approximately normal to the central axis D, the flow bypass channels 2514 may be angled with respect to the central axis D (as measured with respect to the axis E). Angled flow bypass channels 2514 may in some instances be more easily fabricated via an injection molding process. Other ones of the devices 400, 1300, etc., of the present disclosure may exhibit such characteristics as well.

Figure 30:
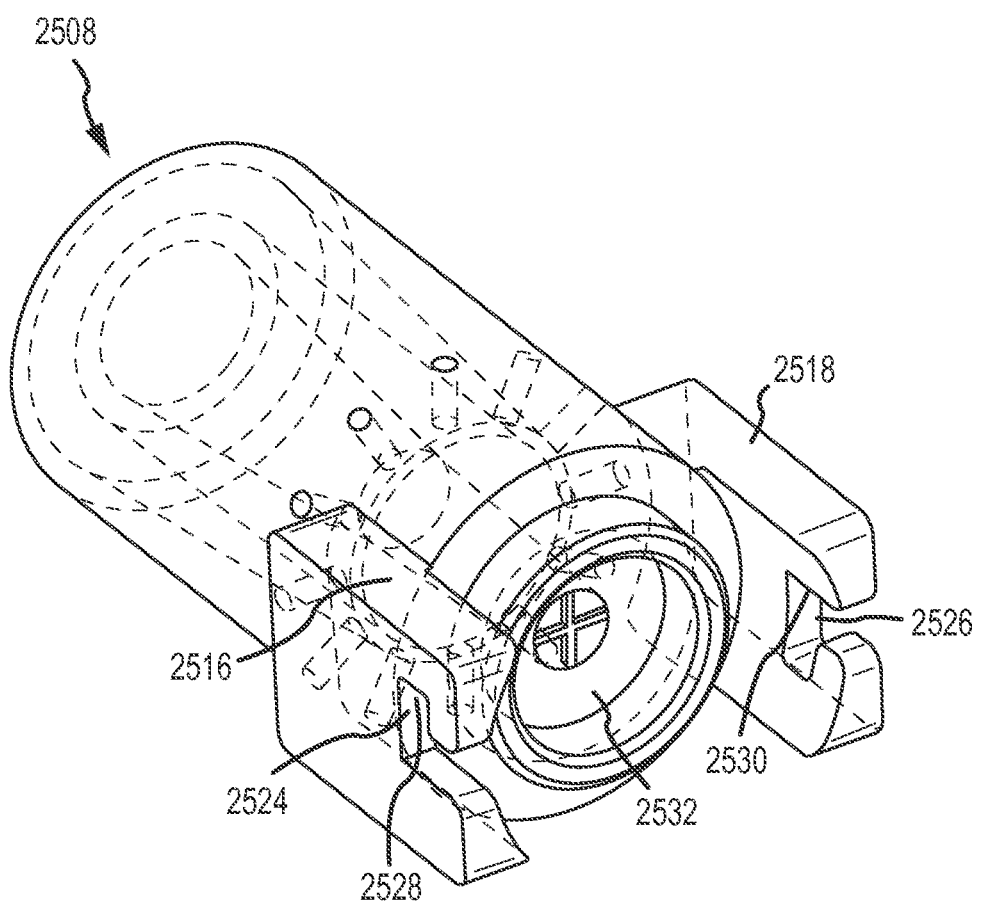
FIG. 30 shows a first perspective view of a second housing of the device of FIG. 26.
Figure 31:
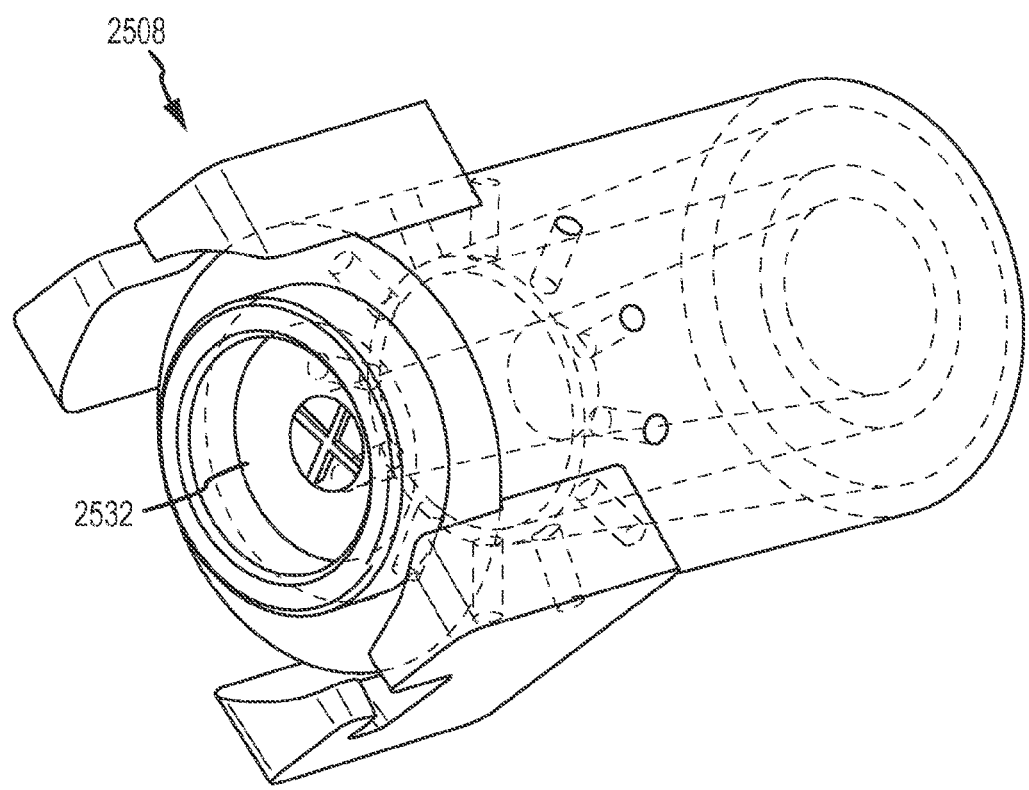
FIG. 31 shows a second perspective view of the housing of FIG. 30.
Figure 32:
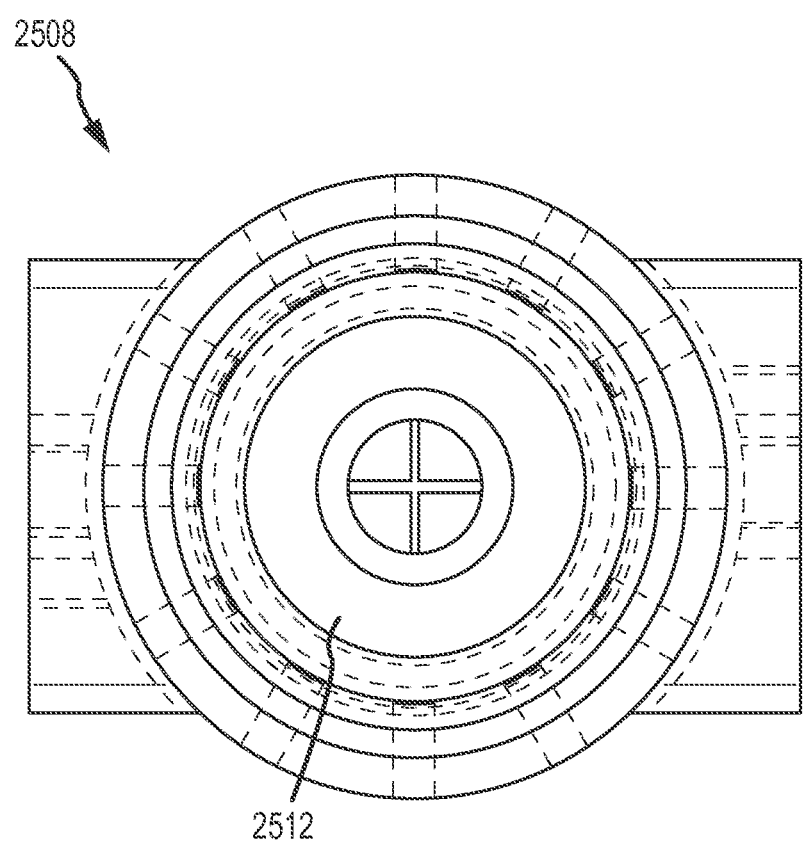
FIG. 32 shows a first end view of the housing of FIG. 30.
Figure 33:
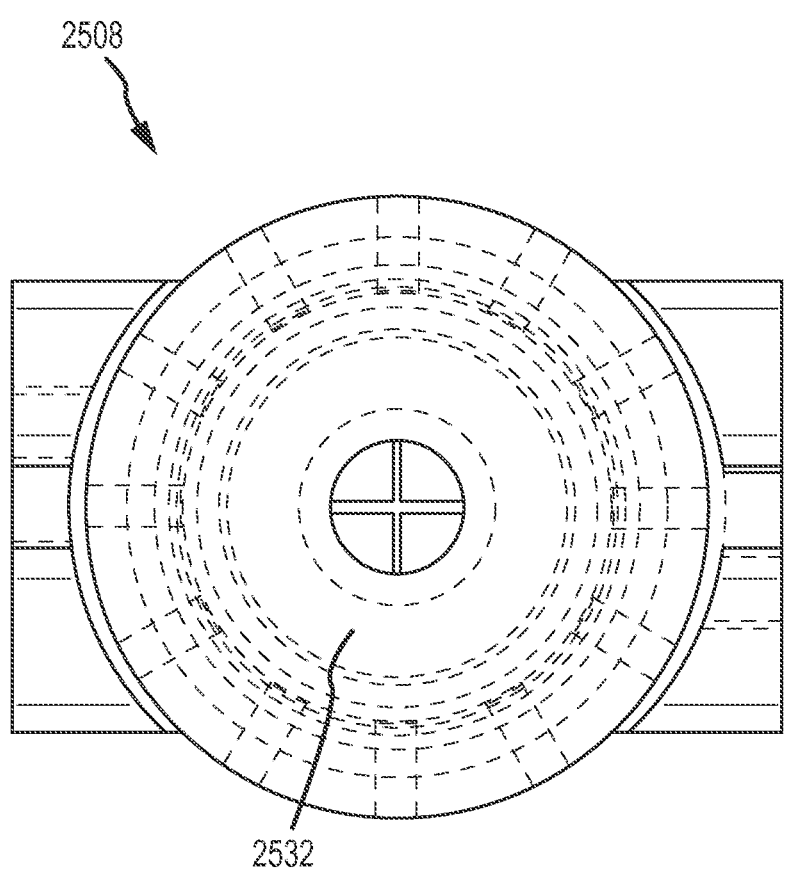
FIG. 33 shows a second end view of the housing of FIG. 30.

FIGS. 30-33 show the second housing 2508 of the device 2500 in multiple views. In particular, FIG. 30 shows a first perspective view of the second housing 2508. FIG. 31 shows a second perspective view of the second housing 2508. FIG. 32 shows a first end view of the second housing 2508. FIG. 33 shows a second end view of the second housing 2508.

Figure 34:
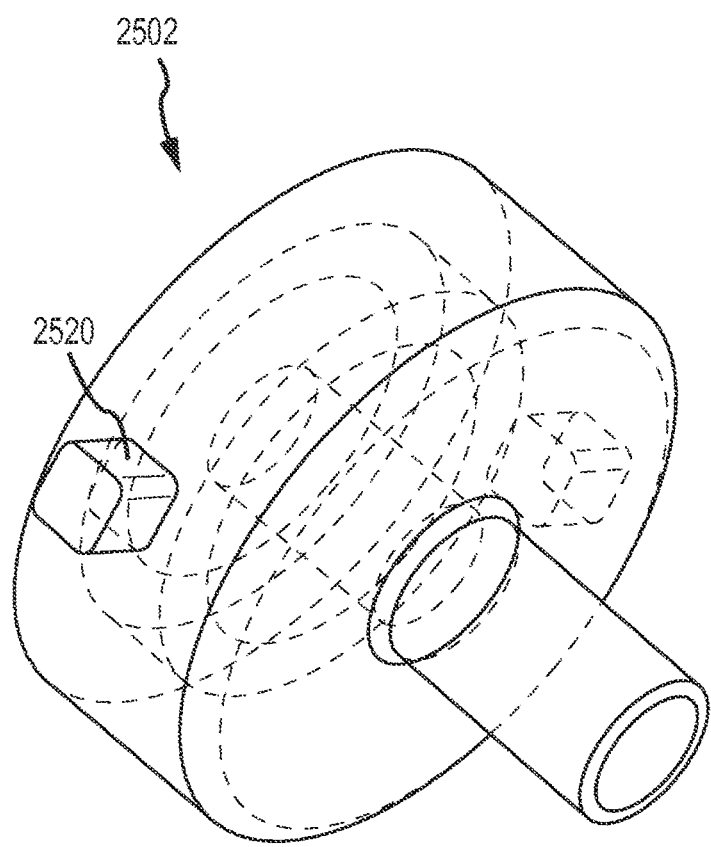
FIG. 34 shows a first perspective view of a first housing of the device of FIG. 26.
Figure 35:
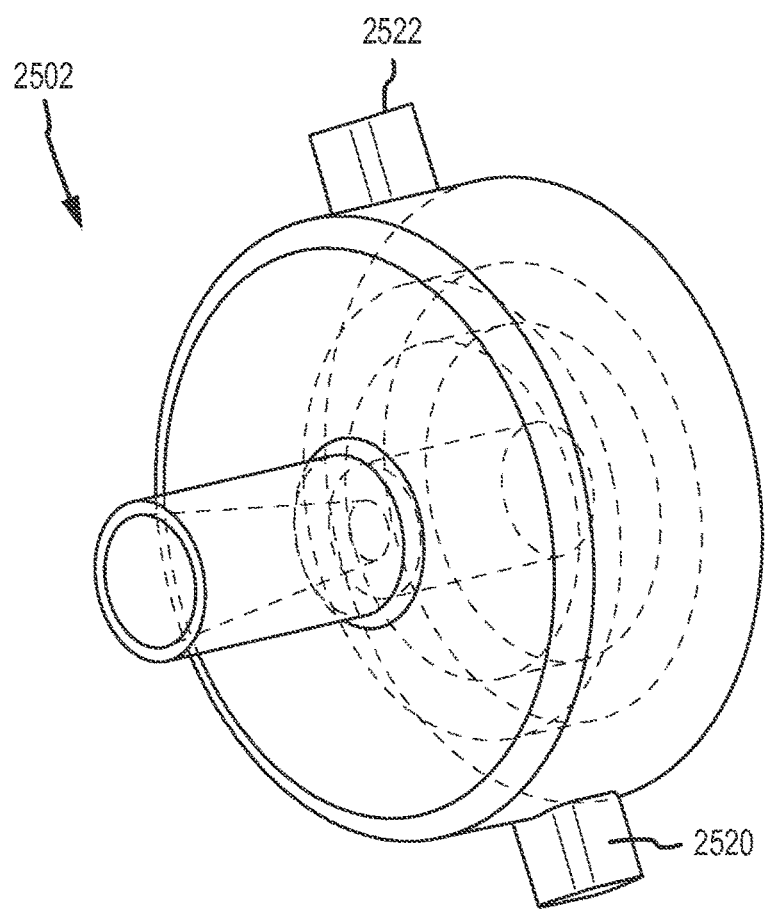
FIG. 35 shows a second perspective view of the housing of FIG. 34.
Figure 36:
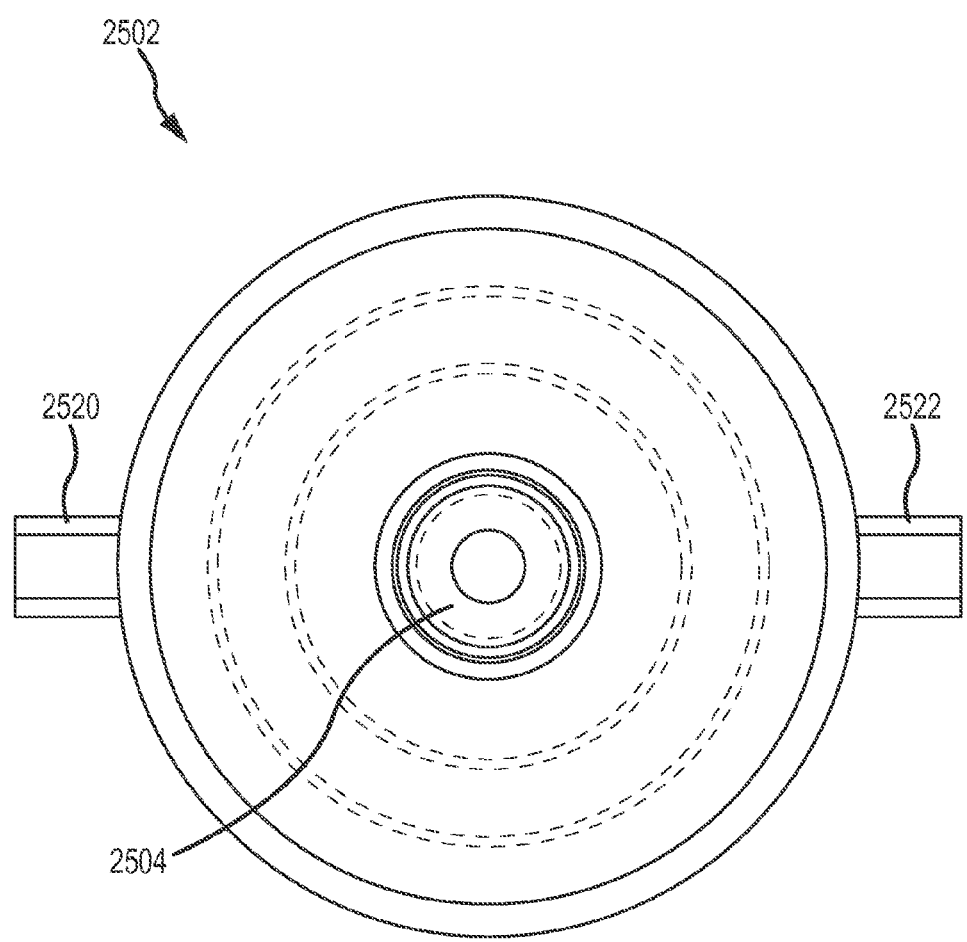
FIG. 36 shows a first end view of the housing of FIG. 34.
Figure 37:
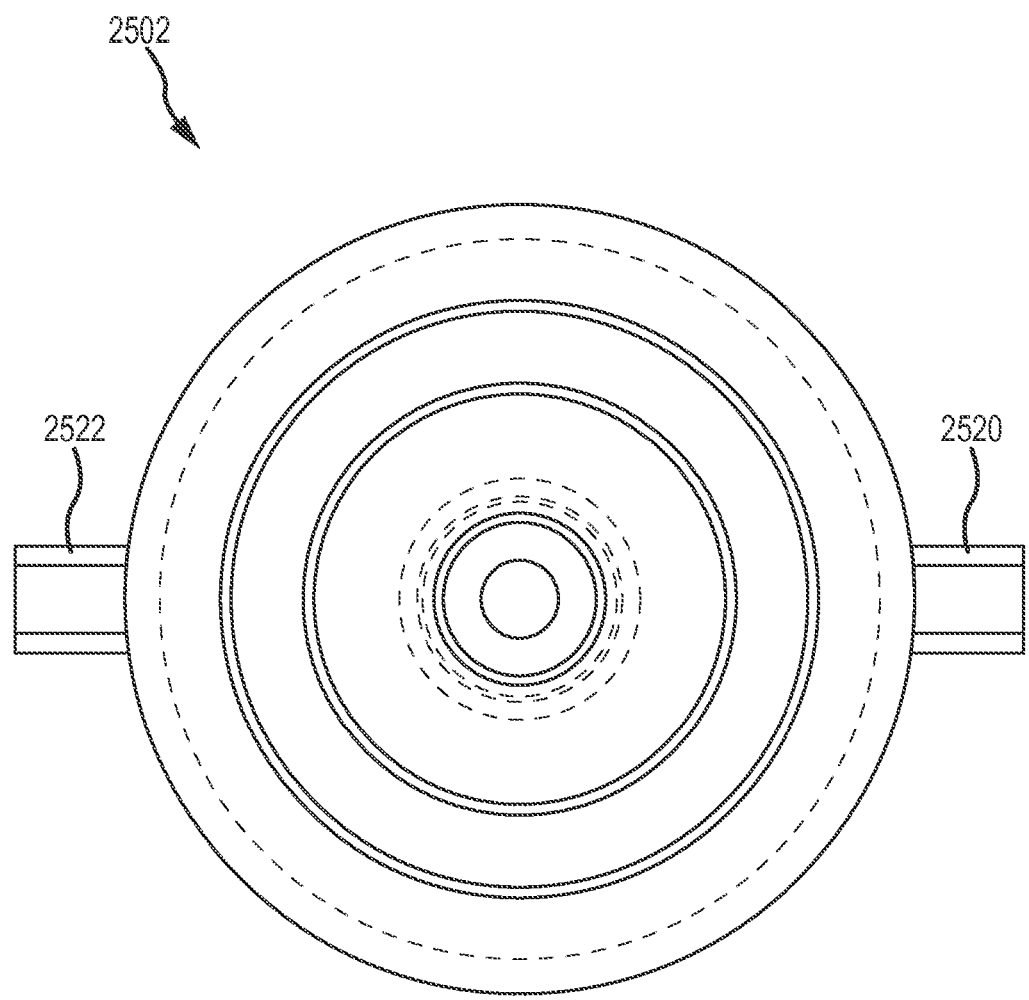
FIG. 37 shows a second end view of the housing of FIG. 34.

FIGS. 34-37 show the first housing 2502 of the device 2500 in multiple views. In particular, FIG. 34 shows a first perspective view of the first housing 2502. FIG. 35 shows a second perspective view of the first housing 2502. FIG. 36 shows a first end view of the first housing 2502. FIG. 37 shows a second end view of the first housing 2502.

A coupling mechanism that may be used to fasten the first housing 2502 with the second housing 2508 may be understood upon inspection of at least FIGS. 30-37. In particular, the second housing 2508 may include a first locking member 2516 and a second locking member 2518 (see FIG. 30). The first housing 2502 may include a first bar 2520 and a second bar 2522. The first locking member 2516 may also include a first stop surface 2524 and a second stop surface 2528, and the second locking member 2518 may also include a first stop surface 2526 and a second stop surface 2530. In practice, the first housing 205 and the second housing 2508 may be coupled and decoupled in manner similar to that described above in connection with the first example powder dispersion device or inhaler 1300. Such interchangeability may be beneficial in many respects. For example, when a bead 302 of different size is desired, the first housing 2502 may be removed and replaced with another first housing 2502 having a bead 302 of different size than the original housing. Other benefits are possible as well.

Additionally, referring specifically to FIG. 30, a retaining member 2532 of the second housing 2508 may include one or more openings sized to permit air and powdered or otherwise aerosolized medicament to pass through the retaining member 2532, and to prevent the bead 302 from passing through the retaining member 2532. Other embodiments are possible. For example, in some embodiments, a different mechanism may be used and to prevent the bead 302 from exiting the chamber 2506 into the second housing 2508.

Figure 38:
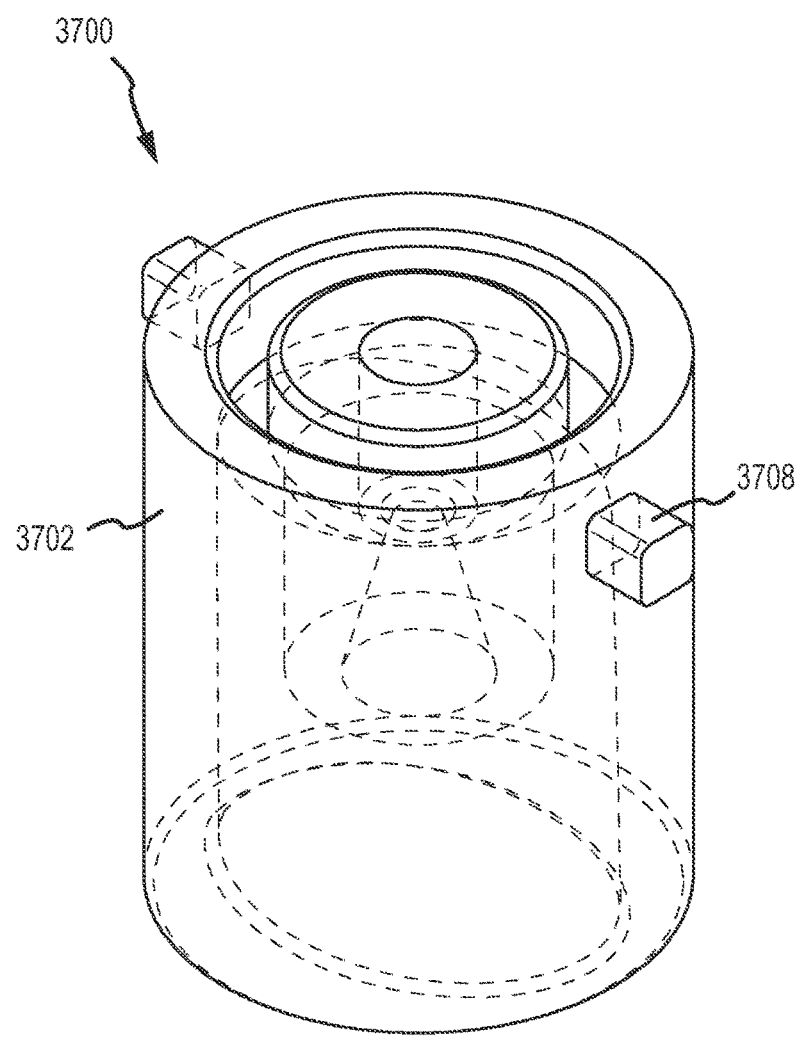
FIG. 38 shows a first perspective view of a third example powder dispersion device.
Figure 39:
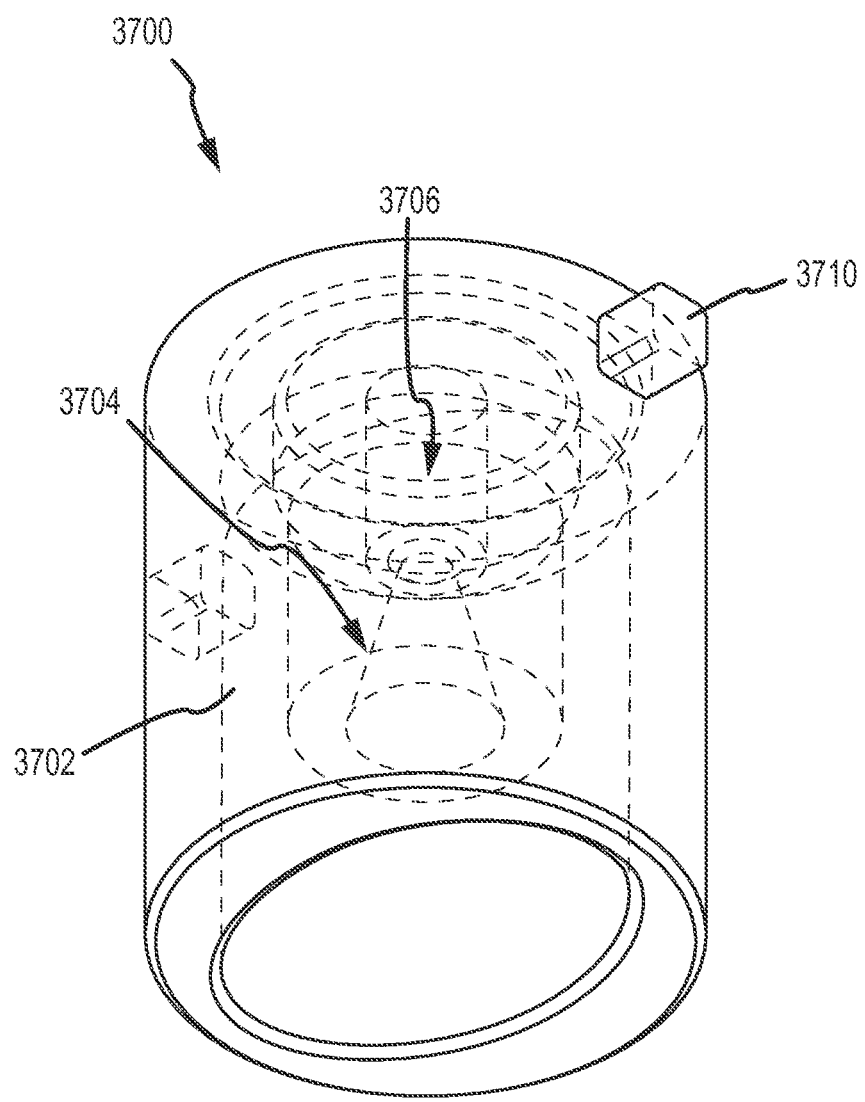
FIG. 39 shows a second perspective view of the device of FIG. 38.
Figure 40:
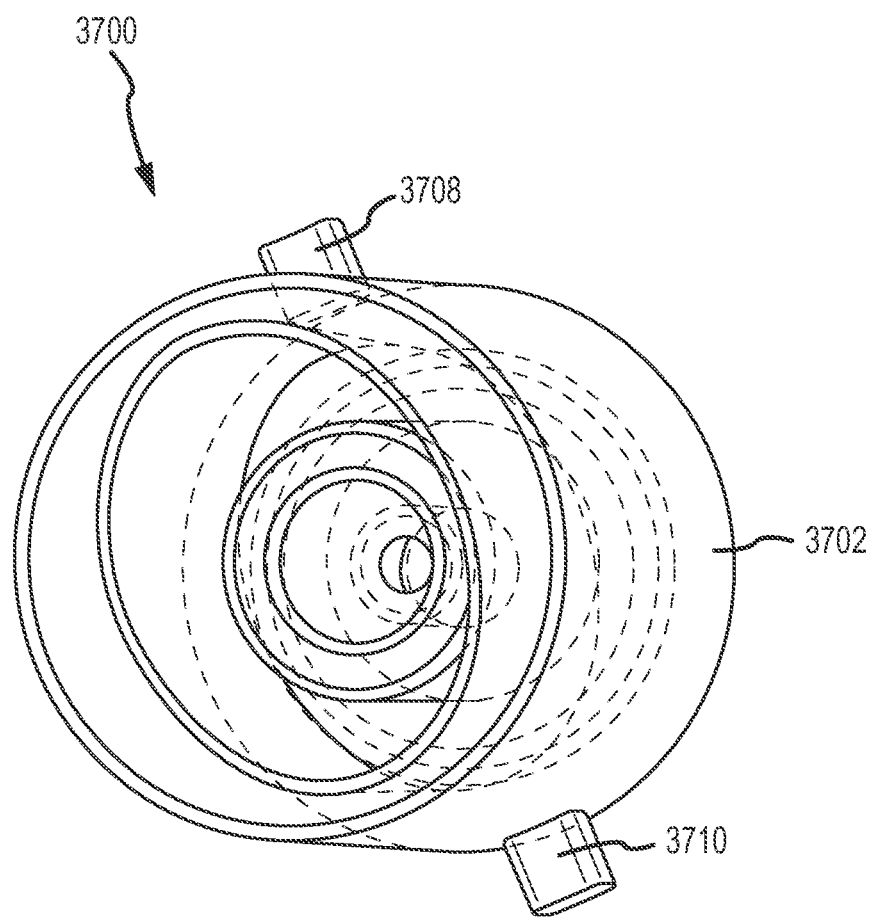
FIG. 40 shows a third perspective view of the device of FIG. 38.
Figure 41:
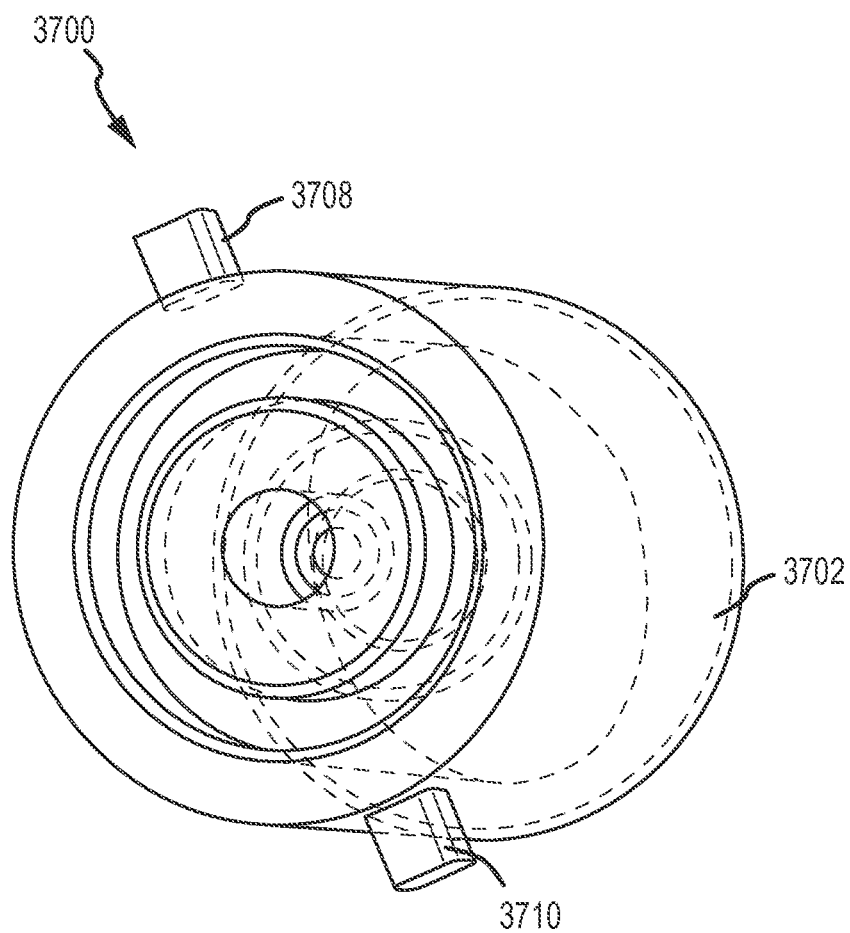
FIG. 41 shows a fourth perspective view of the device of FIG. 38.
Figure 42:
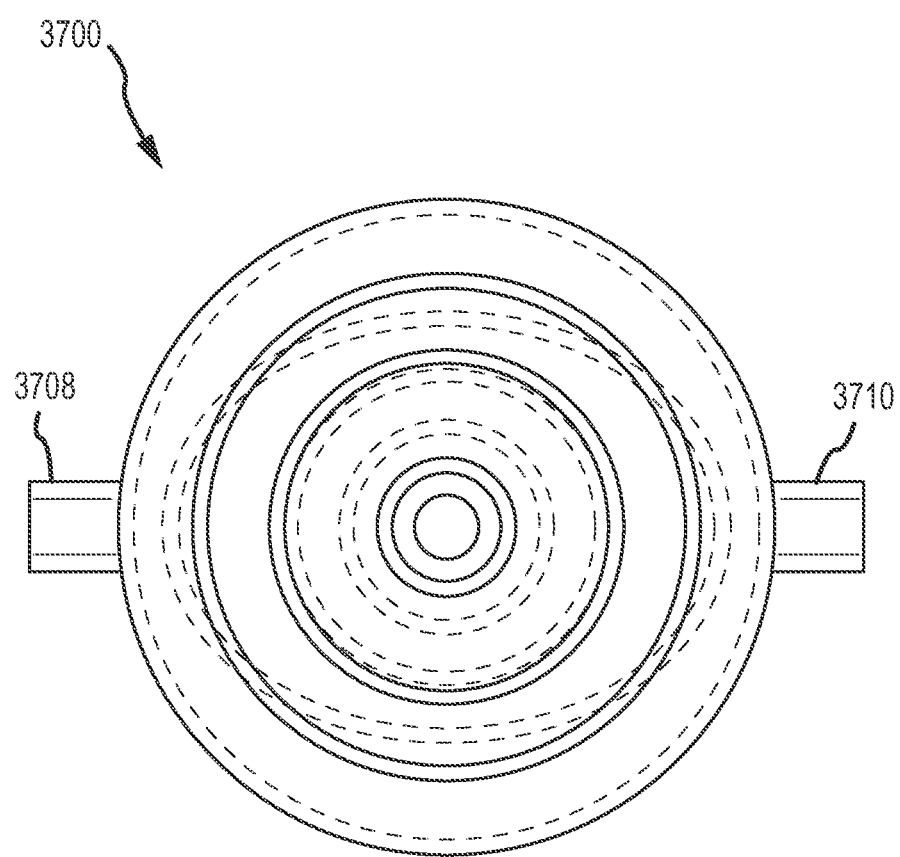
FIG. 42 shows a fifth perspective view of the device of FIG. 38.
Figure 43:
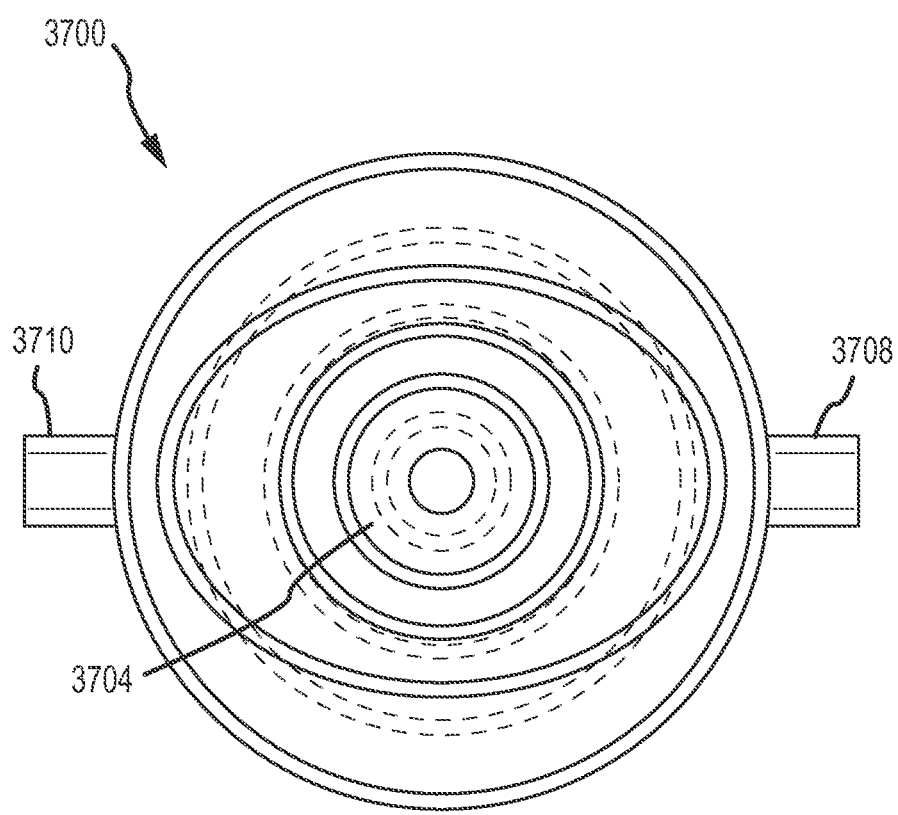
FIG. 43 shows a sixth perspective view of the device of FIG. 38.

Referring now to FIGS. 38-43, a third example powder dispersion device or inhaler 3700 is shown in accordance with the principles of the present disclosure. In general, the device 3700 may be configured to be coupled to another inhaler device. In particular, FIG. 38 shows a first perspective view of the device 3700. FIG. 39 shows a second perspective view of the device 3700. FIG. 40 shows a third perspective view of the device 3700. FIG. 41 shows a fourth perspective view of the device 3700. FIG. 42 shows a fifth perspective view of the device 3700. FIG. 43 shows a sixth perspective view of the device 3700.

In general, the device 3700 may be similar to the device 400, the device 1300, and/or the device 2500, respectively, as discussed above in connection with FIGS. 1-37. In particular, the device 3700 may be similar to or otherwise correspond to the first housing 402 of the device 400, the first housing 1302 of the device 1300, and/or the first housing 2502 of the device 2500. For example, the device 3700 may include a housing 3702 comprising an inlet 3704 and a chamber 3706. Additionally, although not expressly shown, the bead 302 may be positioned within the chamber 3706, such as shown in FIG. 3. In this example, the device 3700 may be coupled to either of the second housing 404 of the device 400, the second housing 1308 of the device 1300, and the second housing 2508 of the device 2500. For example, the housing 3702 may include a first bar 3708 and a second bar 3710. In practice, the housing 3704 may be, for example, coupled and decoupled to the second housing 2508 of the device 2500 in manner similar to that described above in connection with the device 1300. Such interchangeability may be beneficial in many respects. For example, when a bead 302 of different size is desired, the first housing 2502 may be removed and replaced with another first housing 2502 having a bead 302 of different size than the original housing. Other benefits are possible as well.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A dry powder inhaler, comprising:
    a housing having a longitudinal axis, the housing comprising:
        a powder receiving chamber within the housing that is adapted to receive an aerosolized powdered medicament from an inlet channel, wherein the inlet channel is in fluid communication with a powder storage location, and wherein the aerosolized powdered medicament flows generally axially along the longitudinal axis of the housing from the powder storage location through the inlet channel and into the powder receiving chamber;
        a dispersion chamber within the housing downstream of the powder receiving chamber that is adapted to receive at least a portion of the aerosolized powdered medicament from the powder receiving chamber, the dispersion chamber comprising substantially cylindrical side walls that are coaxial with the longitudinal axis, the dispersion chamber holding a single actuator that oscillates in a generally axial direction along the longitudinal axis, wherein the aerosolized powdered medicament flows generally axially along the longitudinal axis of the housing through the powder receiving chamber and into the dispersion chamber; and
        an outlet channel within the housing downstream of the dispersion chamber through which air and powdered medicament exit the inhaler to be delivered to a patient, wherein the aerosolized powdered medicament flows generally axially along the longitudinal axis of the housing through the dispersion chamber and into the outlet channel;

wherein a geometry of the inhaler is such that a flow profile is generated within the dispersion chamber that causes the single actuator to oscillate along the longitudinal axis, thus enabling the oscillating actuator to effectively disperse powdered medicament received in the dispersion chamber for delivery to the patient through the outlet channel; and wherein the powder receiving chamber comprises continuous side walls to define a longitudinal flow path along the longitudinal axis from the powder receiving chamber to the dispersion chamber, and wherein the side walls of the dispersion chamber are continuous to define a longitudinal flow path along the longitudinal axis from the powder receiving chamber to the outlet channel, and wherein the outlet channel comprises continuous side walls to define a longitudinal flow path from the dispersion chamber to an outlet end of the outlet channel, and wherein the flow paths of the powder receiving chamber, the dispersion chamber and the outlet channel together define a single continuous flow path that extends from an inlet end of the inlet channel to the outlet end of the outlet channel through which the powdered medicament flows from the powder storage location to the outlet end of the outlet channel, wherein the continuous side walls that define the flow paths of the powder receiving chamber, the dispersion chamber, and the outlet channel prevent air from entering the single continuous flow path except for air that is introduced to the single continuous flow path via the inlet end of the inlet channel.

2. The dry powder inhaler of claim 1, wherein a cross-sectional area of a flow path through the inhaler undergoes a step increase at an entrance to the dispersion chamber.

3. The dry powder inhaler of claim 1, wherein a ratio of a diameter of the dispersion chamber to that of the inlet channel is within a range of about greater than 1.0 to about 3.0, and wherein a ratio of a length of the dispersion chamber to a diameter of the actuator is about 1.2 to 5.

4. The dry powder inhaler of claim 1, wherein the inlet channel comprises a tube.

5. The dry powder inhaler of claim 1, wherein the inlet channel comprises a tube with a cross-section that varies along a length of the tube.

6. The dry powder inhaler of claim 1, wherein the outlet channel comprises a tube with a cross-section that varies along a length of the tube.

7. The dry powder inhaler of claim 1, wherein the outlet channel is integral to a mouthpiece adapted to be placed within the mouth of the patient.

8. The dry powder inhaler of claim 1, wherein the outlet channel is integral to a nasal adapter adapted to conform to at least one nostril of the patient.

9. The dry powder inhaler of claim 1, further comprising one or more bypass channels that receive supplemental air from external the inhaler, and deliver the supplemental air to the patient without the supplemental air having passed through at least one of a powder storage chamber and the dispersion chamber.

10. The dry powder inhaler of claim 1, further comprising a coupling that connects the dispersion chamber to the powder receiving chamber.

11. The dry powder inhaler of claim 1, further comprising a coupling that connects the dispersion chamber to the powder receiving chamber, wherein the coupling is selected from one of: a snap-fit coupling; a pressure-fit coupling; and a twist-to-fit coupling.

12. The dry powder inhaler of claim 1, further comprising a coupling that connects the dispersion chamber to the powder receiving chamber, wherein the coupling is integrally formed with dispersion chamber and removably coupled to the powder receiving chamber.

13. The dry powder inhaler of claim 1, wherein the dispersion chamber comprises an elongated geometry with a first end and a second end, the longitudinal axis extending between the first end and the second end, and wherein the single actuator oscillates between the first end and the second end generally along the longitudinal axis.

14. A dry powder inhaler system, comprising:

a receptacle containing an amount of powdered medicament; and a housing having a longitudinal axis, the housing comprising:

an inlet channel that is adapted to receive air and powdered medicament from the receptacle;

a powder receiving chamber that is adapted to receive air and powdered medicament from the inlet channel;

a dispersion chamber that is adapted to receive air and powdered medicament from the powder receiving chamber, the dispersion chamber comprising substantially cylindrical side walls that are coaxial with the longitudinal axis, the dispersion chamber holding an actuator that is movable within the dispersion chamber along the longitudinal axis; and an outlet channel through which air and powdered medicament exit the dispersion chamber to be delivered to a patient;

a flow bypass channel that extends through the housing to an outlet of the housing, wherein the flow bypass channel and the outlet channel are separated by a wall that blocks mixing of a fluid flowing through the flow bypass channel with the air and medicament flowing through the outlet channel in the housing;

wherein a geometry of the system is such that a flow profile is generated within the system that causes the actuator to oscillate along the longitudinal axis, thus enabling the oscillating actuator to effectively disperse powdered medicament received in the dispersion chamber for delivery to the patient through the outlet channel; and wherein the powder receiving chamber comprises continuous side walls to define a longitudinal flow path along the longitudinal axis from the powder receiving chamber to the dispersion chamber, and wherein the side walls of the dispersion chamber are continuous to define a longitudinal flow path from the powder receiving chamber to the outlet channel, and wherein the outlet channel comprises continuous side walls to define a longitudinal flow path from the dispersion chamber to an outlet end of the outlet channel, and wherein the flow paths of the powder receiving chamber, the dispersion chamber and the outlet channel together define a single continuous flow path that extends from an inlet end of the inlet channel to the outlet end of the outlet channel through which the powdered medicament flows from a powder storage location to the outlet end of the outlet channel, wherein the continuous side walls that define the flow paths of the powder receiving chamber, the dispersion chamber and the outlet channel prevent air from entering the single continuous flow path except for air that is introduced to the single continuous flow path via the inlet end of the inlet channel.

15. The dry powder inhaler system of claim 14, further comprising a piercing member configured to perforate the receptacle to transfer air and powdered medicament to the inlet channel.

16. The dry powder inhaler system of claim 14, wherein the receptacle is selected from one of: a capsule; a blister; and a powder reservoir.

17. The dry powder inhaler system of claim 14, wherein the actuator comprises a second powdered medicament adhered thereto, and wherein the geometry of the system is such that a flow profile is generated within the system that causes the actuator to oscillate along the longitudinal axis, thus enabling the oscillating actuator to effectively disperse the second powdered medicament received in the dispersion chamber for delivery to the patient through the outlet channel.

18. The dry powder inhaler system of claim 14, further comprising a first actuator in the powder receiving chamber, wherein the actuator in the dispersion chamber is a second actuator, wherein the geometry of the system is such that a flow profile is generated within the system that causes the first actuator to oscillate substantially along the longitudinal axis, thus enabling the oscillating first actuator to effectively disperse powdered medicament passing through the powder receiving chamber to be entrained by the air and delivered to the dispersion chamber.

19. A method for aerosolizing a powdered medicament, comprising:
  providing an inhaler comprising a powder receiving chamber, and a dispersion chamber, the dispersion chamber comprising substantially cylindrical side walls, the dispersion chamber containing a single actuator that is movable within the dispersion chamber along a longitudinal axis, and an outlet channel, wherein the powder receiving chamber comprises continuous side walls to define a longitudinal flow path along the longitudinal axis from the powder receiving chamber to the dispersion chamber, and wherein the dispersion chamber comprises continuous side walls to define a longitudinal flow path from the powder receiving chamber to the outlet channel, and wherein the outlet channel comprises continuous side walls to define a longitudinal flow path from the dispersion chamber to an outlet end of the outlet channel, and wherein the flow paths of the powder receiving chamber, the dispersion chamber and the outlet channel together define a single continuous flow path from an inlet end of the powder receiving chamber to the outlet end of the outlet channel through which the powdered medicament flows from a powder storage location to the outlet end of the outlet channel, wherein the continuous side walls that define the flow paths of the powder receiving chamber, the dispersion chamber, and the outlet channel prevent air from entering the single continuous flow path except for air that is introduced to the single continuous flow path via the inlet end of the powder receiving chamber; and
  inducing air flow and entrained medicament generally axially through the inhaler from the inlet end of the powder receiving chamber, through the dispersion chamber, and to an outlet end of the outlet channel along a longitudinal axis of the inhaler, and to cause the single actuator to oscillate within the dispersion chamber to effectively disperse powdered medicament passing through the powder receiving chamber and into the dispersion chamber for delivery to a patient through the outlet channel.

20. A method as in claim 19, wherein the powdered medicament is stored within a storage compartment, and wherein the powdered medicament is transferred from the storage compartment through an inlet channel and into the powder receiving chamber and dispersion chamber as flow is induced through the powder receiving chamber and dispersion chamber.

21. A method as in claim 19, further comprising inhaling from a mouthpiece to induce the flow through the powder receiving chamber and dispersion chamber.

* * * * *